US006677310B1

(12) United States Patent
Hosmane et al.

(10) Patent No.: US 6,677,310 B1
(45) Date of Patent: Jan. 13, 2004

(54) RING-EXPANDED NUCLEOSIDES AND NUCLEOTIDES

(75) Inventors: Ramachandra S. Hosmane, Columbia, MD (US); Ramesh K. Sood, Rockville, MD (US)

(73) Assignees: Nabi, Rockville, MD (US); University of Maryland Baltimore County, Baltinore, MD (US)

( * ) Notice: Subject to any disclaimer, the term of this patent is extended or adjusted under 35 U.S.C. 154(b) by 0 days.

(21) Appl. No.: 09/295,303

(22) Filed: Apr. 21, 1999

(51) Int. Cl.$^7$ .................. A61K 31/70; A07H 19/04; A01N 43/36; A01N 43/713
(52) U.S. Cl. .................. 514/43; 514/81; 514/45; 514/48; 514/393; 514/421; 536/27.13; 536/26.7; 536/26.23; 536/26.26
(58) Field of Search .................. 514/43, 45, 48, 514/81, 393, 421; 536/27.13, 26.7, 26.23, 26.26

(56) References Cited

U.S. PATENT DOCUMENTS 5,521,161 A * 5/1996 Malley et al. .................. 514/45
5,843,912 A * 12/1998 Hosmane et al. .............. 514/43

OTHER PUBLICATIONS

Hosmane et al. (CAPLUS 113:212564). "The synthesis and biophysical investigations of novel ring–expanded nucleosides, nucleotides, and homopolymers containing the 5:7–fused heterocyclic ring system, imidazo[4,5–e][1,4]diazepine." J. Org. Chem. (1990).*
Hosmane et al. (CAPLUS 107:77764). "Models for "fat" nucleosides and nucleotides. Synthesis of "fat" xanthine (fx), "fat" guanine (fg), "fat" hypoxanthine (fHx) analogs of the imidazo[4,5–3][1,4] diazepine system." Heterocycles (1986), 24(10), 2743–8.*

Hosmane et al. (CAPLUS 112:111494). "Conformational studies of two isomeric ring–expanded purine nucleoside and their 5'–mono– and –diphosphates derivatives." Biochem. Biophys. Res. Commun. (1989), 165(1), 106–13.*
Schneller et al. (CAPLUS 101:230220). "Synthesis and Biological evaluation of 6–amino–1H–pyrollo[3,2–c]pyridin–4(5H)–one(3,7–dideazaguanine)." J. Med. Chem. (1984), 27(12), 1737–9.*
Hosmane et al. The Synthesis and Biophysical Investigatins of Novel Ring–Expanded Nucleosides, Nucleotides, and Homopolymers Containing the 5:7–Fused Hetercyclic Ring System Imidazo[4,5–e][1,4]diazepine, J. Org. Chem. 1990, vol. 55, 5882–5890.
Hosmane et al. Models for "fat" Nucleosides and Nucleotides: Synthesis of "Fat" Xanthine (fx), "Fat" Guanine (fG), and "Fat" Hypoxanthine (fHx) Analogues of the Imidazo[4,5–e][1,4] Diazepine System Heterocycles 1986 Vol 24 2743–2748.
Omura et al. "Adechlorin, A New Adenosine Deaminase Inhibitor Containing Chlorine Production, Isolation and Properties" *Journal of Antibotics* 1985, 38, 1008–1015.

(List continued on next page.)

*Primary Examiner*—James O. Wilson
*Assistant Examiner*—Devesh Khare
(74) *Attorney, Agent, or Firm*—Paul E. White, Jr.; Manelli Denison & Selter PLLC

(57) ABSTRACT

The present invention relates to compositions comprising analogues of purine nucleosides containing a ring-expanded ("fat") heterocyclic ring, in place of purine, and an unmodified or modified sugar residue, pharmaceutically acceptable derivatives of such compositions, as well as methods of use thereof. In particular, these compositions may be utilized in the treatment of certain cancers, bacterial, fungal, parasitic, and viral infections, including, but not limited to, Acquired Immunodeficiency Syndrome (AIDS), hepatitis, Epstein-Barr and cytomegalovirus.

31 Claims, 18 Drawing Sheets

OTHER PUBLICATIONS

Nakamura et al. "Sythesis Of Coformycin" *J. Am. Chem. Soc.* 1974, 96, 4326–4327.

Woo et al. "A Novel Adenosine and Ara–A Deaminase Inhibitor, (R)–3–(2–Deoxy—D–erythropentofuranosyl)–3,6,7,8–tetrahydroimidazo[4,5–d]diazepin–8–ol," *J. Heterocycl. Chem.* 1974, 11.

Showalter et al. "Adenosine Deaminase Inhibitors, Synthesis and biological Evaluation of (+/−)3,6,7,8–Tetrahydro–3–[2–hydroxyethoxy)methyl]imidazo[4,5–d][1,3] diazepin–8–ol and Some Selected C–5 Homologues of Pentostatin" J. Med. Chem. 1983, 26, 1478–1482.

Agarwal et al. "Coformycin and Deoxycoformycin:Tight–binding Inhibitors of Adenosine " in "Chemistry and Biology of Nucleosides and Nucleotides," R. E. Harmon, R. K. Robins, and L. B. Townsend, Ed.: Academic Press, New York, 1978: pp. 159–197.

Smyth et al. "Deoxycoformycin In The Treatment Of Leukemias And Lymphomas", *Annals of the New York Academy of Sciences* 1985, 451, 123–128.

Klohs, W. D.: Kraker, A. J. "Pentostatin: future directions", *Pharmacological Reviews 1992, 44*, 459–477.

* cited by examiner

COFORMYCIN

2'-DEOXYCORMYCIN
(PENTOSTATIN)

AZEPINOMYCIN a: 1-O-acetyl-2,3,5-tri-O-benzoyl-β-D-ribofuranose, HMDS, TMSCl, TFMS, acetonitrile, 0 °C, 1h; b: 1-O-acetyl-2,3,5-tri-O-benzoyl-β-D-ribofuranose, BSTFA, TMS-I, pyridine, acetonitrile, r.t., 3h; c: guanidine hydrochloride, MeONa, MeOH, r.t., 48 h; d: MeONa, MeOH, r.t., 48 h.

1

R = β-D-ribofuruanosyl 1  2

Guanine

BMS 200475

Aciclovir

R=CH₂OH; HPMPA
R=H; PMEA

Carbavir

Ganciclovir

Compound 18-1

Compound 18-2

Compound 19

RING-EXPANDED NUCLEOSIDES AND NUCLEOTIDES

BACKGROUND OF THE INVENTION

1. Technical Field

The present invention relates to compositions comprising analogues of purine nucleosides containing a ring-expanded ("fat" or "REN", used interchangeably) heterocyclic ring, in place of purine, and an unmodified or modified sugar residue, pharmaceutically acceptable derivatives of such compositions, as well as methods of use thereof. In particular, these compositions can be utilized in the treatment of certain cancers, bacterial, fungal, parasitic, and viral infections, including, but not limited to, Acquired Immunodeficiency Syndrome (AIDS) and hepatitis.

The concept of the present invention can be extended to include pyrimidine nucleosides and pharmaceutically acceptable derivatives thereof.

2. Background Information

Acquired Immunodeficiency Syndrome (AIDS) has become the deadliest epidemic of the closing years of the 20th century (Benditt, J., Ed., "AIDS, The Unanswered Questions," *Science* 260:1253–93 (1993); Mitsuya, et al., *Science* 249:1533–44 (1990); Fauci, *Proc. Natl. Acad. Sci. USA* 83:9278 (1986); *Chemical and Engineering News* Jan. 19, 1987, p. 30, Jan. 26, 1987, p. 18, Jun. 8, 1987, p. 6, Jun. 29, 1987, p. 25; Nov. 23, 1989, pp. 12–70; Jun. 26, 1989, pp. 7–16; and Jul. 5, 1993, pp.20–27). It is caused by a retrovirus called the human immunodeficiency virus (HIV). Retroviruses contain ribonucleic acid (RNA) in their genomes instead of deoxyribonucleic acid (DNA) as is the case with mammals, including humans, and many other bacteria and viruses.

When the virus infects host cells, it uses its own enzyme called reverse transcriptase to transcribe its RNA blue-print into a double-stranded DNA, using the host nucleotide pool. The newly synthesized viral DNA, known as provirus, then gets incorporated into host cellular DNA. The host genetic machinery is then utilized to crank out new viral particles which further infect other cells, and so on.

Several approaches are currently being undertaken to confront the virus, for example, immunological reconstitution, development of a vaccine, and antiretroviral therapy. This third approach is described herein.

While the most desirable approach to check the AIDS viral epidemic would be the development of a vaccine, there are compelling factors to suggest that this approach alone will not be adequate to halt the epidemic. These factors are: (a) unlike other retroviruses, by infecting T4-lymphocytes, the HIV eliminates the very component of the immune response that recognizes antigens, and (b) the virus undergoes continually rapid mutation, resulting in several variations of viral envelope proteins, and hence viral antigenicity. This is believed to be due to high error rates intrinsic to reverse transcriptase-catalyzed genome replication (i.e., 10 times as compared with that catalyzed by human DNA polymerases) (Presson, et al., *Science* 242: 1168 (1988); Roberts, et al., *Science* 242:1171 (1988)). Therefore, simply restoring an AIDS patient's immune system, without eliminating or at least checking the extent of HIV infection, is unlikely to prove effective therapeutically. Thus, with the unlikelihood that the exponential growth and spread of the disease will be halted in the very near future by vaccine development, it is of the utmost importance to pursue antiretroviral therapy.

An antiretroviral therapeutic approach involves developing agents that can potentially suppress the replication of human immunodeficiency virus (HIV) by any of a number of mechanisms including, but not limited to, the following: (a) blocking the viral attachment to the target cell, (b) inhibiting the enzyme reverse transcriptase, and/or (c) blocking transcription and/or translation. While progress is being made on several fronts, the principal obstacle has been the non-specificity and/or toxicity of many otherwise promising antiviral agents. In this respect, exploitation of the intrinsically high error rate; Presson, et al., *Science* 242: 1168 (1988); Roberts, et al., *Science* 242:1171 (1988), of HIV reverse transcriptase to incorporate a chain-terminating nucleotide residue into the developing DNA (approach c) has good prospects for specificity.

As mentioned above, HIV reverse transcriptase makes 10 times as many errors as compared to other cellular polymerases (Presson, et al., *Science* 242: 1168 (1988); Roberts, et al., *Science* 242:1171 (1988)). Thus, the incorporation of the chain-terminating nucleotide residue has the potential advantage of specificity in that it is less likely that the normal cellular DNA polymerases would easily accept an aberrant nucleotide analogue. In fact, AZT (Mitsuya, et al., *Proc. Natl. Acad. Sci. USA* 82:7096 (1985)) (3'-azido-3'-deoxythymidine), DDI (2', 3'-dideoxyinosine) (Mitsuya et al., *Nature* 353:269 (1991)) and DDC (2',3'-dideoxycytidine) (Nasr et al., *Antiviral Res.* 14:125 (1990); Merigan et al., *Am. J. Med.* 88:11 (1990); Meng et al., *Ann. Intern. Med.* 116:13 (1992)), the currently approved therapy for AIDS, are known to operate by this chain termination mechanism. The other prospective drugs, for example, DDA and CS-87, are also known to be chain-terminators (Johnston et al., *Science* 260:1286–93 (1993); Mitsuya et al., *Science* 249:1533–44 (1990); *Chemical and Engineering News* Jan. 19, 1987, p. 30, Jan. 26, 1987, p. 18, Jun. 8, 1987, p. 6, Jun. 29, 1987, p. 25; Nov. 23, 1989, pp. 12–70; Jun. 26, 1989, pp. 7–16, and Jul. 5, 1993, pp. 20–27). Unfortunately, they all suffer from either unacceptable levels of toxicity or in vivo non-efficacy, e.g. AZT is toxic to bone marrow, DDC causes painful feet, and DDA & CS-87 are not adequately efficacious in vivo (Johnston et al., supra (1993); Mitsuya et al., supra (1990); *Chemical and Engineering News* Jan. 19, 1987, p. 30, Jan. 26, 1987, p. 18, Jun. 8. 1987, p. 6, Jun. 29, 1987, p. 25; Nov. 23, 1989, pp. 12–70; Jun. 26, 1989, pp. 7–16, and Jul. 5, 1993, pp. 20–27). Therefore, the search must continue for efficient chain-terminators with minimum toxicity so as to arrive at an ideal anti-AIDS drug.

Chain termination can occur by different mechanisms: AZT and the other drugs mentioned above, for example, lack the crucial 3'-OH function necessary for chain elongation. It is also possible that base-mispairing accompanied by considerable deviation of base-ribose conformation from the natural array leads to chain termination (see FIG. I) (Chidgeavadze, et al., *FEBS LETT*, 183:275 (1985); Chidgeavadze, et al., *Biochim. Biophys. Acta*, 868:145 (1986); Beabealashvilli et al., *Biochim. Biophys. Acta*, 868:136 (1986)).

Significant deviation of the 3'-OH group from the natural array would hinder incorporation of subsequent nucleotides into the growing polynucleotide chain and/or formation of the RNA-DNA hybrid, an important event occurring during reverse transcription. The potentially planar and aromatic nucleosides/nucleotides, which are described herein are thought to operate by this latter mechanism, as corroborated by molecular modeling studies. (Hückel MO calculations on potential aromaticity of several heterocyclic aglycons were performed using the program "HMO", available from Trinity Software, Campton, N.H.) Molecular modeling studies were performed on a Silicon Graphics™ computer, employing CHARMm™, interfaced with QUANTA™, obtained from Molecular Simulations, Inc., Boston, Mass. However, several other possible mechanisms of action cannot be ruled out.

FIG. II(A) depicts a ten-nucleotide long oligomer containing all 10 natural nucleotides, FIG. II(B) shows the corresponding oligomer with 9 natural nucleotides plus a "fat" guanine (fG) nucleotide inserted at position 5 in place of G. FIG. II(C) is a space-filling model of FIG. II(B). Extensive ABNR (Adopted Basis Newton Raphson) energy minimization performed on each duplex, Molecular modeling studies were performed on a Silicon Graphics™ computer, employing CHARMm™, interfaced with QUANTA™, obtained from Molecular Simulations, Inc., Boston, Mass., that was formed by hybridization of each oligomer with its respective complementary oligomer, shows that incorporation of a fG into a nucleic acid sequence results in considerable distortion of the double helix with severe disruption of base-pair hydrogen bonding leading to unwinding of the double helix starting from the deviant fG residue (see FIGS. II(B) and II(C)).

Implications are that the incorporation of an fG into the growing DNA chain during reverse transcription would (a) hinder incorporation of subsequent nucleotides, (b) cause base-pair disruption, mismatch, or frameshift, and/or (c) prevent formation of an RNA-DNA hybrid. Any or all of the above events lead to chain termination, and in turn, inhibit viral replication.

Even if an analogue is not a chain-terminator, the incorporation of such an aberrant nucleotide into DNA by HIV reverse transcriptase, could become self destructive, as the analogue may introduce multiple mutations in subsequent rounds of polymerization and accumulations of several such mutations would be lethal to the virus.

Still another possible mode of action that cannot be ignored is if any of the ring-expanded nucleosides turn out to be neither chain terminators nor to be incorporated into DNA. In that case, the inhibitory activity of the analogue may simply be due to its binding to one of the active or allosteric binding sites of HIV reverse transcriptase causing competitive, noncompetitive, or uncompetitive inhibition.

One other major pathogen causing severe consequences is the hepatitis B virus (HBV) which is largely prevalent in third-world countries. It is believed that 80% of the world's liver cancer is caused by HBV. The U.S. currently has 1 million infectious carriers, and chronically active hepatitis will develop in over 25% of carriers and often progresses to cirrhosis. It is estimated that about 5000 people die from cirrhosis each year in the U.S. and about 1000 people die from liver cancer caused by HBV.

Hepatitis B virus (HBV) is a DNA (2'-deoxyribonucleic acid) virus that infects humans. It is a member of the family of viruses, collectively called hepadnaviruses. These closely related viruses selectively infect either mammalian or avian hosts. Mechanistic studies on the replication of these viruses have explored the important role of reverse transcription of an RNA intermediate, strongly suggesting the viability of reverse transcriptase as a logical therapeutic target.

Hepatitis B virus infections continue to be a major worldwide health problem (Centers for Disease Controls and Prevention. *Morbid. Mort*1. *Weekly Rep*., 1995:43–963, 1995). HBV infection is known to cause acute and chronic liver hepatitis which can lead to chronicity and liver cirrhosis. Worldwide there are some estimated 350 million chronic carriers of HBV and 1–2% of them die each year from infection related complications. Chronic carriage of HBV has also been strongly associated with hepatocellular carcinoma (Beasley, R. P., et al., Overview on the epidemiology of hepatocellular carcinoma, p. 532–535, In F. B. Hollinger, S. M. Lemon, and M. Margolis (ed.), Viral Hepatitis and Liver Disease, 1991).

Several nucleoside analogs have been shown to inhibit the replication of HBV in cell cultures and in animal models (Colacino, J. M., et al., *Prog. Drug Res*., 50:260–322, 1998; Chu, C. K., et al., *Antimicrob. Agents Chemother*., 39:979–981, 1995; Doong, S.-L., et al., *Proc. Natl. Acad. Sci. USA*., 88:8495–8499, 1991; Genovesi, E. V., et al., *Antimicrob. Agents Chemother*., 42:3209–3217, 1998; Innaimo, S. F., et al., *Antimicrob. Agents Chemother*., 41:1444–1448, 1997; Korba, B. E., et al., *Antimicrob. Agents Chemother*., 40:1282–1284, 1996; Lin, T.-S., et al., *J. Med. Chem*., 37:798–803, 1994; Lin, T.-S., et al., *Biochem. Pharmacol*., 47:171–174, 1994; Nicoll, A. J., et al., *Agents Chemother*., 42:3130–3135, 1998; Yokota, T., et al., *Antimicrob. Agents Chemother*., 35:394–397, 1991; Zhu, Y.-L., et al., *Antimicrob. Agents Chemother*., 41:1755–1760, 1997). More recently, 2',3'-dideoxy-L-3'-thiacytidine (3TC) has become the first and the only nucleoside analog that has been approved for the treatment of chronic HBV infection in humans. Several other pyrimidine and purine nucleoside analogs with either modified ribose or acyclic alkyl chains as the sugar moiety have been shown to exhibit anti-HBV activity (Colacino, J. M., et al., *Prog. Drug Res*., 50:260–322, 1998; Lin, T.-S., et al., *J. Med. Chem*., 37:798–803, 1994; Lin, T.-S., et al., *Biochem. Pharmacol*., 47:171–174, 1994). Some of these nucleosides are currently being evaluated for their ability to treat HBV infections in humans (Bowden, S., *Antivir. Chem. Chemother*. 8(supple1): 77–82, 1997). For the majority of these nucleosides with anti-HBV activity, the sugar moiety of the molecule is modified to make them inhibitors of the viral polymerases. Some of the modifications which may impart antiviral activity to nucleoside analogs are: removal of 2' and/or 3'-hydroxyl as in 3TC (Doong, S.-L., et al., *Proc. Natl. Acad. Sci. USA*., 88:8495–8499, 1991); substitution of cyclic ribose with an acyclic side chain as in acyclic phosphonate analogs (Nicoll, A. J., et al., *Agents Chemother*., 42:3130–3135, 1998); or removal of ring oxygen as in carbocyclic analogs (Genovesi, E. V., et al., *Antimicrob. Agents Chemother*., 42:3209–3217, 1998; Innaimo, S. F., et al., *Antimicrob. Agents Chemother*., 41:1444–1448, 1997).

Enzymes play a crucial role in regulating the purine and pyrimidine metabolism of normal as well as rapidly proliferating cells. This fact has led to considerable research in identifying, isolating, characterizing, and studying the specific physiological role of many enzymes. This, in turn, has led to the rational design of inhibitors of a variety of enzymes. The replication of DNA of a cancer cell or a pathogen is dependent upon the availability of the deoxyribonucleoside triphosphates: dTTP, dCTP, DATP, and dGTP. Nucleotides are synthesized as ribo- and/or deoxyribonucleotides either via the de novo pyrimidine and purine pathways or via the salvage pathway using the preformed exogenous nucleobases or nucleosides. These nucleotides are used for the synthesis of new DNA strands. When there are preformed exogenous nucleobases or nucleosides, the de novo pathways are inhibited and nucleotides are synthesized via the more economical salvage pathway. Division of a cancer cell can be significantly altered or stopped by interfering with either of these two pathways The rapidly proliferating cancer cells are in high demand for nucleotide pools. Inhibition of any of the enzyme-catalyzed biosynthetic pathways by a specific enzyme inhibitor would terminate or significantly reduce the production of purine and pyrimidine nucleotides and this will lead to the death of the cell. Compounds that selectively interfere with malignant cells including nucleoside analogues are of great importance (Sartorelli and David, Springer-Verlag: Berlin (1974); Hirsch and Kaplan *Sci. Amer.*, 256, 76–85 (1987)).

Modifications of natural nucleosides have led to synthesis of therapeutically significant nucleoside analogues which are potent inhibitors of enzymes involved in nucleic acid biosynthesis and are important in the treatment of cancer and pathogenic diseases.

A few patents exist relating to 5:7-fused heterocycles and nucleosides. The compounds described therein have structural features similar to coformycin and pentostatin, the compounds depicted in FIG. 3.

In particular, U.S. Pat. No. 4,151,347 describes both coformycin and pentostatin.

U.S. Pat. No. 4,163,839 describes a coformycin analogue referred to as isocoformycin.

U.S. Pat. No. 4,713,372 describes a pentostatin analogue referred to as 2'-chloropentosatin.

U.S. Pat. No. 4,935,505 relates to coformycin analogues such as, for example, azolo diazepine.

The compounds described in the above-referenced U.S. patents are quite distant from those encompassed by the present invention.

SUMMARY OF THE INVENTION

The first aspect of the present invention relates to potentially planar and aromatic, ring-expanded analogues of purine, their nucleoside, nucleotide, and any other pharmaceutically acceptable derivatives thereof, bearing the general formula I, as shown below.

The second aspect of the present invention relates to non-planar non-aromatic ring-expanded analogues of purine heterocyclic bases, their nucleoside, nucleotide, and any other pharmaceutically acceptable derivatives thereof, bearing the general formulas II, III, and IV as shown below.

It should also be pointed out that because of their structural similarity to natural purines, ring-expanded nucleosides or nucleotides are an abundant source of substrates and/or inhibitors of enzymes of purine metabolism, as well as of those requiring ATP or GTP cofactors. Indeed, there is a precedence for their potential ability to inhibit enzymes of purine metabolism. The naturally occurring synergistic antitumor antibiotics, coformycin (Ohno et al., *J. Am. Chem. Soc.* 96:4326 (1974), Umezawa et al., Ger. Offen 2,453,649 (1975), Glazer, *Rev. Drug. Metab. Drug. Interact.* 105:3 (1980); Hawkins, et al., *Nucleosides and Nucleotides* 2:479 (1983)), and 2'-deoxycoformycin (pentostatin) (Woo et al., *J. Heterocycl. Chem.* 11:641 (1974), Baker et al., *J. Am. Chem. Soc.* 101:6127 (1079), Chan, et al., *J. Org. Chem.* 47:3457 (1982), Hanvey, et al., *Biochemistry* 23:904 (1984)), (see FIG. 3), are 5:7-fused nucleosides containing the imidazo [4,5-d][1,3] diazepine nucleus, and are the two strongest inhibitors of adenosine deaminase (ADA) known, with a $K_i$ as high as $10^{-11}$. Another recently isolated natural product called azepinomycin, also a 5:7-fused system, but a non-nucleoside (see FIG. 3) containing the imidazo [4,5-e][1,4] diazepine ring, is reported to be an inhibitor of guanase (Umezawa, et al., *Jpn. Kokai Tokyo Koho JP* 58,159,494 [83,159,494]; *Chem. Abstr.* 100:137362x (1984); Isshiki, et al., *J. Antibiot.* 40:1461 (1987); Fujii, et al., *Heterocycles* 27:1163 (1988)). All three molecules and their synthetic analogues however, are non-planar or puckered (Acevedo, et al. *Tetrahedron Lett.* 24:4789 (1983), Acevedo et al., *J. Heterocycl. Chem.* 22:349 (1985), Acevedo, et al., *J. Org. Chem.* 51:1050 (1986)). They also possess tetrahedral geometry at the hydroxyl junction of their seven-membered ring, and therefore, are viewed as transition state analogue inhibitors of ADA (Agarwal et al. "Coformycin and Deoxycoformycin: Tight-binding Inhibitors of Adenosine Deaminase", in "Chemistry and Biology of Nucleosides and Nucleotides," Harmon et al., Academic Press, New York, pp. 159–197 (1978)), or guanase (Umezawa, et al., *Jpn. Kokai Tokyo Koho JP* 58,159,494 83,159,494; *Chem. Abstr.* 100:137362x (1984); Isshiki, et al., *J. Antibiot.* 40:1461 (1987); Fujii, et al., *Heterocycles* 27:1163 (1988)).

The physiological significance of inhibiting ADA lies in the fact that the enzyme inactivates the otherwise potential antiviral and antitumor drugs such as 8-azaadenosine, ara-A or formycin by rapid hydrolysis to the corresponding inosine analogues. While the physiological significance of inhibiting guanase is less clear, several reports have recently appeared regarding detection of abnormally high levels of serum guanase activity in patients with liver disease like hepatitis (Shiota et al., *Jpn. J. Med.* 28:22 (1989), Ito et al., *Hepatology* 8:383 (1988)). High serum guanase activity has also been reported to be a biochemical indicator of rejection in liver transplant recipients (Crary et al., *Transplant Proc.* 21:2315 (1989)).

It should also be noted that, in addition to viruses, bacteria represent a medical therapeutic problem and experience has indicated that, over time, certain strains develop resistance to the commonly used antibacterial agents. It is now known that certain of the purine or pyrimidine nucleoside analogues are useful as antibacterial agents, particularly gram negative bacterial infections.

The compounds of the present invention can be used in the treatment or prophylaxis of bacterial infections. The compounds can also be utilized in the production of medications for the treatment or prophylaxis of bacterial infections. Particular bacteria against which the compounds of the invention are useful include *Escherichia coli*, Salmonella spp., *Shigella flexneri, Citrobacter freundii, Klebsiella pneumoniae*, Vibrio spp., *Haemophilus influenzae, Yersinia enterolitica, Pasturella haemolytica*, and Proteus spp. These agents are responsible for the following diseases: travelers' diarrhea, urinary tract infections, typhoid fever, cholera, shigellosis, and veterinary diseases including enteritis, and colisepticaemia.

Furthermore, it is known that nucleoside analogues operate synergistically with a wide range of other therapeutic agents, enhancing the therapeutic effects of each in a non-additive manner, raising the therapeutic index, and reducing the risk of toxicities from either compound. The activity of the compounds of the present invention, against a wide range of viral and bacterial infections, as well as their novel mechanism of action, may therefore be particularly useful in combination therapies including various combinations of the present compounds with each other and with other therapeutic and/or synergistic compounds and pharmaceutically acceptable carriers. Such combinations have oral, topical, opthalmic, otic, nasal, intraperitoneal, subcutaneous, intervenous and suppository use. Furthermore, veterinary medical applications are also possible as well as use as a feed additive for vertebrate animals.

Typically, there is an optimum ratio of the compound(s) of the present invention with each other and/or with other therapeutic or potentiating agents (such as transport inhibitors, metabolic inhibitors, renal excretion or glucuronidation inhibitors such as probenecid, acetaminophen, aspirin, lorazepam, cimetidine, ranitidine, clofibrate, indomethacin, ketoprofen, naproxen, etc.) wherein the active agents are present in an optimum ratio. An "optimum ratio" is defined as the ratio of the compound(s) of the present invention with another therapeutic agent or agents such that the overall therapeutic effect is greater than the sum of the effects of the individual therapeutic agents. The optimum ratio is usually observed when the agents are present in ratios of 10:1 to 1:10, 20:1 to 1:20, 100:1 to 1:100, and 500:1 to 1:500. Occassionally, even a vanishingly small amount of one therapeutic agent will suffice to potentiate the activity of one or more other agents. In addition, the use of the compounds of the present invention in combinations is particularly useful in reducing the chance of the development of resistance.

In the antibacterial field, it has previously been found that a wide range of antibiotics is effective in potentiating the activity of nucleoside analogues. This includes agents such as benzylpyrimidines, pyrimidines, sulphonamides, rifampicin, tobramycin, fusidic acid, clindamycin, chloramphenicol, and erythromycin. Therefore, an additional embodiment of the present invention relates to a combination wherein the second agent is at least one of the above-mentioned antiviral or antibacterial agents or classes of agent. It should also be noted that the compounds and combinations of the invention can also be used in conjunction with immune modulating therapeutics and therapy.

In view of the above, the compounds of the present invention provide for a therapeutic combination of these compounds, or a pharmaceutically acceptable derivative thereof. At least one additional therapeutic agent may also be included. Furthermore, one compound of the present invention may also be combined with at least one known and commonly used therapeutic agent. Such grouping of compounds or agents will hereinafter be referred to as "combinations." The combinations may be administered together, for example, in a unitary pharmaceutical formulation, or separately, for example, as combinations of tablets, injections, or other medicaments administered at the same time or at different times with the goal of achieving the desired therapeutic effect.

A "pharmaceutically acceptable" derivative means any pharmaceutically acceptable salt, phosphonate, ester, or salt of such ester, or any other compound which is capable of providing the parent compound or compounds of the present invention or a therapeutically effective metabolite or residue thereof. Examples of pharmaceutically acceptable salts of the present invention and pharmaceutically acceptable derivatives thereof include phosphorus compounds and phosphonates, base salts, e.g., derived from an appropriate base such as an alkali metal, an alkaline earth metal, ammonium and mineral acid salts, such as the hydrochloride.

In view of the above, the present invention encompasses potentially planar, aromatic, ring-expanded ("fat") heterocyclic bases, nucleosides and nucleotide compounds having the structure

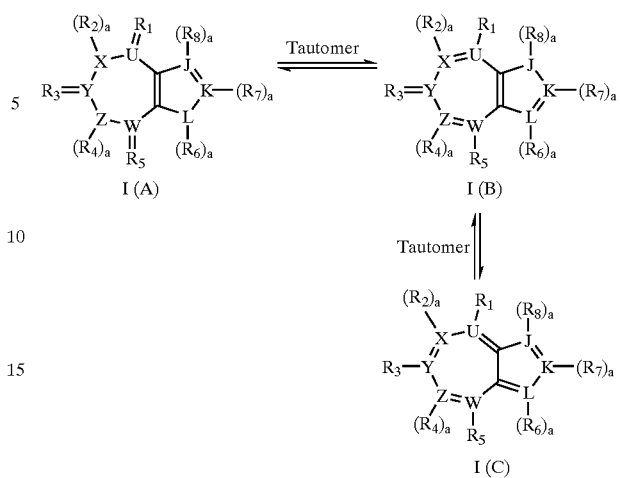

wherein:
R$_1$, R$_3$ and R$_5$ are each independently selected from:
NH, NH$_2$, O, OH, S, and SH;
NH-alkyl, N-alkyl, O-alkyl and S-alkyl wherein the alkyl group is C$_1$–C$_{20}$;
NH-aryl, O-aryl and S-aryl wherein the aryl group is a substituted or unsubstituted phenyl or heterocyclic group;
N-glycosyl and NH-glycosyl wherein the glycosyl group is selected from the group consisting of ribosyl, 2'-deoxyribosyl, 2',3'-dideoxyribosyl, 2',3'-dideoxy-3'-azidoribosyl, 2',3'-dideoxy-2'-fluororibosyl, 2',3'-dideoxy-3'-fluororibosyl, 2',3'-dideoxy-2',3'-difluororibosyl, and mono-, di- and triphosphosphate derivatives thereof;
N—(CH$_2$)$_m$—XR'—(CH$_2$)$_n$—YR', NH—(CH$_2$)$_m$—XR'—(CH$_2$)$_n$—YR', O—(CH$_2$)$_m$—XR'—(CH$_2$)$_n$—YR' and S—(CH$_2$)$_m$—XR'—(CH$_2$)$_n$—YR' wherein R' is selected from the group consisting of hydrogen, a C$_1$–C$_{20}$ alkyl group, H$_2$PO$_3$, H$_3$P$_2$O$_6$, H$_4$P$_3$O$_9$ and the alkali metal or alkaline earth metal salts thereof;
R$_2$, R$_4$, R$_6$, R$_7$, R$_8$ are each independently selected from:
hydrogen, a C$_1$–C$_{20}$ alkyl group, an aryl group which is a substituted or unsubstituted phenyl or heterocyclic group, and an aralkyl group wherein the aryl and alkyl portions of the group have the definitions given above;
a glycosyl group wherein said glycosyl group is selected from the group consisting of ribosyl, 2'-deoxyribosyl, 2',3'-dideoxyribosyl, 2',3'-dideoxy-2'-fluororibosyl, 2',3'-dideoxy-3'-fluororibosyl, 2',3'-dideoxy-2',3'-difluororibosyl 2',3'-dideoxy-3'-azidoribosyl and mono-, di-, and triphosphate derivatives thereof;
(CH$_2$)$_m$—XR'—(CH$_2$)$_n$—YR' wherein R' is selected from the group consisting of:
hydrogen, H$_2$PO$_3$, H$_3$P$_2$O$_6$, H$_4$P$_3$O$_9$, and alkali metal or alkaline earth metal salts thereof;
m is zero to 20, n is zero to 20, and a is zero or one; and
U, X, Y, Z, W, J, K, and L are selected from the group consisting of C, N, O, P, and S. U, X, Y, Z, W, J, K and L are selected from the group consisting of carbon (C) and nitrogen.

Formula I(B) can be 4,8-diamino-6-imino-1H-imidazo[4,5-e][1,3]diazepine wherein R, and R$_5$ are NH$_2$, R$_3$ is NH, R$_7$ and R$_8$ are H, and a for R$_2$, R$_4$ and R$_6$ is zero.

Formula I(B) can also be 4,8-diamino-1-benzyl-6-iminoimidazo[4,5-e][1,3]diazepine, wherein $R_1$ and $R_5$ are $NH_2$, $R_3$ is NH, $R_7$ is H, $R_8$ is benzyl ($CH_2Ph$) and a for $R_2$, $R_4$ and $R_6$ is zero.

Formula I(A) can be 6-imino-1H-imidazo[4,5-e][1,3]diazepine-4,8-dione, wherein $R_1$ and $R_5$ are O, $R_3$ is NH; $R_2$, $R_4$, $R_6$ and $R_7$ are H, and a is zero for $R_8$.

Furthermore, formula I(A) can also be 4,6,8-triimino-1-β-D-ribofuranosylimidazo[4,5-e][1,3]diazepine, wherein $R_1$, $R_3$ and $R_5$ are NH, $R_2$, $R_4$ and $R_7$ are H, $R_6$ is 1-β-D-ribofuranosyl, and a for $R_8$ is zero.

Furthermore, it must be noted that the present invention includes all chiral forms and stereoisomers of the compounds presented above.

As noted above, the present invention also includes compounds comprising non-planar, non-aromatic, ring-expanded ("fat") heterocyclic bases, nucleosides or nucleotides having the formula II

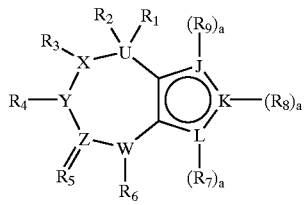

Formula II wherein:
$R_1$ and $R_2$ are each independently selected from H, $OR_3$, $SR_3$, $NHR_3$, $CO_2R_3$, $CONHR_3$, $CONHNHR_3$, $CH_2OR_3$, $CH_2NHR_3$, and $CH_2R_3$;

$R_3$, $R_4$ and $R_6$ are each independently selected from:
hydrogen, a $C_1$–$C_{20}$ alkyl group, an aryl group which is a substituted or unsubstituted phenyl or heterocyclic group, and an aralkyl group wherein the aryl and alkyl portions of the group have the meanings given above;

$R_5$ is selected from the group consisting of O, S and NH; and $R_7$, $R_8$ and $R_9$ each are independently selected from:
hydrogen, a $C_1$–$C_{20}$ alkyl group, an aryl group which is a substituted or unsubstituted phenyl or heterocyclic group, and an aralkyl group wherein the aryl and alkyl portions of the groups have the meanings given above;
a glycosyl group wherein said glycosyl group is selected from the group consisting of ribosyl, 2'-deoxyribosyl, 2',3'-dideoxy-3'-azidoribosyl, 2',3'-dideoxy-2'-fluororiboxyl, 2',3'-dideoxy-3'-fluororibosyl, 2',3'-dideoxy-2',3'-difluororiboxyl, and mono-, di- and triphosphate derivatives thereof; and
$(CH_2)_m$—$XR'$—$(CH_2)_n$—$YR'$ wherein R' is selected from the group consisting of:
H, $H_2$, $H_2PO_3$, $H_3P_2O_6$, $H_4P_3O_9$, and alkali metal or alkaline earth metal salts thereof;
m is zero to 20, n is zero to 20, and a is zero or one; and
U, X, Y, Z, W, J, K, and L are selected from the group consisting of C, N, O, P, and S. U, X, Y, Z, W, J, K and L may be selected from C and N.

Formula II can be 4,5,6,7-tetrahydro-8-hydroxy-8H-1-β-D-ribofuranosyl[4,5-d][1,3]diazepine-5-one wherein $R_1$ is OH, $R_2$, $R_4$, $R_6$ and $R_8$ are H, $R_5$ is O, $R_3$ is $H_2$, $R_9$ is 1-B-D-ribofuranosyl, and a for $R_7$ is zero.

Furthermore, it must be noted that the present invention includes all chiral forms and stereoisomers of the compounds presented above.

Additionally, the present invention includes non-planar, non-aromatic, ring-expanded ("fat") heterocyclic bases, nucleosides or nucleotides having the following formulas III and IV:

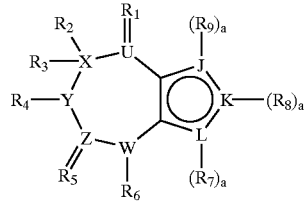

Formula III

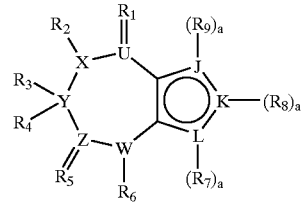

Formula IV wherein:
$R_1$ and $R_4$ are each independently selected from O, S, and NH;

$R_3$ and $R_4$ are each independently selected from H, $OR_2$, $SR_2$, $NHR_2$, $CO_2R_2$, $CONHR_2$, $CONHNHR_2$, $CH_2OR_2$, $CH_2NHR_2$, and $CH_2R_2$;

$R_2$ and $R_6$ are each independently selected from:
hydrogen, a $C_1$–$C_{20}$ alkyl group, an aryl group which is a substituted or unsubstituted phenyl or heterocyclic group, and an aralkyl group wherein the aryl and alkyl portions of the group have the meanings given above;

$R_7$, $R_8$, and $R_9$ are each independently selected from:
hydrogen, a $C_1$–$C_{20}$ alkyl group, an aryl group which is a substituted or unsubstituted phenyl or heterocyclic group, and an aralkyl group wherein the aryl and alkyl portions of the groups have the meanings given above;
a glycosyl group wherein said glycosyl group is selected from the group consisting of ribosyl, 2'-deoxyribosyl, 2',3'-dideoxy-3'-azidoribosyl, 2',3'-dideoxy-2'-fluororibosyl, 2',3'-dideoxy-3'-fluororibosyl, 2',3'-dideoxy-3'-difluororibosyl, and mono-, di-, and triphosphate derivatives thereof;
$(CH_2)_m$—$XR'$—$(CH_2)_n$—$YR'$ wherein R' is selected from:
hydrogen, $H_2PO_3$, $H_3P_2O_6$, $H_4P_3O_9$, and alkali metal or alkaline earth metal salts thereof;
m is zero to 20, n is zero to 20, and a is zero or one; and
U, X, Y, Z, W, J, K, and L are selected from the group consisting of C, N, O, P, and S.

Formula (IV) may be 4,5,7,8-tetrahydro-6-hydroxy-3H,6H-imidazo[4,5-e][1,4]diazepine-5,8-dione, wherein $R_1$ and $R_5$ are O, $R_3$ is OH, $R_2$, $R_4$, $R_6$, $R_7$ and $R_8$ are H, and a for $R_9$ is zero.

Furthermore, it must be noted that the present invention includes all chiral forms and stereoisomers of the compounds presented above.

The present invention also includes a method of treating a viral, bacterial, fungal or parasitic infection in a patient or vertebrate animal comprising administering at least one of the compounds noted above in an amount sufficient to effect the treatment.

The virus causing the infection may be selected from the group consisting of human immunodeficiency virus, Human B lymphotropic virus, Herpes simplex virus, Varicella-zoster virus, Epstein-Barr virus, necrotic rhinitis, Malignant catarrh, Allerton virus, Equine herpesviruses, Neurolymphomatosis, Influenza viruses, Parainfluenza viruses, Adenoviruses, Rheovirus, Respiratory syncytial virus, Rhinoviruses, Coxsackie virus, Echo viruses, Epidemic gastroenteritis virus, Rubeola virus, Hepatitis viruses, cytomegalovirus and Papovavirus.

The compound can be administered subcutaneously, intravenously, intramuscularly, intraperitoneally, orally, topically, or by a combination thereof.

Treatment can involve administering at least one of the compounds of the present invention in combination with at least one other known therapeutic agent.

The present invention also includes a pharmaceutical composition comprising at least one of the above-compounds and a pharmaceutically acceptable carrier.

All U.S. patents and publications referred to herein are hereby incorporated by reference.

BRIEF DESCRIPTION OF THE DRAWINGS

FIG. 1 shows a schematic representation of chain termination due to conformational deviation.

FIG. 2 represents molecular models of: (A) a duplex containing ten natural nucleotide basepairs, and (B) a duplex with nine natural nucleotide pairs present in (A) plus a "fat" guanine (fg) nucleotide at position 5 base-paired with C. (C) represents the space-filling model of (B).

FIG. 3 shows the chemical structures of the naturally occurring synergistic antitumor antibiotics Coformycin (3A), Pentostatin (3B), and Azepinomycin (3C). These compounds have a ring-expanded heterocyclic and/or nucleoside structure.

FIG. 4 is a schematic showing the synthesis of the EXAMPLE 13 target compound, 6-Imino-6H-1-β-D-ribofuranosyl-4,5,7,8-tetrahydroimidazo[4,5-e][1,3]diazepine-4,8-dione.

FIG. 5 shows the chemical structure of the EXAMPLE 14 Compound 14-1, and EXAMPLE 16 Compound 16-1, i.e., 6-imino-6H-1-β-D-ribofuranosyl-4,5,7,8-tetrahydroimidazo[4,5-e][1,3]diazepine-4,8-dione.

FIG. 6 shows the chemical structure of the EXAMPLE 14 Compound 14-2, and the EXAMPLE 16 Compound 16-2, i.e., 4,8-Diamino-6H-6-imino-1-β-D-ribofuranosylimidazo[4,5-e][1,3]diazepine.

FIG. 7 shows EXAMPLE 15 Compound 15-1 in tautomeric form, i.e., 4,6-diamino-8-imino-8H-1-β-D-ribofuranosylimidazo[4,5-e][1,3]diazepine FIG. 8 is a schematic showing the synthesis of EXAMPLE 15 Compound 15-2, i.e., the 5'-triphosphate derivative of 4,6-diamino-8-imino-8H-1-β-D-ribofuranosylimidazo[4,5-e][1,3]diazepine.

FIG. 9 is an autoradiogram of gels from the transcription experiments using a 42-mer template, as described in EXAMPLE 15.

FIG. 10 is an autoradiogram of gels from the transcription experiments using a 37-mer template, as described in EXAMPLE 15.

FIG. 11 shows relative yields in EXAMPLE 15, of full-length RNA transcript (20-mer) in reactions using template I, T7 RNA polymerase, and varying concentrations of nucleotide Compound 15-2, as described in the Experimental section of EXAMPLE 15. Relative yields were determined by scanning densitometry of autoradiograms, analyzed by gel electrophoresis of the [α$^{32}$P]GTP-labeled transcript.

FIG. 12 shows the chemical structure of Compound 16-2b, i.e., 4,8-Diamino-6H-6-imino-1(2',3',5'-tri-O-benzoyl-β-D-ribofuranosyl)imidazo[4,5-e][1,3]diazepine.

FIG. 13 shows the chemical structure of EXAMPLE 17 Compound 17-1 and Compound 17-2.

FIG. 14 shows the chemical structure of six guanine analogs.

FIG. 15 shows the chemical structure of EXAMPLE 18 Compound 18-1 and Compound 18-2.

FIG. 16 shows the chemical structure of EXAMPLE 19 Compound 19.

DETAILED DESCRIPTION OF THE INVENTION

Figure 1:
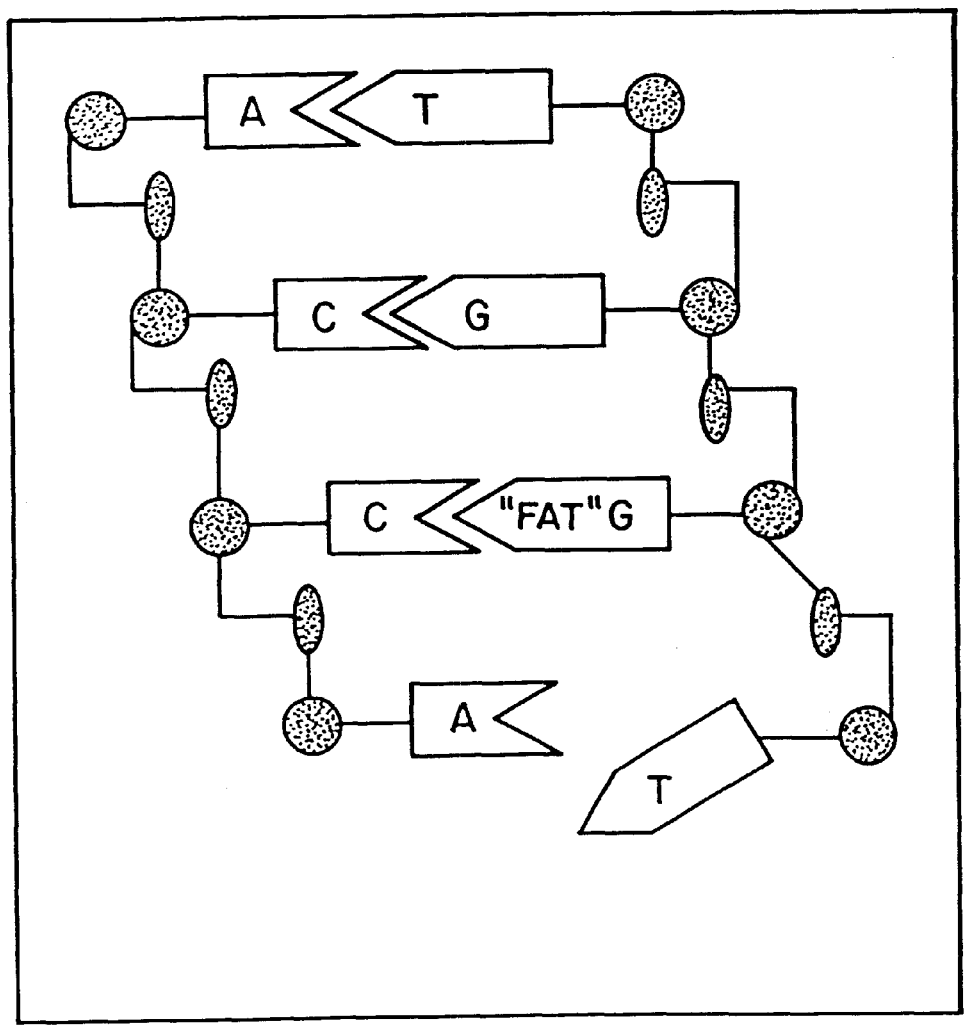
FIGS. 1 to 16
Figure 2A:
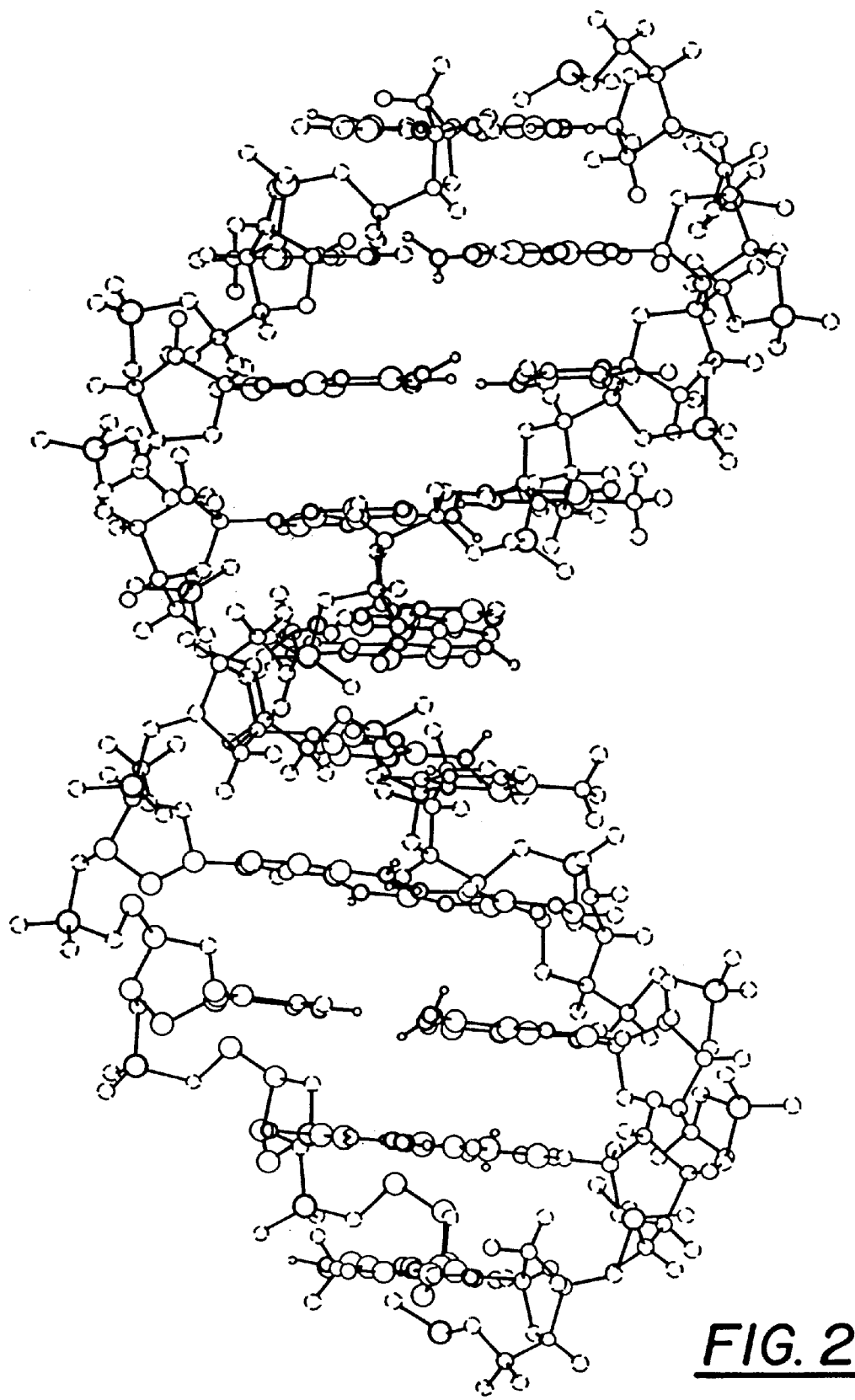
Figure 2B:
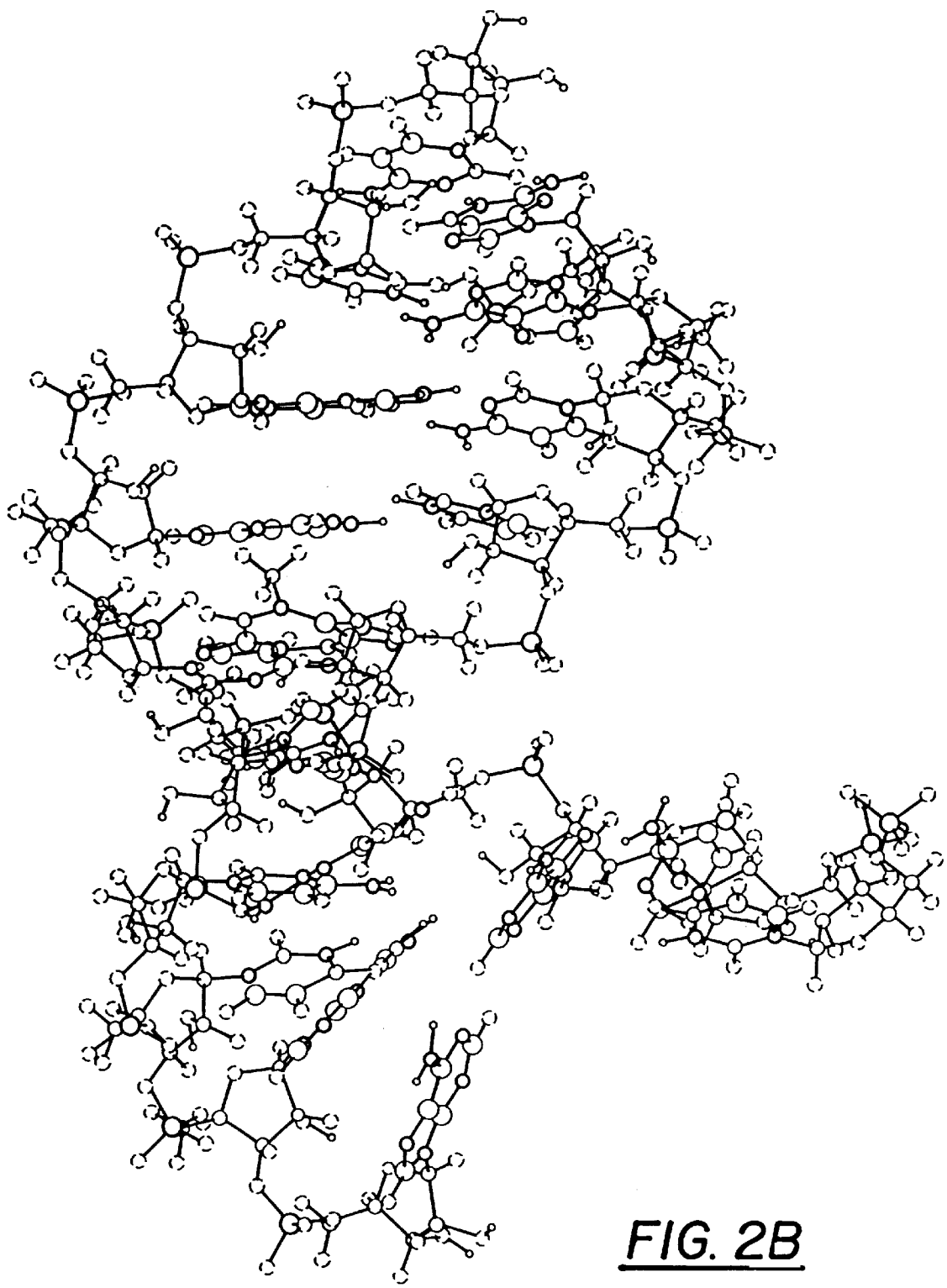
Figure 2C:
Figure 3A:
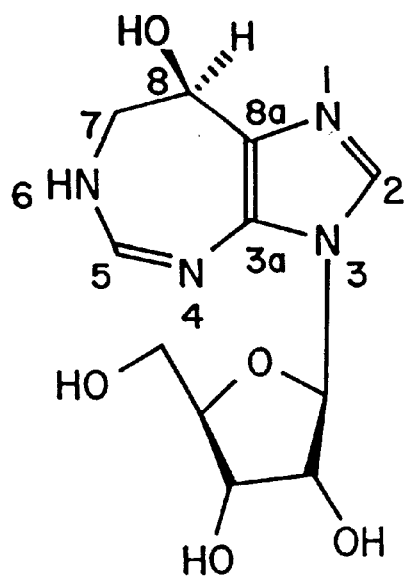
Figure 3B:
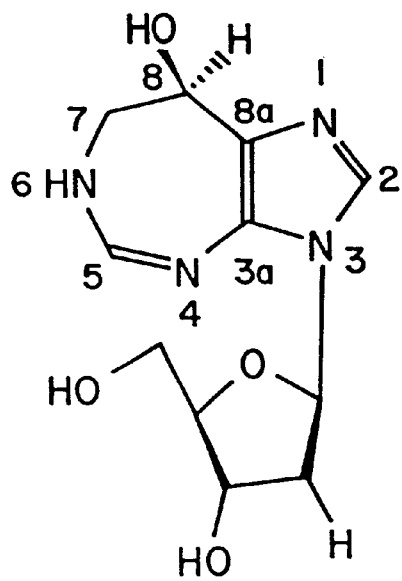
Figure 3C:
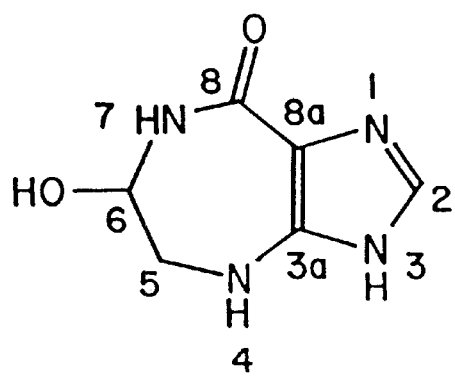

One embodiment of the present invention relates to compositions comprising planar aromatic, ring-expanded ("fat") heterocyclic bases, nucleosides or nucleotides. These bases, nucleosides or nucleotides have formulas I(A), I(B) and I(C):

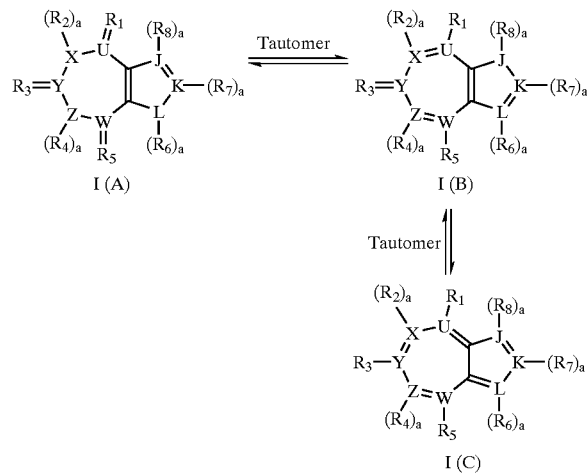

wherein:
$R_1$, $R_3$ and $R_5$ are each independently selected from:
  NH, $NH_2$, O, OH, S, and SH;
  NH-alkyl, N-alkyl, O-alkyl and S-alkyl wherein said alkyl group is $C_1$–$C_{20}$; NH-aryl, O-aryl and S-aryl wherein said aryl group is a substituted or unsubstituted phenyl or heterocyclic group;
  N-glycosyl and NH-glycosyl wherein said glycosyl group is selected from the group consisting of ribosyl, 2'-deoxyribosyl, 2',3'-dideoxyribosyl, 2',3'-dideoxy-3'-azidoribosyl, 2',3'-dideoxy-2'-fluororibosyl, 2',3'-dideoxy-3'-fluororibosyl, 2',3'-dideoxy-2',3'-difluororibosyl, and mono-, di- and triphosphosphate derivatives thereof;
  N—$(CH_2)_m$—XR'—$(CH_2)_n$YR', NH—$(CH_2)_m$—XR'—$(CH_2)_n$—YR', O—$(CH_2)_m$—XR'—$(CH_2)_n$—YR' and S—$(CH_2)_m$—XR'—$(CH_2)_n$—YR' wherein R' is selected from the group consisting of hydrogen, a $C_1$–$C_{20}$ alkyl group, $H_2PO_3$, $H_3P_2O_6$, $H_4P_3O_9$ and the alkali metal or alkaline earth metal salts thereof;

$R_2$, $R_4$, $R_6$, $R_7$, $R_8$ are each independently selected from:
hydrogen, a $C_1$–$C_{20}$ alkyl group, an aryl group which is a substituted or unsubstituted phenyl or heterocyclic group, and an aralkyl group wherein the aryl and alkyl portions of the group have the definition given above;
a glycosyl group wherein said glycosyl group is selected from the group consisting of ribosyl, 2'-deoxyribosyl, 2',3'-dideoxyribosyl, 2',3'-dideoxy-2'-fluororibosyl, 2',3'-dideoxy-3'-fluororibosyl, 2',3'-dideoxy-2',3'-fluororibosyl, 2',3'-dideoxy-3'-azidoribosyl and mono-, di-, and triphosphate derivatives thereof;
$(CH_2)_m$—XR'—$(CH_2)_n$—YR' wherein R' is selected from the group consisting of:
hydrogen, $H_2PO_3$, $H_3P_2O_6$, $H_4P_3O_9$, and alkali metal or alkaline earth metal salts thereof;
m is zero to 20, n is zero to 20 and a is zero or one; and
U, X, Y, Z, W, J, K, and L are selected from the group consisting of C, N, O, P, and S.

Furthermore, it must be noted that the present invention includes all chiral forms and stereoisomers of the compounds presented above.

The compositions may also contain a "pharmaceutically acceptable carrier," for example, water, saline, Ringer's or lactated Ringer's solution, aqueous dextrose (as well as glucose, fructose, lactose, and related sugar solutions), glycols (e.g., propylene or polyethylene glycol), starch and its derivatives, fluorocarbons, cellulose derivatives, magnesium sterate, stearic acid, suitable stabilizing, buffering and preservative agents and/or other therapeutic compounds (hereinafter "pharmaceutically acceptable carrier"). Each carrier must be "acceptable" in the sense of being compatible with the other ingredients of the formulation and not injurious to the patient or recipient. Formulations with pharmaceutically acceptable carriers include those suitable for oral, rectal, nasal, topical (including buccal and sublingual), vaginal, or parenteral (including subcutaneous, intramuscular, intravenous and intradermal) administration. The formulations may be prepared in unit dosage forms and may be prepared by various methods well known in the art of pharmacy, such as bring the active ingredient into association with liquid or finely divided solid carriers which may consist of one or more accessory ingredients, and then, if necessary, shaping and coating the product.

In order to synthesize the compounds. of Formula I, 4,5-dicyano- or 4,5-diacylhaloimidazole, substituted or unsubstituted at the 1-, 2-,or 3-position, can be condensed with a nucleophile such as guanidine, urea or thiourea, using a polar solvent such as, for example, methanol, ethanol or acetonitrile, normally at reflux conditions. The solid separated can be filtered, dried, and recrystallized from an appropriate solvent. Further modifications of the product, such as N-, O-, or S-alkyl/aryl derivatives, can be made by standard derivatization procedures, for example, by treatment with alkyl or aryl halides. Ribosylation or deoxyribosylation can be carried out using standard glycosylation conditions that have been employed frequently in this lab (Bhan et al., *Nucleosides and Nucleotides* 11:1175 (1992); Bhadti et al., *Nucleosides and Nucleotides* 11:1137 (1992); Hosmane et al., *Nucleosides and Nucleotides* 10:1693 (1991); (Hosmane, et al., *Nucleosides and Nucleotides* 10:819 (1991); Hosmane et al., *J. Org. Chem.* 55:5882 (1990); Hosmane, et al., *Nucleosides and Nucleotides* 9:913 (1990)). The mono-, di-, and triphosphate derivatives of the nucleosides can be prepared by standard chemical (Scheit, "Nucleotide Analogs: Synthesis and Biological Function," John Wiley, New York 1980, pp. 195–218)); Petrie, et al., *J. Med. Chem.* 29:268 (1986)); Moffatt, et al., *J. Am. Chem. Soc.* 83:649 (1961)) or enzymic (Leonard et al., *Biochemistry* 17:3677 (1978); Frieden, et al., *Biochem. Biophys. Res. Commun.* 91:278 (1979)) methods of phosphorylation. (Hosmane et al., *J. Org. Chem.* 55:5882 (1990)).

Another embodiment of the present invention relates-to compositions comprising non-planar, non-aromatic, ring-expanded (fat") heterocyclic bases, nucleosides or nucleotides. These bases, nucleosides or nucleotides have the following formulas (II), (III), and (IV):

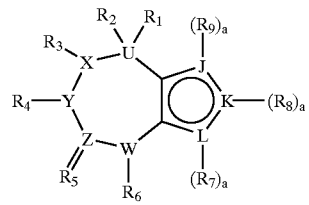

Formula II wherein, in formula II:

$R_1$ and $R_2$ are each independently selected from H, $OR_3$, $SR_3$, $NHR_3$, $CO_2R_3$, $CONHR_3$, $CONHNHR_3$, $CH_2OR_3$, $CH_2NHR_3$, and $CH_2R_3$;

$R_3$, $R_4$ and $R_6$ are each independently selected from:
hydrogen, a $C_1$–$C_{20}$ alkyl group, an aryl group which is a substituted or unsubstituted phenyl or heterocyclic group, and an aralkyl group wherein the aryl and alkyl portions of the group have the meanings given above;

$R_5$ is selected from the group consisting of O, S and NH; and $R_7$, $R_8$ and $R_9$ each are independently selected from:
hydrogen, a $C_1$–$C_{20}$ alkyl group, an aryl group which is a substituted or unsubstituted phenyl or heterocyclic group, and an aralkyl group wherein the aryl and alkyl portions of the groups have the meanings given above;
a glycosyl group wherein said glycosyl group is selected from the group consisting of ribosyl, 2'-deoxyribosyl, 2',3'-dideoxy-3'-azidoribosyl, 2',3'-dideoxy-2'-fluororibosyl, 2',3'-dideoxy-3'-fluororibosyl, 2',3'-dideoxy-2',3'-difluororibosyl, and mono-, di- and triphosphate derivatives thereof; and
$(CH_2)_m$—XR'—$(CH_2)_n$—YR' wherein R' is selected from the group consisting of:
H, $H_2$, $H_2PO_3$, $H_3P_2O_6$, $H_4P_3O_9$, and alkali metal or alkaline earth metal salts thereof;
m is zero to 20, n is zero to 20 and a is zero or one; and
U, X, Y, Z, W, J, K, and L are selected from the group consisting of C, N, O, P, and S.

Furthermore, it must be noted that the present invention includes all chiral forms and stereoisomers of the compounds presented above.

Additionally, the present invention includes non-planar, non-aromatic, ring-expanded ("fat") heterocyclic bases, nucleosides or nucleotides having the following formulas III and IV:

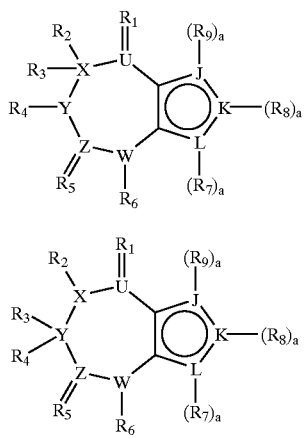

Formula III

Formula IV wherein:
R$_1$ and R$_5$ are each independently selected from O, S, and NH;

R$_3$ and R$_4$ are each independently selected from H, OR$_2$, SR$_2$, NHR$_2$, CO$_2$R$_2$, CONHR$_2$, CONHNHR$_2$, CH$_2$OR$_2$, CH$_2$NHR$_2$, and CH$_2$R$_2$;

R$_2$, R$_4$ and R$_6$ are each independently selected from:
hydrogen, a C$_1$–C$_{20}$ alkyl group, an aryl group which is a substituted or unsubstituted phenyl or heterocyclic group, and an aralkyl group wherein the aryl and alkyl portions of the group have the meanings given above;

R$_7$, R$_8$, and R$_9$ are each independently selected from:
hydrogen, a C$_1$–C$_{20}$ alkyl group, an aryl group which is a substituted or unsubstituted phenyl or heterocyclic group, and an aralkyl group wherein the aryl and alkyl portions of the groups have the meanings given above;

a glycosyl group wherein said glycosyl group is selected from the group consisting of ribosyl, 2'-deoxyribosyl, 2',3'-dideoxy-3'-azidoribosyl, 2',3'-dideoxy-2'-fluororibosyl, 2',3'-dideoxy-3'-fluororibosyl, 2',3'-dideoxy-2',3'-difluororibosyl, and mono-, di-, and triphosphate derivatives thereof;

(CH$_2$)$_m$—XR'—(CH$_2$)$_n$—YR' wherein R' is selected from:
hydrogen, H$_2$PO$_3$, H$_3$P$_2$O$_6$, H$_4$P$_3$O$_9$, and alkali metal or alkaline earth metal salts thereof;
m is zero to 20, n is zero to 20, and a is zero or one; and U, X, Y, Z, W, J, K, and L are selected from the group consisting of C, N, O, P, and S.

The compositions relating to formulas (II), (III) and (V) may also contain a pharmaceutically acceptable carrier.

Furthermore, it must be noted that the present invention includes all chiral forms and stereoisomers of the compounds presented above.

The synthesis of all compounds start from the common starting material 5-nitroimidazole-4-carboxylic acid that may or may not be substituted at the 1-, 2-, or 3-position. The acid group can be converted into an activated ester, normally by treatment with 1,1'-carbonyldiimidazole (CDI), 1,3-dicyclohexylcarbodiimide (DCC), or N-hydroxysuccinimide. The activated ester can be further condensed with an anion of, for example, nitromethane (Formula II), an anion of, for example, dimethyl or diethyl nitromalonate (Formula III), or, for example, dimethyl or diethylaminomalonate (Formula IV). Catalytic reduction of the two nitro groups of the product of the above nitromethane condensation, using a reagent such as tin chloride, followed by base-catalyzed ring-closure can give the 5:7-fused heterocyclic precursors of compounds of general Formula II. Subsequent reduction of these dicarbonyl precursors with a reagent, for example, sodium borohydride can specifically reduce the keto carbonyl while leaving the ureido carbonyl group intact, thus affording the desired compounds of general formula II.

With respect to compounds of general Formula III, the product of the above dialkyl nitromalonate condensation can be subjected to sequential hydrolysis, decarboxylation, and re-esterification to obtain 2-alkoxycarbonyl-2-(5-nitroimidazolyl-4-carbonyl)nitromethane derivatives. The activated methane group of the side chain can now be exploited to introduce a leaving group such as bromide which can be subsequently converted into an alkoxy group. Catalytic reduction of the two nitro groups, followed by ring-closure, in a manner analogous to the one described above for Formula II, can afford the 5:7-fused heterocyclic precursors of Formula III. In the final step, the alkoxy group can be hydrolyzed to the corresponding hydroxy group to afford the desired compounds of general Formula III. The methodology to be used for compounds of Formula IV is very similar to that of Formula III except that the initial condensation product has a carbonylaminomalonate side chain. The procedures to be employed for the preparation of alkyl, aryl and nucleoside/nucleotide derivatives are analogous to the ones described above for compounds of general Formula I.

The compounds of the present invention exhibit antiviral activity with acceptable levels of cytotoxicity and can thus be used either singly or in combination to maximize therapeutic effectiveness in the treatment of viral, bacterial, fungal, parasitic or other infections. Viruses contemplated to be within the broad scope of treatment of the present invention include, but are not limited to, the following: Human Immunodeficiency virus (HIV), Human B lymphotropic virus, Herpes simplex virus, Varicella-zoster virus, Epstein-Barr virus, necrotic rhinitis, Malignant catarrh, Allerton virus, Equine herpesviruses, Neurolymphomatosis, Influenza viruses, Parainfluenza viruses, Adenoviruses, Rheovirus, Respiratory syncytial virus, Rhinoviruses, Coxsackie virus, Echo viruses, Epidemic gastroenteritis virus, Rubeola virus, Hepatitis viruses, and Papovavirus.

Figure 14:
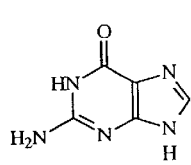
Figure 14:
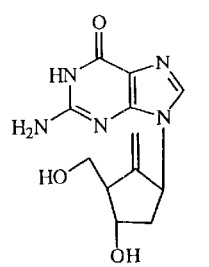
Figure 14:
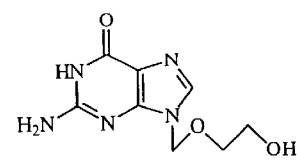
Figure 14:
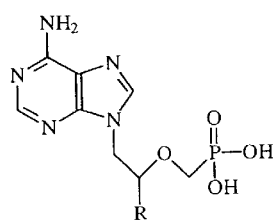
Figure 14:
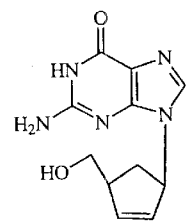
Figure 14:
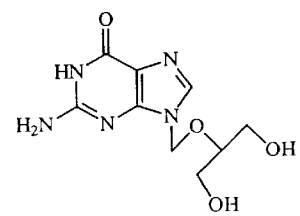

The ring-expanded nucleosides described in this application are analogs of naturally occurring purine nucleosides such as guanosine and adenosine. A guanosine aor adenosine analog may have the addition of extra carbonyl, amino or imino group(s) to the expanded ring of guanosine and adenosine. Several nucleosides derived from guanine and adenine base have shown antiviral activities against several viruses (E. De Clercq. Advances In Virus research. 42. 1–55, 1993). Choice of the substituent attached at position N-9 of the purine heterocycle seems to play a major role in the specificity of the antiviral activity. For example, in the guanine based nucleosides, a carbocyclic guanosine analog (see FIG. 14) with an exocyclic methylene group, BMS 200475, is selectively active in inhibiting replication of Hepatitis B virus (HBV) (S. F. Innaimo et al. Antimicrob. Agents Chemother. 41, 1444–1448, 1997). This compound has no activity against other viruses such as Herpes viruses (HSV, CMV, VZV, or EBV) or reteroviruses such as human immunodeficiency virus (HIV). On the other hand, replacement of cyclic substituents from N-9 of guanine with the acyclic groups as in case of aciclovir and ganciclovir impart these molecules antiviral activity against HSV and CMV, respectively, (E. De Clercq Advances In Virus research. 42. 1–55 , 1993) with no activity against HBV (B. E. Korba et al, Antimicrob. Agents Chemother. 40, 1282–1284, 1996). Another carbocyclic analog of dideoxy guanosine, carbavir, where N-9 substituent on guanine heterocycle is cyclopentenyl moiety has been shown to possess very potent activity against HIV (E. De Clercq Advances In Virus research. 42. 1–55 , 1993). Similarly in the adenine based analogs, [s]-9-(3-hydroxy-2-phosphonylmethoxypropyl)adenine (HPMPA) is inactive against HIV. Strong inhibition of HIV replication by 9-(2-phosphonylmethoxy)adenine was achieved by removal of the hydroxymethyl group from the side chain of HPMPA (L. Naesens et al, Antiviral Chem. Chemother. 8, 1–23, 1997). These examples show that nature of the substituent on the N-9 position of these heterocycles plays a major role in determining the specificity of the antiviral activity of nucleoside analogs and antiviral activity spectrum of purine nucleoside analogs can be altered by modifying the sugar substituent on the purine heterocyclic ring.

The compounds of the present invention are ring-expanded analogs of guanine or adenine. The change of sugar residue on the guanine or adenine base in nucleosides can markedly alter the antiviral activity spectrum of nucleosides. Since the compounds of the present invention are ring-expanded versions of adenine or guanine containing nucleosides and they show antiviral and antitumor activities like these compounds (unexpanded-ring versions of guanine or adenine base), one would expect similar changes in the antiviral activity spectrum of other analogs (to show activity against other viruses) due to change of the sugar substituent.

In vitro anti-HBV activity of nucleosides is a predictor of their activity in woodchuck animal model and in humans. Several relevant and predictive animal models of HBV induced infection and disease, including hepatocellular carcinoma, such as the woodchuck hepatitis virus (WHV) and its natural host, the eastern woodchuck, have been developed (J. L. Gerin et al, Cancer Prevention and Detection. 14, 227–229, 1989). Determination of potential usefulness of newly developed therapeutic agents against HBV using these animal models is complicated by the prolonged treatment periods that are required to induce substantial reductions in the viral replication in animals, the standardization of pharmacokinetic parameters in the animals and the associated cost of conducting these experiments and maintaining these animals.

Cell culture based assays have been used to evaluate anti HBV activities of new compounds (B. E. Korba et al., Antiviral Res. 15, 217–228, 1991; and 19, 55–70, 1992). Extracellular levels of HBV virion DNA and intracellular viral DNA replication intermediates (RI) in the cell-culture based assays are most reliable markers of HBV replication. The inhibitory activities of several test compounds against HBV virion DNA and intracellular HBVDNA RI in the cell-culture system used to evaluate the present compounds have been shown to accurately model the inhibitory activities of these compounds against hepadaviruses when administered to chronic viral carriers (B. E. Korba et al., Antiviral Res. 15, 217–228, 1991; E. Lin et al., Antimicrob. Agents Chemother. 42, 2132–2137, 1998; E. V. Genovesi et al., Antimicrob. Agents Chemother. 42, 3209–3217, 1998). Moreover, 3'-thiacytidine (3TC), which has shown activity against HBV in the cell culture assay, has been proven efficacious in humans and has been approved in the United States and other parts of the world for treating chronic HBV infections in humans.

The compounds of the present invention can be administered for the treatment of any disease or any applicable medical or non-medical condition by any means that effects contact of the active ingredient compound with the site of action in the body of a warm-blooded animal or cold-blooded animal, plant (for agricultural uses), or lower forms of life (i.e., invertebrates, bacteria, single-celled organisms, and cell or tissue culture, among others). For the purpose of this disclosure, a warm-blooded animal is a member of the animal kingdom having a homeostatic mechanism and includes, for example, mammals and birds. For example, administration can be parenteral, i.e., subcutaneous, intravenous, intramuscular, or intraperitoneal. Alternatively, or concurrently, in some cases, administration can be by the oral or topical route.

The compounds of this invention are suitable for treating dermatological complaints relating to viral, bacterial, fungal, immunologic, and/or keratinization disorders (e.g., differentiation—proliferation disorders, including psoriasis). The topical compositions are advantageously in the form of ointments, salves, tinctures, creams, emulsions, solutions, lotions, sprays, powders, gels, suspensions, patches or saturated pads. The compounds are mixed with inert, nontoxic, generally liquid or pasty bases which are suitable for treatment by a topical route with concentrations of active compound(s) ranging from 0.0005% to 5% by weight. It is possible, of course, to employ higher concentrations when this is required for a particular therapeutic application; however, the preferred concentrations of active compound(s) are from 0.002 to 1% by weight. When the compound(s) of the invention are administered by an ocular route, they are advantageously presented in the form of a solution or a powder to be diluted to give an eye lotion.

Certain compounds which are encompassed by the present invention are metabolic inhibitors and can be administered with anti-tumor and/or anti-viral agents to potentiate their action by inhibiting adenosine deaminase and/or guanase enzymes. The compounds can be administered with antiviral agents in ratios of from about 0.005 to about 0.5 parts of the compound to about 1 part of antiviral agent. The pharmaceutical composition can be in bulk form or in aqueous solution with other materials such as preservatives, buffering agents, agents intended to adjust the osmolality of the solution, etc.

From a medicinal standpoint, the compounds of the present invention can also be regarded as analogues of the well-studied benzodiazepines and benzotriazepines, a family of powerful pharmaceuticals (e.g., valium) acting on the central nervous system (Coffen et al., *J. Org. Chem.* 49:296 (1984) and references cited therein), and may also be shown to act by binding to purine receptors, regulating ion channels, affecting synaptic vesicle trafficking, and nerve signal transduction. (Recently benzodiazepine analogues have become the focus of attention because of their ability to block mutated ras genes from making cells cancerous (Travis, *Science* 260:1877 (1993); James et al., *Science* 260:1937 (1993).) In this regard, it is important to note that the recently reported and potent inhibitors of HIV reverse transcriptase belonging to the TIBO family of heterocycles contain the basic imidazobenzodiazepine nucleus (Pauwels et al., *Nature* 343:470 (1990)), which can be extended to include tricyclic analogues of the present compound. The imidazobenzodiazepine compounds are thought to be several-fold more potent and less toxic than AZT for the growth inhibition of HIV-1 (Liaw et al., *J. Am. Chem. Soc.* 113:1857 (1991). A benzodiazepine analogue has also been recently reported to be a powerful anti-Tat agent capable of blocking HIV replication in both acutely and chronically infected HIV-infected cells (Hsu et al., Science 254:1799 (1991)).

The compounds of the invention can be administered by any conventional means available for use in conjunction with pharmaceuticals, either as individual therapeutic agents or in a combination of therapeutic agents. They can be administered alone, but are generally administered with a pharmaceutically acceptable carrier selected on the basis of the chosen route of administration and standard pharmaceutical practice.

The dosage administered will be dependent on the age, health and weight of the recipient, the extent of disease, kind of concurrent treatment, if any, frequency of treatment, and the nature of the effect desired. Usually, a daily dosage of active ingredient compound will be from about 1–1000 milligrams per day. Ordinarily, from 10 to 500 milligrams per day in one or more applications is effective to obtain the desired results.

The active ingredient of the present invention can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules can contain the active ingredient and powdered carriers, such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration and/or respiratory inhalants preferably contain a water soluble salt of the active ingredient, suitable stabilizing agents, and if necessary buffer substances. Antioxidizing agents such a sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propylparaben, and chlorbutanol.

Suitable pharmaceutical carriers are described in Remington's Pharmaceutical Sciences, A. Osol, Mack Publishing Co., Easton, Pa. (1990), a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of lactose, 50 milligrams of cellulose, and 6 milligrams of magnesium stearate.

Soft Gelatin Capsules

A mixture of active ingredient in a digestible oil such as soybean oil, cottonseed oil or olive oil is prepared and injected by means of a positive displacement pump into gelatin to form gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.25 milliliters of vanillin.

Cosmetic

The present invention also provides a cosmetic composition containing, in a cosmetically acceptable carrier, at least one compound, or its salts or isomers, the composition being, in particular, in the form of a lotion, gel, cream, soap or shampoo.

Veterinary

The compound of the invention may also be presented for use in the form of veterinary formulations prepared by conventional methods in the art. Examples of such veterinary formulations include those adapted for oral administration (drenches of aqueous or non-aqueous solutions or suspensions), tablets, boluses, powders, granules, or pellets (for feed admixtures), or pastes for application to the tongue. Other examples of such veterinary formulations include those adapted for parenteral administration (by subcutaneous, intramuscular, or intravenous injection as a sterile solution or suspension or by intramammary injections in which a solution or suspension is introduced into the udder via the teat); topical application (as a cream, ointment, dip or spray applied to the skin); or intravaginally (as a pessary, cream, or foam).

In addition to the ingredients mentioned above, including compounds of the present invention, the formulations of the invention may include other agents convention in the art in reference to the type of formulation, e.g., those suitable for oral administration may include such further agents such as sweeteners, flavoring agents, thickeners, etc. The formulations of the invention for human or veterinary use may be presented in unit-dose or multi-dose sealed containers (ampoules and vials) and may be stored in a lyophilyzed or freeze-dried form requiring the addition of a sterile liquid carrier for reconstitution immediately prior to use.

EXPERIMENTAL EXAMPLES

The present invention can be illustrated by the use of the following non-limiting examples:

Example 1

4,8-Diamino-6-imino-1H-imidazo[4,5-e][1,3]diazepine

[Formula I(B), Where U, Y, W, K=C; X, Z, J, L=N; $R_1$, $R_5$=$NH_2$, $R_3$=NH; $R_2$, $R_4$, $R_6$=None; and $R_7$, $R_8$=H]

Method A: By Condensation of 4,5-Dicyanoimidazole With Guanidine:

Guanidine was liberated from guanidine hydrochloride (1.15 g, 12 mmol) by addition of a freshly prepared solution of sodium methoxide in methanol from sodium (0.28 g, 12 mmol), and stirring with ice-water cooling for 30 minutes. The precipitated sodium chloride was filtered off, and the filtrate was added to the solution of 4,5-dicyanoimidazole (1.18 g, 10 mmol) in methanol (25 mL). The reaction mixture was heated to reflux for 20 hours and cooled to room temperature. The solid separated was collected by filtration, and recrystallized from methanol. Yield 1.15 g (65%), mp>220° C.: $^1$H NMR (DMSO-$d_6$) δ 7.75 (s, 2 H, $NH_2$, exchangeable with $D_2O$); 7.65 (s, 2H, $NH_2$, exchangeable with $D_2O$), 7.53 (s, 1H, imidazole CH), 6.98 (s, 2H, two NH, exchangeable with $D_2O$); $^{13}$C NMR (DMSO-$d_6$) δ 164 (C=NH), 160 (C=N), 150 (C=C), 136.5 (imidazole CH); IR (KBr) 3300, 3010 $cm^{-1}$.

Anal. Calcd. for $C_6H_7N_7$: C, 40.68; H, 3.98; N, 55.34. Found: C, 40.67; H, 4.02; N, 55.28.

Method B: By Debenzylation of 4,8-Diamino-1-benzyl-6-iminoimidazo[4,5-e][1,3]diazepine

[Formula I(B), where U, Y, W, K=C; X, Z, J, L=N; $R_1$, $R_5$=$NH_2$; $R_3$=NH; $R_2$, $R_4$, $R_6$=None; and $R_7$=H; $R_8$=$CH_2Ph$]: 4,8-Diamino-1-benzyl-6-iminoimidazo[4,5-e][1,3]diazepine (0.54 g, 2 mmol) was dissolved in glacial acetic acid (15 mL) in a hydrogenation bottle. Palladium hydroxide on carbon (20%, 80 mg) was added to the above solution, and the mixture was hydrogenated in a Parr hydrogenator at 40 psi for 16 hours. The catalyst was removed by filtration through Celite, and was washed with acetic acid (5 mL). The filtrate, along with the washings, was evaporated to dryness under reduced pressure to obtain a colorless residue. The residue was dissolved in cold water, filtered, and the filtrate was evaporated under reduced pressure. The resulting white solid was recrystallized from water. Yield 0.2 g, 56%.

The spectral and analytical data of this compound were consistent with those of the compound obtained above by Method A.

Example 2

6-Imino-1H-imidazo[4,5-e][1,3]diazepine-4,8-dione

[Formula I(A), Where U, Y, W, K=C; X, Z, J, L=N; $R_1$, $R_5$=O; $R_3$=NH; $R_2$, $R_4$, $R_6$, $R_7$=H; $R_8$=None]

(a) 4,5-Imidazolediformyl Chloride: 4,5-imidazoledicarboxylic acid (2.0 g, 12.8 mmol) was placed in a flame-dried three-necked, round-bottomed flask, fitted with a $CaCl_2$ guard tube. Thionyl chloride (10 mL, 0.137 mol) was introduced through a serum cap, and the reaction mixture was heated at 50° C. with continuous stirring for 24 hours. The reddish-yellow reaction mixture was rotary evaporated to dryness under anhydrous conditions, and the residue was coevaporated to dryness with dry toluene (3×10 mL). The resultant residue was employed for the next step given below without further purification.

(b) 6-Imino-1H-imidazo[4,5-e][1,3]diazepine-4,8-dione: Guanidine was liberated from guanidine hydrochloride (0.955 g, 10 mmol) by addition of a freshly prepared solution of sodium methoxide in methanol from sodium (0.23 g, 10 mmol), and stirring with ice-water cooling for 30 minutes. The precipitated sodium chloride was filtered off, and the filtrate was added to the solution of 4,5-imidazolediformyl chloride, prepared from the above step, in methanol (20 mL). The reaction mixture was heated to reflux for 20 hours and cooled to room temperature. The solid separated was collected by filtration, and recrystallized from water. Yield 1.7 g (79%) mp>220° C.: $^1$H NMR (DMSO-$d_6$) δ 7.68 (s, 1H, imidazole CH), 7.02 (br s, 4H, four NH, exchangeable with $D_2O$); $^{13}$C NMR (DMSO-$d_6$) δ 164 (C=O), 158.5 (C=NH), 137 (C=C), 133 (imidazole CH); IR (KBr) 3470, 3400, 3200, 3090, 1720, 1680, $cm^{-1}$.

The compound gave positive test with 1M $AgNO_3$ solution, precipitating AgCl, indicating that the compound was a hydrochloride salt.

Anal. Calcd. for $C_6H_5N_5O_2$·$2H_2O$: C, 33.46; H, 4.18; N, 32.54 Found: C, 33.49; H, 4.23; N, 32.47.

Example 3

4,8-Diamino-1-benzyl-6-iminoimidazo[4,5-e][1,3]diazepine

[Formula I(B), Where U, Y, W, K=C; X, Z, J, L=N; $R_1$, $R_5$=$NH_2$; $R_3$=NH; $R_2$, $R_4$, $R_6$=None; $R_2$=H; and $R_8$=$CH_2Ph$]

(a) 1-Benzyl-4,5-dicyanoimidazole: 4,5-Dicyanoimidazole (5.0 g, 42 mmol) was placed in a 250-mL three-necked, round-bottomed flask, equipped with a magnetic stirrer, a reflux condenser, a thermometer, and a $CaCl_2$ guard tube. The solid was dissolved by addition of dimethylformamide (100 mL) with stirring. Anhydrous potassium carbonate (7.5 g, 54 mmol) was added slowly while stirring, followed by the addition of benzyl chloride (6.2 mL, 53 mmol), and the mixture was stirred at room temperature overnight. Then, the reaction mixture was heated to 75° C. and was allowed to stir at that temperature for 20 hours. The reaction mixture was cooled to room temperature, filtered to remove inorganic salts, and the filtrate was rotary evaporated to dryness. The residue was cooled in an ice-water bath, and the light yellow solid that separated was recrystallized from benzene. Yield 5.6 g (64%), mp 123–125° C.: $^1$H NMR (DMSO-$d_6$) δ 8.57 (s, 1H, imidazole CH), 7.46–7.30 (m, 5H, Ph-H), 5.52 (s, 2H, $CH_2$); $^{13}$C NMR (DMSO-$d_6$) δ 145 (imidazole CH), 135 (i-C of Ph), 130 (o-C of Ph), 129 (p-C of Ph), 128 (m-C of Ph), 124 (C=C), 113 (C=C), 114 (CN), 109 (CN), 51 ($CH_2$); IR (KBr) 3100, 3020, 2200, 1560–1400, 1108, 902, 840, 800, 720, 690 $cm^{-1}$; UV (MeOH) $\lambda_{max}$ 246, 207 nm.

(b) 4,8-Diamino-1-benzyl-6-iminoimidazo[4,5-e][1,3]diazepine: Guanidine hydrochloride (1.15 g, 12 mmol) was added to a solution of sodium methoxide, freshly prepared by dissolving clean sodium metal (0.28 g, 12 mmol) in absolute methanol, and the mixture was stirred in an ice-water bath for 30 minutes. The precipitated sodium chloride was filtered off, and the filtrate was poured into a portion of the solution of 1-benzyl-4,5-dicyanoimidazole prepared above (2.08 g, 10 mmol) in 25 mL of methanol. The reaction mixture was heated to reflux for 20 hours, cooled to room temperature and the precipitated solid was then collected by filtration and recrystallized from methanol. Yield 2.11 g (79%), mp 202–204° C.: $^1$H NMR (DMSO-$d_6$) δ 8.12 (s, 1H, imidazole CH), 7.32–7.20 (m, 9H, five Ph-H+two $NH_2$, exchangeable with D$_2$O), 5.83 (s, 2H, CH$_2$); $^{13}$C NMR (DMSO-d$_6$) δ 158.2 (C=NH), 158.1 (C=N), 157.5 (C=N), 141.5 (imidazole CH), 139 (i-C of Ph), 133.2 (C=C), 133.0 (C=C), 129.5 (o-C of Ph), 128.4 (p-C of Ph), 128.2 (m-C of Ph); IR (KBr) 3320, 3200, 1650, 1580, 1520, 1500, 1420, 1380, 900, 870 cm$^1$.

Anal. Calcd. for C$_{13}$H$_{13}$N$_7$: C, 58.42; H, 4.90; N, 36.68. Found: C, 58.51; H, 4.89; N, 36.58.

Example 4

4,6,8-Triimino-1-β-D-ribofuranosylimidazo[4,5-e][1,3]diazepine

[Formula I(A), where U, Y, W, K=C; X, Z, J, L=N; R$_1$, R$_3$, R$_5$=NH; R$_2$, R$_4$, R$_7$=H; R$_6$=1-β-D-Ribofuranosyl; and R$_8$=None]

Method A: By Condensation of 4,5-Dicyano-1-β-D-ribofuranosylimidazole with Guanidine:

(a) 1-(2,3,5-Tri-O-benzoyl-β-D-ribofuranosyl)-4,5-dicyanoimidazole: A solution of 4,5-dicyanoimidazole (354 mg, 3.0 mmol) and 1-O-acetyl-2,3,5-tri-O-benzoyl-β-D-ribofuranose (1.51 g, 3 mmol) in acetonitrile (30 mL) was charged to a flame-dried, three-necked, 50-mL round-bottomed flask, equipped with a refluxing condenser, a magnetic stirrer, and a N$_2$ gas inlet. The solution was stirred in an ice-water bath for 5 minutes. Freshly distilled hexamethyldisilazane (HMDS) (0.7 mL, 3.3 mmol), freshly distilled chlorotrimethylsilane (CTMS) (0.45 mL, 3.6 mmol), and trifluoromethanesulfonic acid (TFMSA) (0.3 mL, 3.6 mmol) were consecutively added to the above solution. The resulting solution was stirred in an ice-water bath for 30 minutes. The reaction, as monitored by TLC (silica gel, toluene:acetic acid:water =5:5:1), showed complete conversion to the product in 30 minutes. Methylene chloride (30 mL) was added to the reaction mixture and was extracted with saturated aqueous NaHCO$_3$. The organic layer was separated, and the aqueous layer was once again extracted with CH$_2$Cl$_2$ (10 mL). The combined organic extracts were washed with saturated aqueous NaCl, dried over anhydrous MgSO$_4$, filtered, and the filtrate was evaporated to dryness under reduced pressure to obtain a foam.

Yield 1.5 g (94%), mp 68–72° C.: $^1$H NMR (DMSO-d$_6$) δ 8.68 (s, 1H, imidazole CH), 7.92 (m, 5H, Ph-H), 7.63 (m, 5H, Ph-H), 7.40 (m, 5H, Ph-H), 6.63 (d, J=4.8 Hz, 1H, H-1'), 6.06 (t, J=5.1 Hz, 1H, H-2'), 5.99 (t, 1H, H-3'), 4.97 (q, 1H, H-4'), 4.74 (dd, 2H, H-5'); $^{13}$C NMR (DMSO-d$_6$) δ 163 (C=O), 161 (C=O), 160.5 (C=O), 142.6 (imidazole CH), 135 (Ph-C), 134.8 (Ph-C), 134.4 (Ph-C), 130.4 (Ph-C), 130.2 (Ph-C), 130.0 (Ph-C), 129.8 (Ph-C), 129.7 (Ph-C), 129.5 (Ph-C), 129.4 (Ph-C), 129.3 (Ph-C), 129.0 (Ph-C), 124 (C=C), 113 (C≡N), 111.7 (C≡N), 109.2 (C=C), 89.8 (C-1'), 81.8 (C-2'), 75.5 (C-3'), 71.5 (C-4'), 64.2 (C-5').

Anal. Calcd. for C$_{31}$H$_{22}$N$_4$O$_7$: C, 66.19; H, 3.94; N, 9.96. Found: C, 66.20; H, 3.96; N, 9.76.

(b) 4,6,8-Triimino-1-β-D-ribofuranosylimidazo[4,5-e[1,3]diazepine: 1-(2,3,5-Tri-O-benzoyl-β-D-ribofuranosyl)-4,5-dicyanoimidazole (2.0 g, 3.5 mmol) was added to a cold solution of sodium methoxide solution freshly prepared by dissolving sodium metal (2.0 g, 86.95 mg.atom) in 50 mL of methanol. Guanidine hydrochloride (3.5 g, 36 mmol) was then added. The reaction mixture was heated at reflux overnight. A tlc of the reaction mixture (silica gel, CHCl$_3$:MeOH, 4:1) indicated complete consumption of the starting material and the presence of a new, UV-absorbing spot which had a lower Rf than the starting material. The reaction mixture was cooled and acidified to pH 6.5 with 1N HCl. The solution was mixed with flash silica gel (4 g, particle size 40–63 μm) and rotary evaporated to dryness. The silica gel-adsorbed compound was purified by flash chromatography on a column of flash silica gel of the same particle size as above. Elution with a mixture of CHCl$_3$:MeOH (4:1) removed most of the impurities present. The column was then eluted with methanol alone, and the appropriate UV-absorbing fractions were pooled and evapored to afford a solid which was recrystallized from 2-propanol to give white powder. Yield 0.45 g (40%), mp>200° C.: $^1$H NMR (DMSO-d$_6$) δ 8.76 (br s, 1H, exchangeable with D$_2$O, NH), 8.60 (s, 1H, imidazole CH), 8.56 (s, 1H, exchangeable with D$_2$O, NH), 8.46 (s, 1H, exchangeable with D$_2$O, NH), 8.20 (s, 1H, exchangeable with D$_2$O, NH), 8.17 (s, 1H, exchangeable with D$_2$O, NH), 6.35 (br s, 1H, exchangeable with D$_2$O, ribose OH), 6.0 (d, 1H, J=6.3 Hz, anomeric H), 5.43 (d, 1H, J=4.5 Hz, exchangeable with D$_2$O, ribose OH), 5.25 (t, 1H, J=5.4 Hz, exchangeable with D$_2$O, ribose OH), 4.35 (t, 1H, H-2'), 4.06 (m, 2H, H-3' and H-4'), 3.64 (m, 2H, H-5'); $^{13}$C NMR (DMSO-d$_6$) δ 163.94 (C=N), 157.79 (C=N), 152.16 (C=N), 140.52 (C=C), 138.13 (C=N), 126.58 (C=C), 89.31 (ribose C), 87.41 (ribose C), 76.27 (ribose C), 70.65 (ribose C), 61.03 (ribose C); MS (FAB) 310 (MH$^+$).

Anal. Calcd. for C$_{11}$H$_{15}$N$_7$O$_4$.2HCl: C, 34.71; H, 4.47; N, 25.77. Found: C, 34.87; H, 4.54; N, 25.70.

Method B: By Ribosylation of 4,8-Diamino-6-imino-1H-imidazo[4,5-e][1,3]diazepine (a) 1-(2,3,5-Tri-O-benzoyl-β-D-ribofuranosyl)-4,6,8-triiminoimidazo[4,5-e][1,3]diazepine. 4,8-diamino-6-imino-1H-imidazo[4,5-e][1,3]diazepine (see Example 1 above) (1.0 g, 5.6 mmol) was placed in a dry, three-necked, round-bottomed flask, fitted with a reflux condenser and a N$_2$ gas inlet. Bis(trimethylsilyl) trifluoroacetamide (BSTFA) (13.5 g, 52 mmol) was added, and the reaction mixture was heated at reflux for 2.5 hours, at which time a clear solution was formed. The solution was cooled to room temperature and evaporated to dryness in vacuo using a Kugelrohr apparatus. The residue was suspended in dry acetonitrile (50 mL), and the reaction mixture was kept at −42° C. using an acetonitrile-dry ice bath. 1-O-Acetyl-2,3,5-tri-O-benzoyl-β-D-ribofuranose (2.84 g, 5.6 mmol) was added to the reaction mixture, followed by trimethylsilyl trifluoromethanesulfonate (TMS triflate) (1.4 mL, 6.9 mmol). The reaction mixture was slowly allowed to come to 0° C. The reaction mixture was poured into 200 mL of methylene chloride and washed with 100 mL of water. The organic layer was separated and dried over anhydrous magnesium sulfate. Evaporation of the solvent afforded a residue which was triturated with 2-propanol to form a foam. An analytical sample of the foam was prepared by using diethyl ether. Yield 4.1 g (94%): $^1$H NMR (DMSO-d$_6$) δ 8.74 (s, 1H, imidazole CH), 8.58 (s, 1H, NH, exchangeable with D$_2$O), 8.52 (s, 1H, NH, exchangeable with D$_2$O), 8.21 (br s, 1H, NH, exchangeable with D$_2$O), 7.77 (m, 16H, three Ph+one NH exchangeable with D$_2$O), 6.78 (d, J=3.0 Hz, 1H, anomeric H), 6.22 (t, J=3.9 Hz, 1H, ribose CH), 6.0 (t, 1H, ribose CH), 4.93 (m, 1H, ribose CH), 4.69 (m, 2H, H-5').

Anal. Calcd. for C$_{32}$H$_{27}$N$_7$O$_7$.CF$_3$SO$_2$OH: C, 51.32; H, 3.62; N, 12.70. Found: C, 51.68; H, 3.87; N, 12.70.

(b) 4,6,8-Triimino-1-β-D-ribofuranosylimidazo[4,5-e][1,3]diazepine. To a solution of sodium methoxide that was freshly prepared by dissolving cleanly cut sodium metal (100 mg, 4.3 g.atom) in 100 mL of methanol, was added 1-(2,3,5-tri-O-benzoyl-β-D-ribofuranosyl)- 4,6,8 - triiminoimidazo[4,5-e][1,3]diazepine, prepared above (1.5 g, 1.94 mmol), at −42° C., using dry ice-acetonitrile bath. The compound dissolved slowly, and the temperature was gradually raised to 0° C. The reaction mixture was stirred at 0° C. for 4 hours when a tlc (silica gel, CHCl$_3$:MeOH, 4:1) indicated no starting material. The reaction mixture was neutralized with 1N HCl to pH 6–6.5, followed by evaporation to dryness on a rotary evaporator. The solid residue was extracted with a mixture of EtOH and MeOH (1:1), filtered, and the filtrate was evaporated to dryness. The residue was dissolved in about 3 mL of water, and to the solution was added 2-propanol when a white solid separated. The solid was filtered and was recrystallized from a mixture of 2-propanol water into colorless granules. Yield 0.68 g (92%), mp>200° C. The spectral and analytical data of this compound were consistent with those of 4,6,8-triimino-1-β-D-ribofuranosylimidazo[4,5-e][1,3]diazepine, prepared by Method A above.

Example 5

4,5,6,7-Tetrahydro-8-hydroxy-8H-1-β-D-ribofuranosylimidazo[4,5-d][1,3]diazepine-5-one

[Formula II, Where U, X, Z, K=C; Y, W, J, L=N; R$_1$=OH; R$_2$, R$_4$, R$_6$, R$_8$=H; R$_3$=H$_2$; R$_7$=None; R$_9$= 1-β-D-Ribofuranosyl]

(a) 2-Amino-1-(1-benzyl-5-amino-1H-imidazol-4-yl)ethanone: 2-Amino-1-(1-benzyl-5-amino-1H-imidazol-4-yl)ethanone dihydrochloride (Baker et al., *J. Org. Chem.* 47:3457 (1982)) (900 mg, 3.0 mmol) was dissolved in H$_2$O (20 mL), and the solution was cooled in an ice-water bath. Aqueous NaOH solution (2N) was added dropwise with constant stirring until the pH of the solution reached 13–14. The solution was extracted with EtOAc (3×25 mL), and the combined extracts were dried over anhydrous MgSO$_4$. Filtration, followed by rotary evaporation of the filtrate under reduced pressure, gave a solid which was recrystallized from toluene as pale yellow crystals. Yield 400 mg (60%), mp 156–162° C.: $^1$H NMR (Me$_2$SO-d$_6$) δ 7.26 (m, 6H, Ph-H+imidazole CH), 6.5 (s, 2H, exchangeable with D2O, NH$_2$ aromatic), 5.09 (s, 2H, benzyl CH$_2$), 3.69 (s, 2H, side-chain CH$_2$), 1.7 (br s, 2H, exchangeable with D$_2$O, NH$_2$ aliphatic); IR (KBr) 3400, 3360, 3260, 3100, 1650 cm$^{-1}$; mass spectrum (70 eV) m/z 230 (M$^+$), 201, 173, 91; UV (MeOH) 297 nm, (pH 13) 297.

Anal. Calcd. for C$_{12}$H$_{14}$N$_4$O: C, 62.61; H, 6.10; N, 24.35. Found: C, 63.22; H, 6.15; N, 23.26.

(b) 3-Benzyl-4,5,6,7-tetrahydro-8H-imidazo[4,5-d][1,3]diazepine-5,8-dione: A mixture of the above 2-amino-1-(1-benzyl-5-amino-1H-imidazol-4-yl)ethanone (322 mg, 1.4 mmol) and dry CH$_3$CN (30 mL) was warmed under N$_2$ in a three-necked flask, fitted with a reflux condenser and a guard tube, to form a clear solution. p Nitrophenyl-chloroformate (297 mg, 1.47 mmol) was added, whereupon a white solid separated. After addition of triethylamine (0.32 mL, 28.7 mmol), the white solid dissolved to give a clear solution. The solution was stirred at reflux for 5 hours when most of the title compound separated as a solid. The reaction mixture was cooled and the solid obtained was collected by filtration and was washed with cold CH$_3$CN, followed by Et$_2$O. The solid was recrystallized from EtOH as colorless crystals. Yield 210 mg (59%), mp 214° C. dec.: $^1$H NMR (Me$_2$SO-d$_6$) δ 9.79 (s, 1H, exchangeable with D$_2$O, NH-4), 7.63 (s, 1H, imidazole CH), 7.3 (m, 6H, Ph-H+NH-6, exchangeable with D$_2$O), 5.36 (s, 2H, benzyl CH$_2$), 3.65 (d, J=4.9 Hz, 2H, ring CH$_2$, changing to a singlet upon D$_2$O); IR (KBr) 3400, 3100, 3000, 1700, 1650 cm$^{-1}$; mass spectrum (70 eV) m/z 256 (M$^+$), 200, 91; UV (MeOH) 284.5 nm, (pH 13) 333.5.

Anal. Calcd. for C$_{13}$H$_{12}$N$_4$O$_2$.0.25H$_2$O: C, 59.88; H, 4.79; N, 21.49. Found: C, 60.01; H, 4.84; N, 21.59.

(c) 4,5,6,7-Tetrahydro-1H,8H-imidazo[4,5-d][1,3]diazepine-5,8-dione: The above 3-benzyl-4,5,6,7-tetrahydro-8H-imidazo[4,5-d][1,3]diazepine-5,8-dione (510 mg, 2 mmol) was dissolved in dry acetic acid (10 mL) in a Parr hydrogenation bottle. To this solution was added Pd(OH)$_2$ on carbon (20%, 80 mg), and the mixture was hydrogenated in a Parr hydrogenator at 40 psi for 16 hours. The catalyst was removed by filtration through Celite and washed with acetic acid (5 mL). The filtrate, along with the washings, was evaporated to dryness under reduced pressure to obtain a colorless residue. It was triturated with cold water, and the solid which separated was collected by filtration. It was recrystallized from water as colorless crystals. Yield 275 mg (83%), mp>300° C.: $^1$H NMR (Me$_2$SO-d$_6$) δ 12.88 (br s, 1H, exchangeable with D$_2$O, NH-1), 9.75 (s, 1H, exchangeable with D$_2$O, NH-4), 7.74 (s, 1H, imidazole CH), 7.14 (br s, 1H, exchangeable with D$_2$O, NH-6), 3.65 (d, J=4.5 Hz, 2H, ring CH$_2$, changing to a singlet upon D$_2$O); IR (KBr) 3350–2950, 1750–1650 cm$^{-1}$; mass spectrum (70 eV) m/z 166 (M$^+$), 138, 110, 83; UV (H$_2$O) 278.5 nm, (pH 13–14) 304.0.

Anal. calcd. for C$_6$H$_6$N$_4$O$_2$: C, 43.38; H, 3.64; N, 33.72. Found: C, 43.29; H, 3.65; N, 33.66.

(d) 3- and 1-(2,3,5-Tri-O-benzoyl-β-D-ribofuranosyl)-4,5,6,7-tetrahydro-8H-imidazo[4,5-d][1,3]diazepine-5,8-dione: A mixture of the above 4,5,6,7-tetrahydro-1H,8H-imidazo[4,5-d][1,3]diazepine-5,8-dione (500 mg, 3 mmol) and 1-O-acetyl-2,3,5-tri-O-benzoyl-β-D-ribofuranose (1.51 g, 3 mmol) in dry CH$_3$CN (30 mL) was stirred at room temperature for 10 minutes, under N$_2$, in a three-necked flask equipped with a reflux condenser and a guard tube filled with anhydrous CaCl$_2$/CaSO$_4$. Freshly distilled 1,1,1,3,3,3-hexamethyldisilazane (0.7 mL, 3.6 mmol) and trifluoromethanesulfonic acid (0.3 mL, 3.6 mmol) were added consecutively to the above mixture whereupon it became slightly warm. The reaction was monitored by TLC (toluene:acetic acid:water=5:5:1). After stirring for 1 hour at room temperature, the TLC showed partial completion of the reaction. The reaction mixture was heated at reflux for 2 hours to obtain a clear solution whose TLC showed two different Uv absorbing spots. The solution was cooled, CH$_3$CN (10 mL) and CH$_2$Cl$_2$ (30 mL) were added, and the mixture was extracted with saturated aqueous solution of NaHCO$_3$. The organic layer was separated, the aqueous layer was once again extracted with CH$_2$Cl$_2$ (10 mL), and the combined organic extracts were washed with a saturated aqueous solution of NaCl. The organic layer was dried over anhydrous MgSO$_4$, filtered, and the filtrate was evaporated to dryness under reduced pressure to obtain a solid.

The above-solid, a mixture of two compounds, was dissolved in CH$_2$Cl$_2$ (10 mL), and the solution was mixed with silica gel (40–63 μm, 2 g) and rotary evaporated to dryness. The residue was suspended in CH$_2$Cl$_2$ (10 mL), and the resulting slurry was loaded onto a flash chromatography column packed with silica gel (40–63 μm, 100 g) in CH$_2$Cl$_2$. The column was eluted with a mixture of CH$_2$Cl$_2$-EtOAc (1:1) (250 mL) at 10 mL/min at 6 psi, followed by a mixture of EtOAc-isopropanol (9:1) (200 mL). The appropriate UV-absorbing fractions were pooled and evaporated to dryness. The residue was triturated with EtOAc, and the colorless solid obtained was collected by filtration. It was further purified by recrystallization from CH$_2$Cl$_2$-petroleum ether (40–60° C.) to obtain colorless crystals of 1-(2,3,5-tri-O-benzoyl-δ-D-ribofuranosyl)-4,5,6,7-tetrahydro-8H-imidazo[4,5-d][1,3]diazepine-5,8-dione. Yield 525 mg (35%), mp 239° C.: $^1$H NMR (Me$_2$SO-d$_6$) δ 9.94 (d, J=1.95 Hz, 1H, exchangeable with D$_2$O, NH-4), 8.23 (s, 1H, imidazole CH), 7.63 (m, 16H, Ph-H+NH-6, exchangeable, with $D_2O$), 6.69 (d, J=2.7 Hz, 1H, anomeric H), 5.95 (s, 2H, ribose-H), 4.8 (s, 3H, ribose-H), 3.65 (d, J=4.8 Hz, 2H, ring $CH_2$, singlet upon $D_2O$ exchange).

Anal. Calcd. for $C_{32}H_{26}N_4O_9 \cdot 1/2H_2O$: C, 62.03; H, 4.39; N, 9.04. Found: C, 62.05; H, 4.17; N, 9.02.

The column was further eluted with EtOAc-isopropanol (4:1) at 10 mL/min at 6 psi. The fractions collected were found to be a mixture of two compounds. All the fractions were pooled and evaporated to dryness under reduced pressure. The residue obtained was dissolved in $CHCl_3$ (2 mL) and loaded onto a Chromatotron plate (1 mm thickness, Kieselgel 60 $GF_{254}$). It was eluted with a mixture of $CHCl_3$—MeOH (4:1). The appropriate UV-absorbing fractions were pooled and rotary evaporated to dryness to obtain 3-(2,3,5-tri-O-benzoyl-β-D-ribofuranosyl)-4,5,6,7-tetrahydro-8H-imidazo[4,5-d][1,3]diazepine-5,8-dione as a pinkish solid. Yield 225 mg (15%), mp 252° C.: $^1$H NMR ($Me_2SO$-$d_6$) δ 9.99 (s, 1H, exchangeable with $D_2O$, NH-4), 8.02–7.40 (m, 17H, Ph-H+imidazole CH+NH-6, exchangeable with $D_2O$), 6.63 (d, J=6.0 Hz, 1H, anomeric H), 6.04–5.93 (m, 2H, ribose-H), 4.79–4.68 (m, 3H, ribose-H), 3.65 (d, J=4.8 Hz, 2H, ring $CH_2$, singlet upon $D_2O$ exchange).

Anal. Calcd. for $C_{32}H_{26}N_4O_9 \cdot 1H_2O$: C, 61.14; H, 4.49; N, 8.91. Found: C, 61.39; H, 4.22; N, 8.88.

(e) 1-β-D-Ribofuranosyl-4,5,6,7-tetrahydro-8H-imidazo[4,5-d][1,3]diazepine-5,8-dione: To a well-stirred solution of the above 1-(2,3,5-tri-O-benzoyl-β-D-ribofuranosyl)-4,5,6,7-tetrahydro-8H-imidazo[4,5-d][1,3]diazepine-5,8-dione (300 mg, 0.49 mmol) in dry MeOH (15 mL) and $CH_2Cl_2$ (3 mL) in a 50 mL three-necked flask equipped with a reflux condenser and maintained under $N_2$, was added dropwise, a freshly prepared solution of NaOMe in MeOH (10 mL) until the pH of the solution reached 13–14 (litmus). The mixture was stirred at room temperature for 30 minutes, cooled in an ice-water bath, and carefully neutralized to pH 6–7 with acetic acid. The solvents were removed under reduced pressure, the residue was washed with $Et_2O$ and triturated with cold $H_2O$ to obtain a solid which was recrystallized from water into colorless crystals. Yield 111 mg (76%), mp 266° C. (dec.): $^1$H NMR ($Me_2SO$-$d_6$) δ 9.77 (br s, 1H, exchangeable with $D_2O$, NH-4), 8.28 (s, 1H, imidazole CH), 7.21 (br s, 1H, exchangeable with $D_2O$, NH-6), 6.24 (d, J=2.7 Hz, 1H, anomeric H), 5.34 (d, J=4.9 Hz, 1H, exchangeable with $D_2O$, ribose-OH), 5.0 (t, 2H, exchangeable with $D_2O$, two ribose-OH), 3.65–4.05 (m, 5H, ribose-H), 3.65 (d, J=4.6 Hz, 2H, ring $CH_2$, singlet upon $D_2O$ exchange); UV ($H_2O$) 239.5, 291.5 nm,(pH 13) 294.0, 341.0, (pH 2) 287.5.

Anal. Calcd. for $C_{11}H_{14}N_4O_6$: C, 44.30; H, 4.73; N, 18.78. Found: C, 44.25; H, 4.74; N, 18.69.

(f) 1-β-D-ribofuranosyl-4,5,6,7-tetrahydro-8-hydroxy-8H-imidazo[4,5-d][1,3]diazepine-5-one: The above nucleoside 1-β-D-ribofuranosyl-4,5,6,7-tetrahydro-8H-imidazo[4,5-d][1,3]diazepine-5,8-dione (58 mg, 0.20 mmol) was dissolved in a mixture of MeOH:$H_2O$ (1:1), and the solution was stirred at room temperature for 10 minutes. Sodium borohydride (21 mg, 0.55 mmol) was added to the cloudy solution, and the reaction mixture was stirred at room temperature for 30 minutes to form a clear solution. The excess reducing agent was decomposed by adding dry ice. The reaction mixture was filtered, and the filtrate was evaporated to dryness to obtain a solid. Yield 45 mg (75%), mp 238° C. (dec.): $^1$H NMR ($D_2O$) δ 7.56 (s, 1H, imidazole CH), 5.61 (d, J=3.3 Hz, 1H, anomeric H), 4.92–4.83 (m, 1H, H-8), 3.95 (m, 2H, H-2'+H-3'), 3.63–3.48 (m, 4H, H-5' $CH_2$+H-7 $CH_2$).

Example 6

4,5,7,8-Tetrahydro-6-hydroxy-3H,6H-imidazo[4,5-e][1,4]diazepine-5,8-dione

[Formula IV, Where U, Y, Z, K=C; X, W, J, L=N; $R_1$, $R_5$=O; $R_3$=OH; $R_2$, $R_4$, $R_6$, $R_7$, $R_8$=H; $R_9$= None]

(a) Diethyl 2-[N-(1-benzyl-5-nitroimidazole-4-carbonyl)amino]malonate for 1-Benzyl-4-[N((bis(ethoxycarbonyl)methyl)carbamoyl]-5-nitroimidazolel: A 250-mL three-necked, round-bottomed flask, equipped with a reflux condenser, was charged with 1-benzyl-5-nitro-4-carboxylic acid (Hosmane, et al., *J. Heterocycl. Chem.* 27:2189 (1990)); (5.0 g, 20 mmol), 1,1'-carbonyldiimidazole (CDI) (4.5 g, 27 mmol), and dry tetrahydrofuran (THF) (150 mL). The mixture was heated at reflux for 4 hours, when a clear solution was formed. The solution was cooled to room temperature, and a freshly prepared solution of diethylaminomalonate made from its hydrochloride salt (5.71 g, 27 mmol) by treatment with triethylamine (4.0 mL, 28.7 mmol) in 100 mL of methylene chloride, was added. The reaction mixture was stirred at room temperature for 1 hour, when a tlc (silica gel, $CHCl_3$:MeOH, 8:1) showed the formation of a new compound which had a higher Rf than the starting material. The reaction mixture was evaporated to dryness on a rotary evaporator, and the residual gum was suspended in ice-water and stirred overnight on a magnetic stirrer. A pale yellow solid that separated was filtered, washed with 2×100 mL of water, and dried. The compound was recrystallized from methanol into pale yellow flakes. Yield 7.9 g (96%), mp 88° C.: $^1$H NMR (DMSO-$d_6$) δ 9.27 (d, J=7.0 Hz, 1H, exchangeable with $D_2O$, NH), 8.28 (s, 1H, imidazole CH), 7.38–7.19 (m, 5H, Ph-H), 5.54 (s, 2H, benzyl $CH_2$), 5.23 (d, J=7.5 Hz, 1H, CH), 4.22–4.14 (q, 4H, two ester $CH_2$), 1.21–1.18 (t, 6H, two ester $CH_3$); MS (EI) m/z 331 ($M^+$—$CO_2Et$), 303, 259, 230.

Anal. Calcd. for $C_{18}H_{20}N_4O_7$: C, 53.48; H, 4.98; N, 13.85. Found: C, 53.50; H, 5.03; N, 13.91.

(b) Diethyl 2-Methoxy-2-[N-(1-benzyl-5-nitroimidazole-4-carbonyl)amino]malonate: A 300-mL three-necked, round-bottomed flask, equipped with a $N_2$ inlet, was charged with 150 mL of dry methanol. Clean, freshly cut sodium metal (0.5 g, 21.74 mmol) was added, and the mixture was stirred under $N_2$ atmosphere to form a clear solution. The flask was cooled in an acetone-dry ice bath to −78° C., and the above diethyl 2-[N-(1-benzyl-5-nitroimidazole-4-carbonyl)amino]malonate (5.0 g, 12.37 mmol) was added when the color of the reaction mixture changed to dark brown. Bromine (0.9 mL, 17 mmol) was introduced through a syringe when the color of the solution changed to off-white, and some solid started separating. After 1 hour, the reaction mixture was neutralized with 2N HCl to pH 6.5, and evaporated to dryness on a rotary evaporator. The residue was suspended in water and extracted with chloroform (2×250 mL). The organic layer was separated, dried over anhydrous magnesium sulfate, filtered, and the filtrate evaporated to dryness. The residue was suspended in ether and was left to stand at room temperature. The off-white solid separated was recrystallized from ether. Yield 4.7 g (88%), mp 126–127° C.: $^1$H NMR (DMSO-$d_6$) δ 9.42 (s, 1H, exchangeable with $D_2O$, NH), 8.30 (s, 1H, imidazole CH), 7.37–7.23 (m, 5H, Ph-H), 5.55 (s, 2H, benzyl $CH_2$), 4.19 (q, iJ=7.1 Hz, 4H, two ester $CH_2$), 3.25 (s, 3H, OMe), 1.65 (t, J=6.9 Hz, 6H, two ester $CH_3$).

Anal. Calcd. for $C_{19}H_{22}N_4O_8$: C, 52.53; H, 5.10; N, 12.89. Found: C, 52.47; H, 5.11; N, 12.87.

(c) Diethyl 2-Methoxy-2-[N-(5-amino-1-benzylimidazole-4-carbonyl)amino]malonate: A mixture of the above diethyl 2-methoxy-2-[N-(1-benzyl-5-nitroimidazole-4-carbonyl)amino]malonate (500 mg, 1.15 mmol) and 5% Pd—C (100 mg) in absolute methanol (100 mL) was hydrogenated in a Parr hydrogenator at 40 psi for 50 minutes. The reaction mixture was filtered through Celite, and the filtrate was evaporated to dryness. The residual syrup was purified by rotating disk chromatography on a Chromatotron™ plate, made of silica gel (particle size 15 μm, thickness 2 mm), eluting with chloroform. Appropriate UV-absorbing fractions were pooled and evaporated to afford a syrup, which upon trituration with ether, gave an off-white solid. The compound was recrystallized from ether. Yield 255 mg (55%), mp 162–163° C.: $^1H$ NMR (DMSO-$d_6$) δ 7.95 (s, 1H, exchangeable with $D_2O$, NH), 7.32–7.22 (m+s, 6H, imidazole CH+Ph-H), 6.01 (s, 2H, exchangeable with $D_2O$, $NH_2$), 5.08 (s, 2H, benzyl $CH_2$), 4.19 (q, J=7.0 Hz, 4H, two ester $CH_2$), 3.18 (s, 3H, OMe), 1.15 (t, J=7.0 Hz, 6H, two ester $CH_3$).

Anal. Calcd. for $C_{19}H_{24}N_4O_6$: C, 56.42; H, 5.98; N, 13.85. Found: C, 56.35; H, 5.93; N, 13.82.

(d) Diethyl 2-Methoxy-2-[N-((1-benzyl-5-(benzalimino)imidazole-4-carbonyl)amino]malonate:

A 500-mL round-bottomed flask was charged with the above diethyl 2-methoxy-2-[N-(5-amino-1-benzylimidazole-4-carbonyl)amino]malonate (3.0 g, 7.4 mmol) and dry benzene (300 mL). p-Toluenesulfonic acid monohydrate (190 mg, 1 mmol) was added, followed by benzaldehyde (0.82 g, 7.7 mmol). The flask was fitted with a Dean-Stark apparatus, equipped with a reflux condenser. The reaction mixture was heated gently to reflux, and the water collected in the trap was continuously removed. The color of the reaction mixture changed to light yellow. A tlc (silica gel, chloroform:acetone, 9:1) of the reaction mixture taken after 3 hours showed a new UV-absorbing compound with a higher Rf than the starting material, along with a small amount of the unreacted starting material. The reaction mixture was allowed to continue to reflux for an additional hour, cooled, and concentrated by rotary evaporation. Chloroform (200 mL) was added, followed by 10 mL of a saturated solution of aqueous sodium bicarbonate. The mixture was transferred to a separatory funnel and extracted with water (2×50 mL). The organic layer was collected, dried over anhydrous magnesium sulfate, filtered, and the filtrate evaporated to dryness to afford a syrup. Trituration of the syrup with ether provided a pale yellow solid which was recrystallized from ether. Yield 3.0 g (84%), mp 129–131° C.: $^1H$ NMR (DMSO-$d_6$) δ 9.2 (s, 1H, CH), 8.7 (s, 1H, exchangeable with $D_2O$, NH), 8.02 (s, 1H, CH), 7.86–7.3 (m, 10H, Ph-H), 5.31 (s, 2H, benzyl $CH_2$), 4.21 (q, J=6.9 Hz, 4H, two ester $CH_2$), 3.2 (s, 3H, OMe), 1.16 (t, J=6.9 Hz, 6H, two ester $CH_3$).

Anal. Calcd. for $C_{26}H_{28}N_4O_6$: C, 63.40; H, 5.73; N, 11.38. Found: C, 63.22; H, 5.62; N, 11.63.

(e) Diethyl 2-Methoxy-2-[N-((1-benzyl-5-(benzylamino)imidazole-4-carbonyl)amino]malonate:

To a solution of the above diethyl 2-methoxy-2-[N-((1-benzyl-5-(benzalimino)imidazole-4-carbonyl)amino]malonate (2.5 g, 5 mmol) in methanol (100 mL), contained in a Parr hydrogenator bottle, was added 10% Pd—C (250 mg). The mixture was hydrogenated at 40 psi for 45 minutes, the catalyst was filtered over Celite, and the filtrate was evaporated. The residue was purified by rotating disk chromatography on a Chromatotron™ plate, made of silica gel (particle size 15 μm, thickness 4 mm), eluting with chloroform. Appropriate UV-absorbing fractions were pooled and evaporated to afford a syrup, which upon trituration with ether, and standing, gave a white solid. The solid was recrystallized from ether. Yield 2.1 g (85%), mp 96–98° C.: $^1H$ NMR (DMSO-$d_6$) δ 8.3 (s, 1H, exchangeable with $D_2O$, NH), 7.4 (s, 1H, imidazole CH), 7.3–7.0 (m, 10H, Ph-H), 6.1 (t, J=6.9 Hz, 1H, exchangeable with $D_2O$, NH), 5.15 (s, 2H, benzyl $CH_2$), 4.4 (d, J=6.9 Hz, 2H, benzyl $CH_2$), 4.2 (m, 4H, two ester $CH_2$), 3.19 (s, 3H, OMe), 1.16 (t, 6H, two ester $CH_3$).

Anal. Calcd. for $C_{26}H_3N_4O_6 \cdot 1H_2O$: C, 60.96; H, 6.25; N, 10.93. Found: C, 61.27; H, 6.02; N, 11.07.

(f) 3,4-Dibenzyl-4,5,7,8-tetrahydro-6-methoxy-6H-imidazo[4,5-e][1,4]diazepine-5,8-dione: A fresh solution of sodium methoxide, prepared by dissolving cleanly cut sodium metal (300 mg, 13 mg.atom) in anhydrous methanol (100 mL), was charged to a 250-mL round-bottomed flask, equipped with a reflux condenser and a nitrogen gas inlet. The above diethyl 2-methoxy-2-[N-((1-benzyl-5-(benzylamino)imidazole-4-carbonyl)amino]malonate (2.0 g, 4.0 mmol) was added, and the clear solution was heated at reflux for 3 hours under $N_2$ atmosphere. The reaction mixture was cooled in an ice-water bath and neutralized to pH 7 with 1N HCl. Evaporation of the solvents yielded a white mass which was purified by flash chromatography on silica gel (particle size 40–63 μm), eluting with a gradient of chloroform-methanol. Appropriate fractions were pooled and evaporated to obtain a white solid which was recrystallized from methanol-water. Yield 400 mg (26%): $^1H$ NMR (DMSO-$d_6$) δ 7.6 (s, 1H, imidazole CH), 7.46 (d, J=4.5 Hz, 1H, exchangeable with $D_2O$, NH), 7.33 (m, 10H, Ph-H), 5.1 (d, 2H, benzyl $CH_2$), 4.7 (d, J=4.5 Hz, 1H, CH), 4.2 (s, 2H, benzyl $CH_2$), 3.42 (s, 3H, OMe).

(g) 3,4-Dibenzyl-4,5,7,8-tetrahydro-6-hydroxy-6H-imidazo[4,5-e][1,4]diazepine-5,8-dione:
Method A: By Ring-Closure, Followed by Hydrolysis of Diethyl 2-Methoxy-2-[N-((1-benzyl-5-(benzylamino)imidazole-4-carbonyl)amino]malonate: A fresh solution of sodium methoxide, prepared by dissolving cleanly cut sodium metal (300 mg, 13 mg.atom) in anhydrous methanol (100 mL), was charged to a 250-mL round-bottomed flask, equipped with a reflux condenser and a nitrogen gas inlet. The above diethyl 2-methoxy-2-[N-((1-benzyl-5-(benzylamino)imidazole-4-carbonyl)amino]malonate (2.0 g, 4.0 mmol) was added, and the clear solution was heated at reflux for 3 hours under $N_2$ atmosphere. The reaction mixture was cooled in an ice-water bath, and the pH was adjusted to 2–3 with 1N HCl. Upon concentration of the reaction mixture by rotary evaporation, a fluffy, off-white solid separated which was then filtered, washed with water, and dried. Yield 1.0 g (69%), mp 198–200° C.: $^1H$ NMR (DMSO-$d_6$) δ 12.8 (br s, 1H, exchangeable with $D_2O$, OH), 7.59 (s, 1H, imidazole CH), 7.30 (m, 11H, 10 Ph-H +1 NH, exchangeable with $D_2O$), 5.1 (two d, J=15.9 Hz, 2H, benzyl $CH_2$), 4.6 (d, J=4.2 Hz, 1H, CH), 4.1 (two d, J=14.7 Hz, 2H, benzyl $CH_2$).

Anal. Calcd. for $C_{20}H_{18}N_4O_3 \cdot 0.25H_2O$: C, 65.51; H, 5.05; N, 15.27. Found: C, 65.36; H, 5.00; N, 15.25.
Method B: By Hydrolysis of 3,4-Dibenzyl-4,5,7,8-tetrahydro-6-methoxy-6H-imidazo[4,5-e][1,4]diazepine-5,8-dione: To a suspension of 60% sodium hydride (25 mg, 0.62 mmol) in dry tetrahydrofuran (30 mL) was added the above 3,4-dibenzyl-4,5,7,8-tetrahydro-6-methoxy-6H-imidazo[4,5-e][1,4]diazepine-5,8-dione (200 mg, 0.53 mmol). The reaction mixture was stirred under $N_2$ atmosphere at room temperature overnight, and the pH was adjusted to 6.5 with 1N HCl. Upon concentration of the reaction mixture by rotary evaporation, a fluffy, off-white solid separated which was filtered, washed with water, and dried. The mp, Rf, and $^1$H NMR of this product were identical to those of 3,4-dibenzyl-4,5,7,8-tetrahydro-6-hydroxy-6H-imidazo[4,5-e][1,4]diazepine-5,8-dione, prepared by Method A above.

(h) 4,5,7,8-Tetrahydro-6-hydroxy-3H,6H-imidazo[4,5-e][1,4]diazepine-5,8-dione:

A solution of the above 3,4-dibenzyl-4,5,7,8-tetrahydro-6-hydroxy-6H-imidazo[4,5-e][1,4]diazepine-5,8-dione (500 mg, 1.38 mmol) in glacial acetic acid (20 mL) was transferred to a Parr hydrogenation bottle. To this solution was added 10% (Pd(OH)$_2$ on carbon (100 mg), and the mixture was hydrogenated at 40 psi for 20 hours. The catalyst was removed by filtration through Celite and washed with acetic acid (15 mL). The filtrate, along with washings, was evaporated to dryness under reduced pressure to obtain a colorless residue. The residue was dissolved in H$_2$O and re-precipitated with acetone to obtain a solid. The solid was filtered and dried. $^1$H NMR (DMSO-d$_6$) δ 12.45 (br s, 1H, exchangeable with D$_2$O, NH), 7.45 (s, 1H, imidazole CH), 7.28 (s, 1H, exchangeable with D$_2$O, NH), 6.70 (br s, 1H, exchangeable with D$_2$O, NH), 4.85 (s, 1H, CH).

Examples 7 and 8

6-Amino-6-methoxycarbonyl-4,5,7,8-tetrahydro-6H-imidazo[4,5-e]-[1,4]diazepine-5,8-dione (Example 7)

[Formula IV, Where U, Y, Z, K=C; X, W, J, L=N; R$_1$, R$_5$=O; R$_3$=NH$_2$; R$_4$=CO$_2$CH$_3$; R$_2$, R$_6$, R$_7$, R$_8$=H; R$_9$=None], and 6-Methoxy-6-methoxycarbonyl-4,5,7,8-tetrahydro-6H-imidazo[4,5-e][1,4]-diazepine-5,8-dione (Example 8)

[Formula IV, Where U, Y, Z, K=C; X, W, J, L=N; R$_1$, R$_5$=O; R$_3$=OCH$_3$; R$_4$=CO$_2$CH$_3$; R$_2$, R$_6$, R$_7$, R$_8$=H; R$_9$=None]

(a) Diethyl 2-[N-(1-Benzyl-5-nitroimidazolyl-4-carbonyl)amino]malonate

A 250-ml three-necked, round-bottomed flask, equipped with a reflux condenser, was charged with 1-benzyl-5-nitroimidazole-4-carboxylic acid (Hosmane, et al., *J. Heterocyclic Chem.* 27: 2189 (1990)) (5.0 g, 20 mmole), 1,1'-carbonyldiimidazole (CDI) (4.5 g, 27 mmole), and dry tetrahydrofuran (THF) (150 ml). The mixture was heated at reflux for 4 hours, when a clear solution was formed. The solution was cooled to room temperature, and a freshly prepared solution of diethyl aminomalonate from its hydrochloride salt (5.71 g, 27 mmole) by treatment with triethylamine (4.0 ml, 28.7 mmole) in 100 ml of methylene chloride, was added. The reaction mixture was stirred at room temperature for 1 hour, when a tic (silica gel, chloroform:methanol, 8:1) showed the formation of a new compound which had a higher Rf than the starting material. The reaction mixture was evaporated to dryness on a rotary evaporator, and the residual gum was suspended in ice-water, and stirred overnight on a magnetic stirrer. A pale yellow solid that separated was filtered, washed with 2×100 ml of water, and dried. The compound was recrystallized from methanol into pale yellow flakes, yield 7.9 g (96%), mp 88°; $^1$H nmr (DMSO-d$_6$): δ 9.27 (d, J=7.0 Hz, 1H, exchangeable with deuterium oxide, NH), 8.28 (s, 1H, imidazole CH), 7.38–7.19 (m, 5H, Ph-H), 5.54 (s, 2H, benzyl CH$_2$), 5.23 (d, J=7.5 Hz, 1H, CH), 4.22–4.14 (q, 4H, two ester CH$_2$), 1.21–1.18 (t, 6H, two ester CH$_3$); ms (EI): m/z 331 (M$^+$-CO$_2$Et), 303, 259, 230.

Anal. Calcd. for C$_{18}$H$_{20}$N$_4$O$_7$: C, 53.48; H, 4.98; N, 13.85. Found: C, 53.50; H, 5.03; N, 13.91.

(b) Diethyl 2-Benzylamino-2-[N-(1-benzyl-5-nitroimidazolyl-4-carbonyl)amino]malonate Diethyl 2-[N-(1-benzyl-5-nitroimidazolyl-4-carbonyl)amino]malonate, prepared above, (1.0 g, 2.47 mmol) was added to a stirred solution of NaH (60%) (200 mg, 5.0 mmol) in dry THF at −78° C., followed by the addition of bromine (0.25 mL, 4.3 mmol). It was stirred for 10 minutes, and a solution of benzylamine (0.4 mL, 3.6 mmol) in dry THF (10 mL) was added. The reaction mixture was stirred for an additional hour, and was slowly brought to room temperature. The solvents were evaporated on a rotary evaporator under reduced pressure, and the residue was taken in 50 mL of water. The pH of the solution was adjusted to 7, and it was extracted with chloroform (2×125 mL). The combined organic extracts were successively washed with dilute hydrochloric acid and water, dried over anhydrous magnesium sulfate, filtered, and the filtrate evaporated to dryness. The residue was triturated with ether when an off-white solid separated. The solid was filtered and dried, yield 0.83 g (66%), mp 100–101° C.; $^1$H NMR (DMSO-d$_6$): δ 9.09 (s, 1H, exchangeable with deuterium oxide, NH), 8.2 (s, 1H, imidazole CH), 7.40–7.10 (m, 10H, 2×Ph-H), 5.54 (s, 2H, benzyl CH$_2$), 4.14 (q, J=7.0 Hz, 4H, two ester CH$_2$), 3.65 (d, J=6.6 Hz, CH$_2$NH), 3.36 (t, J=6.6 Hz, 1H, exchangeable with deuterium oxide, NH), 1.14 (t, J=7.0 Hz, 6H, two ester CH$_3$).

Anal. Calcd. for C$_{25}$H$_{27}$N$_5$O$_7$: C, 58.92; H, 5.34; N, 13.74. Found: C, 59.02; H, 5.36; N, 13.77.

(c) Diethyl 2-Benzylamino-2-[N-(5-amino-1-benzylimidazolyl-4-carbonyl)amino]malonate A mixture of the above diethyl 2-Benzylamino-2-[N-(1-benzyl-5-nitroimidazolyl-4-carbonyl)amino]malonate (1.0 g, 1.9 mmol) and Pd—C (10%) (100 mg) in absolute methanol (100 mL) was hydrogenated in a Parr hydogenator at 40 psi for 35 minutes. The reaction mixture was filtered through Celite, and the filtrate evaporated to dryness on a rotary evaporator. The residual semi-solid was triturated with ether to obtain a white solid. The solid was filtered and dried, yield 0.74 g (79%), mp 121–123° C.; $^1$H NMR (DMSO-d$_6$): δ 7.85 (s, 1H, imidazole CH), 7.37–7.19 (m, 11H, 2×Ph-H+NH), 5.96 (s, 2H, exchangeable with deuterium oxide, NH$_2$), 5.08 (s, 2H, benzyl CH$_2$), 4.10 (q, J=7.0 Hz, 4H, two ester CH$_2$), 3.55 (d, J=6.0 Hz, CH$_2$NH), 3.20 (m, 1H, exchangeable with deuterium oxide, NHCH$_2$), 1.10 (t, J=7.0 Hz, 6H, two ester CH$_3$).

Anal. Calcd. for C$_{25}$H$_{29}$N$_5$O: C, 62.61; H, 6.09; N, 14.60. Found: C, 62.47; H, 6.12; N, 14.57.

(d) 6-Amino-6-methoxycarbonyl-4,5,7,8-tetrahydro-6H-imidazo[4,5-e][1,4]diazepine-5,8-dione (Example 7) and 6-Methoxy-6-methoxycarbonyl-4,5,7,8-tetrahydro-6H-imidazo[4,5-e][1,4]diazepine-5,8-dione (Example 8)

To a solution of sodium methoxide, freshly prepared by dissolving sodium metal (368 mg, 16 mg.atom) in methanol (25 mL), was added the above diethyl 2-Benzylamino-2-[N-(5-amino-1-benzylimidazolyl-4-carbonyl)amino]malonate (2.0 g, 4.1 mmol), when the color of the reaction mixture changed to dark brown. The mixture was heated to reflux for 2.5 hours. It was cooled, the pH adjusted to 7.5 with 1N HCl, and was evaporated to dryness on a rotary evaporator. The residue was suspended in glacial acetic acid (50 mL), and 20% Pd(OH)$_2$—C (250 mg) was added. The mixture was hydrogenated in a Parr hydrogenator for 18 hours. The reaction mixture was filtered through Celite, and the filtrate evaporated to dryness. The residue was purified by flash chromatography on a silica gel column, eluting first with a mixture of chloroform-methanol (6:1) to collect the faster moving 6-methoxy-6-methoxycarbonyl-4,5,7,8-tetrahydro-6H-imidazo[4,5-e][1,4]-diazepine-5,8-dione (Example 8), recrystallized from MeOH—H$_2$O, mp>280° C.; $^1$H NMR (DMSO-d$_6$) δ 12.97 (br s, 1H, exchangeable with D$_2$O, NH), 11.36 (br s, 1H, exchangeable with deuterium oxide, NH), 8.66 (s, 1H, exchangeable with deuterium oxide, NH), 7.70 (s, 1H, imidazole CH), 3.73 (s, 3H, CO$_2$Me), 3.08 (s, 3H, OMe); MS (EI, 70 eV) m/z 254 (M$^+$).

Further elution of the column with a mixture of chloroform-methanol (4:1) afforded the slower moving 6-amino-6-methoxycarbonyl-4,5,7,8-tetrahydro-6H-imidazo[4,5-e]-[1,4]diazepine-5,8-dione (Example 7), recrystallized from MeOH as white rhombic crystals, mp: sinters at 196° C. and decomposes at 203° C.; $^1$H NMR (DMSO-d$_6$) δ 12.93 (br s, 1H, exchangeable with deuterium oxide, NH), 11.13 (br s, 1H, exchangeable with deuterium oxide, NH), 7.83 (s, 1H, exchangeable with deuterium oxide, NH), 7.67 (s, 1H, imidazole CH), 3.4 (s, 3H, CO$_2$Me), 3.0 (s, 2H, exchangeable with deuterium oxide, NH$_2$); MS (EI, 70 eV) m/z 239 (M$^+$).

Anal. Calcd. for C$_8$H$_9$N$_5$O$_4$: C, 40.17; H, 3.78; N, 29.27. Found: C, 40.06; H, 3.74; N, 29.15.

Example 9

Inhibition of Adenosine Deaminase by 4,6,8-Triimino-1-β-D-ribofuranosylimidazo[4,5-e][1,3]diazepine (or its Tautomer, see Example 4 Above)

The inhibition of the hydrolysis of adenosine (K$_m$=2.5×10$^{-5}$ to 3.1×10$^{-5}$) to xanthosine was monitored at 265 nm at 25° C. in a phosphate buffer (pH 7), employing adenosine deaminase (Type IV) from bovine spleen (a suspension in 3.2 M (NH$_4$)$_2$SO$_4$, pH 6). The concentration of inhibitor, the title compound, used for the present study ranged from 4.6×10$^{-5}$ to 9.2×10$^{-5}$ M. The enzyme concentration used for each of the assays was 0.0235 units/mL. As computed by the Lineweaver-Burk plot. (refer to any standard Biochemistry text), the title compound was found to be a competitive inhibitor of adenosine deaminase with a K$_i$=3.85×10$^{-5}$ to 4×10$^{-4}$ M.

Examples 10 and 11

Inhibition of Guanase by 6-Amino-6-methoxycarbonyl-4,5,7,8-tetrahydro-6H-imidazo[4,5-e]-[1,4]diazepine-5,8-dione (see-Example 7 Above) and 6-Methoxy-6-methoxycarbonyl-4,5,7,8-tetrahydro-6H-imidazo[4,5-e][1,4]-diazepine-5,8-dione (see Example 8 Above)

The inhibition of the hydrolysis of guanine (K$_m$=6.4×10$^{-6}$ to 7.1×10$^{-6}$) to xanthine were monitored spectrophotometrically at 248 nm at 21° C. in a Tris buffer (pH 7.6), employing rabbit liver guanase. The concentration of the inhibitor ranged from 4×10$^{-5}$ M to 8×10$^{-5}$ M (Example 7), and 4.4×10$^{-5}$ M to 8.9×10$^{-5}$ M (Example 8). The concentration of the enzyme used for each assay was 0.0082 units/mL. As computed by the Lineweaver-Burk plot, both of the title compounds were found to be competitive inhibitors of guanase with K$_i$'s equal to 1.9×10$^{-4}$ M and 5.4×10$^{-4}$ M, respectively.

Example 12

Antiretroviral Activity of 4,5,7,8-Tetrahydro-6H-1-β-D-ribofuranosylimidazo[4,5-e][1,2,4]triazepine

[Formula IV, Where U, Z, K=C; X, Y, W, J, L=N; R$_1$, R$_5$=O; R$_2$, R$_3$, R$_6$, R$_7$, R$_8$=H; R$_4$=None]

(a) Cells and Virus

The continuous murine fibroblast cell line SC-1 was propagated at 37° C. in Eagle's Minimum Essential Medium (MEM), supplemented with 10% fetal bovine serum and 12.5 μg/mL gentamycin. Cas-Br-M murine leukemia virus (MuLV) pools were prepared in SC-1 (Hoffman, et al., *J. Neuroimmunology* 1:272 (1981)). Cell lines derived from infection of SC-1 with Cas-Br-M MuLV chronically produce high titers of infectious ecotropic virus. The virus was stored as aliquots frozen below −70° C.

(b) Viral Infection and the Reverse Transcriptase (RT) Inhibition Assay

SC-1 cells (10$^5$ cells per 60 mm petri dish) were grown in complete medium with 4 μg/mL polybrene overnight. Three hours prior to infection, the media was removed and a medium containing various concentrations of the test compound was addded to each of two plates per concentration. As internal controls, a set of duplicate plates were run with no drug or with 1000 units/mL of mouse fibroblast interferon. Cells were incubated at 37° C. for 3 hours to provide for transport and metabolism of the test compound, and then all plates were were infectede by the addition of 0.5 mL of the virus at a multiplicity of infection of 0.5 PFU/cell of Cas-Br-M MULV. At 24 hours post-infection (pi), the medium containing the virus inoculum was removed and replaced with a fresh medium containing the test compound. The cultures were then incubated for 48 hours prior to harvest of the culture fluid. The culture fluids were pooled and clarified by centrifugation at 2000×g. An 8 mL sample was centrifuged at 105,000×g through a 5 mL pad of 20% w/w sucrose, thus pelleting the virus particles and separating them from contaminating cellular debris and the test agent. The pellet was suspended in 80 μL of RT (reverse transcriptase) buffer (50 mM Tris buffer, pH 8.3, containing 1% Triton X-100) affecting a 100-fold concentration of the virus particles. The resulting virus suspension was assayed in an RT assay (J. Bilello, et al., *Proc. Natl. Acad. Sci.* 71:3234 (1974)), using dT.rA as the exogenous primertemplate and tritiated deoxythymidine triphosphate ($^3$H-dTTP) as the label. Briefly, 5–25 μL of the pelleted virions in RT buffer was added to a reaction mixture containing 50 mM Tris (pH 8.3), 20 mM dithiothreitol, 0.6 mM MnCl$_2$, 0.05% NP-40, 5 μg of oligodeoxythymidilic acid (dT$_{10}$), 10 μg of polyriboadenylic acid (poly rA) per mL, and 10 μM $^3$H-dTTP in a total volume of 100 μL. Incorporation of the radiolabeled nucleotide into the trichloroacetic acid (TCA) precipitable product after a 60 minute incubation was determined. Duplicate 40 μL aliquots were transferred to Whatman 3 MM filters, then precipitated with TCA, dried, and the filter-associated radioactive product was counted by liquid scintillation spectrometry. Assay conditions were determined such that the incorporation was directly proportional to the enzyme concentration over a 100 fold concentration range. The data are summarized in the following Table:

Example 13

Figure 4:
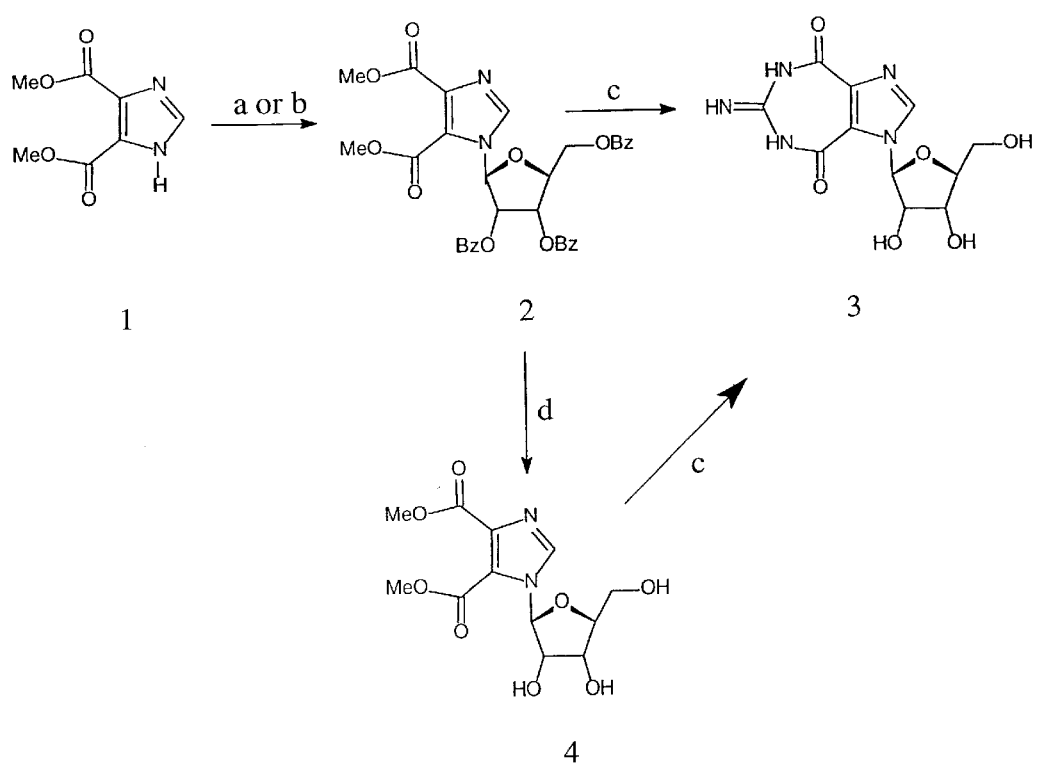

Synthesis and Anti-Hepatitis B Virus Effects of 6-Imino-6H-1-β-D-ribofuranosyl-4,5,7,8-tetrahydroimidazo[4,5-e][1,3]diazepine-4,8-dione (Compound 3, Shown in FIG. 4)

[Formula IA, Where J, L, X, Z=N; K, U, Y, W=C; $R_1=R_5=O$; $R_3=NH$; $R_2=R_4=R_7=H$; $R_8=NONE$; and $R_6=1$-β-D-Ribofuranosyl]

This Example describes an efficient, short synthesis of the title 5:7-fused, planar, and potentially aromatic, ring-expanded nucleoside containing the imidazo[4,5-e][1,3]diazepine heterocyclic ring system. The compound is 6-Imino-6H-1-β-D-ribofuranosyl-4,5,7,8-tetrahydroimidazo[4,5-e][1,3]diazepine-4,8-dione.

This Example further describes the observed potent anti-hepatitis B virus activity of the compound in vitro.

Synthesis

The target compound 3 (shown as compound 3 in FIG. 4), was synthesized in two steps starting with methyl 4,5-imidazoledicarboxylate (compound 1 in FIG. 4) in 81% overall yield. The Vorbrüggen ribosylation (Vorbrüggen, H.; Bennua, B. Chem. Ber., 114, 1279,1981; Vorbruggen et al. Chem. Ber., 114, 1234 1981) of compound 1 (FIG. 4) was carried out using a combination of either hexamethyldisilazane (HMDS)/trimethyl- silyl chloride (TMSCl)/trifluoromethanesulfonic acid (TFMSA) or bis(trimethylsilyl)trifluoro-acetamide (BSTFA)/trimethylsilyl iodide (TMSI)/pyridine, and 1-O-acetyl-2,3,5-tri-O-benzoyl-β-D-ribofuranose. The product compound 2 (Wyss, P. C.; Fischer, U. Helv. Chim. Acta 1978, 61, 3149; Cook, P. D.; Dea, P.; Robins, R. K. J. Heterocyclic Chem. 1978, 15, 1; Cook, P. D.; Robins, R. K. in Nucleic Acid Chemistry, Part 1, Townsend, L. B and Tipson, R. S., Ed., New York, 1978, p 211; Fischer, U.; Wyss, P. C. Ger. Offen. 2735458, 1978, Chem. Abstr. 89:24726e, 1978; Fischer, U.; Wyss, P. C. Belg. 857512, 1978, Chem. Abstr. 89:44128q, 1978; Tapiero, C.; Imbach, J. L.; Panzicka, R. P., Townsend, L. B. J. Carbohyd. Nucleosides Nucleotides 1976, 3, 191), shown in FIG. 4, obtained in 89 or 90% yield, respectively, by the two methods, could be condensed either directly with guanidine hydrochloride in the presence of sodium methoxide in methanol or could be hydrolyzed first into the sugar deprotected (FIG. 4, compound 4) (Wyss, P. C.; Fischer, U. Helv. Chim. Acta 1978, 61, 3149; Cook, P. D.; Dea, P.; Robins, R. K. J. Heterocyclic Chem. 1978, 15, 1; Cook, P. D.; Robins, R. K. in Nucleic Acid Chemistry, Part 1, Townsend, L. B and Tipson, R. S., Ed., New York, 1978, p 211; Fischer, U.; Wyss, P. C. Ger. Offen. 2735458, 1978, Chem. Abstr. 89:24726e, 1978; Fischer, U.; Wyss, P. C. Belg. 857512, 1978, Chem. Abstr. 89:44128q, 1978; Tapiero, C.; Imbach, J. L.; Panzicka, R. P., Townsend, L. B. J. Carbohyd. Nucleosides Nucleotides 1976, 3, 191), which was then further condensed with guanidine hydrochloride in the presence of sodium methoxide in methanol. In either case, the product, target compound 3, was obtained in 90% yield.

The following detailed methodology was followed. H NMR spectra were recorded on a General Electric QE-300 (300 MHz) instrument. The spectral data are reported in the following format: chemical shift (all relative to $Me_4Si$ as an internal reference standard unless otherwise indicated), multiplicity (s=singlet, d=doublet, dd doublet of doublets, t=triplet, q=quartet, m=multiplet, b=broad integration, coupling constants, exchangeability after $D_2O$ addition, and assignment of resonances. Elemental Microanalyses were performed by Atlantic Microlab, Inc., Norcross, Ga. The mass spectra were recorded at the Mass Spectral Facility, Department of Biochemistry, Michigan State University. Thin layer chromatography was performed on Merck Kieselgel 60 $GF_{254}$ plates (0.2 mm thickness). Melting points were determined on a Thomas-Hoover capillary melting point apparatus and are uncorrected.

6-Imino-6H-1-β-D-ribofuranosyl-4,5,7,8-tetrahydroimidazo[4, 5-e][1,3]diazepine-4,8-dione Guanidine hydrochloride (0.38 g, 4 mmol) was added to 4 mL of 2.3 M sodium methoxide solution resulting from sodium (0.75 g) dissolved in 15 mL of absolute methanol. The mixture was stirred in an ice bath for 30 min. The precipitated sodium chloride was removed by filtration, and the filtrate was poured into a solution of methyl 1-(2,3,5-tri-O-benzoyl-β-D-ribofuranosyl)-4,5-imidazoledicarboxylate (compound 2, FIG. 4) (0.63 g, 1 mmol) in 20 mL of absolute methanol. The mixture was stirred at room temperature for 24–48 h when a TLC analysis showed that the reaction was complete. The reaction mixture was filtered if necessary. The clear filtrate was neutralized with 2M hydrochloric acid. The resulting precipitate was filtered and washed with water and methanol to give product 3 (0.28 g, 90%) as a white solid. An analytically pure sample was obtained by preparative TLC of the reaction mixture (silica gel, chloroform-methanol-30% ammoniun hydroxide (2:2:1), Rf 0.35), mp>250° C.; $^1$H NMR (DMSO-$d_6$) Δ 10.64 (brs, 1H, NH, exchangeable with $D_2O$), 8.59 (s, 1H, imidazole), 7.47 (brs, 1H, NH, exchangeable with $D_2O$), 6.60 (brs, 1H, NH, exchangeable with $D_2O$), 6.40 (d, 1H, J=2.4 Hz, 1'-H), 5.44 (d, H, J=3.9 Hz, OH, exchangeable with $D_2O$), 5.17 (t, 1H, J=4.5 Hz, OH, exchangeable with $D_2O$), 5.06 (d, 1H, J=4.5 Hz, OH, exchangeable with $D_2O$), 4.07 (m, 2H, 2' and 3'-H), 3.91 (m, 1H, 4'-H), 3.73 (dd, 1H, J=12.3 and 2.7 Hz, 5'-H), 3.59 (dd, 1H, J=12.3 and 3.0 Hz, 5'-$H_2$); $^{13}$C-NMR (DMSO-$d_6$) Δ 59.98 (C-5'), 68.62 (C-3'), 76.14 (C-2'), 84.34 (C-4'), 90.25 (C-1'), 140.39 (C-2, 3a, 4, 8, 8a), 149.86 (C-6); FABMS m/z: 312 [$MH^+$].

Anal. Calcd. for $C_{11}H_{13}N_5O_6 \cdot 1.25H_2O$ (MW 333.77): C, 39.58; H, 4.68; N, 20.98. Found: C, 39.58; H, 4.65; N, 20.85.

Compound 3 (FIG. 4), was also prepared from compound 4 (FIG. 4) using an analogous procedure as described above for the synthesis using compound 2 (FIG. 4).

Antiviral Screening for Hepatitis B Virus Activity.

The anti-HBV assays were performed according to the published protocol of Korba and Milman, (Korba, B. E.; Milman, G. Antiviral Res., 15, 217 1991), using cultures of 2.2.15 cells. In brief, the assay consisted of (a) seeding the chronically HBV-producing human liver cells (Acs et al. Proc. Nat. Acad. Sci., 84, 464 1987) into 24-well tissue culture plates, and growing to confluence, (b) adding test compounds daily for a continuous 9-day period, harvesting culture media after day 9 and (c) lysing treated cells 24 hours following day 9 of treatment for the analysis of extracellular virion DNA and intracellular HBV genomic forms.

Thus, the target nucleoside Compound 3 (FIG. 4) was screened for anti-hepatitis B virus (anti-HBV) activity in the transfected hepatoma cell line 2.2.15. Nucleoside 3 showed potent anti-HBV activity in this cell line, with an $EC_{50}$ value of 0.17 μM and a low cellular toxicity, with a $CC_{50}$ value of 2.4 mM (TI>14,000).

In particular, the Compound 3 shows anti-Hepatitis B virus activity

Example 14

Inhibition of Hepatitis B Virus Replication in Cultured Human Hepatoblastoma Cells (Human Model Assay) as Demonstrated by the Following Compounds:

Compound 14-1: 6-Imino-6H-1-β-D-ribofuranosyl-4,5,7,8-tetrahydroimidazo[4,5-e][1,3]diazepine-4,8-dione;

[Formula IA, Wherein J, L, X, Z=N; K, U, Y, W=C; $R_1=R_5=O$; $R_3=NH$; $R_2=R_4=R_7=H$; $R_8=NONE$; and $R_6=$-1-β-D-Ribofuranosyl]

Compound 14-2: 4,8-Diamino-6H-6-imino-1-β-D-ribofuranosylimidazo[4,5-e][1,3]diazepine

[Formula IB, Wherein J, L, X, Z=N; K, U, Y, W=C; $R_1=R_5=NH_2$; $R_3=NH$; $R_7=H$; $R_2=R_4=R_8=$None; and $R_6=$1-β-D-Ribofuranosyl]

Modified purine analogs were prepared wherein the six membered ring of the natural purine heterocycle was expanded to a seven membered ring (Chen, H., et al., *Nucleosides Nucleotides*, 18: In Press, 1999; Wang, L., et al., *Nucleosides Nucleotides*, 13:2307–2320, 1994). The newly synthesized ring expanded heterocycles in Compound 14-1 and Compound 14-2 still maintain their planarity and aromaticity, the two characteristics which are common with natural purines heterocycle moiety in adenosine and guanosine analogs.

Figure 5:
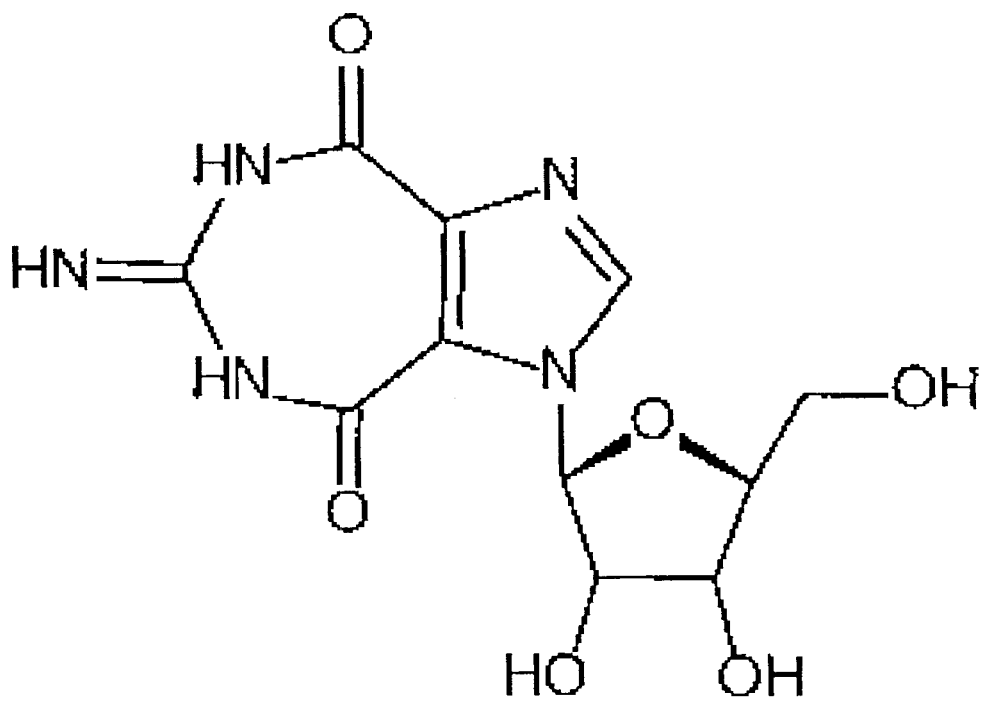
Figure 6:
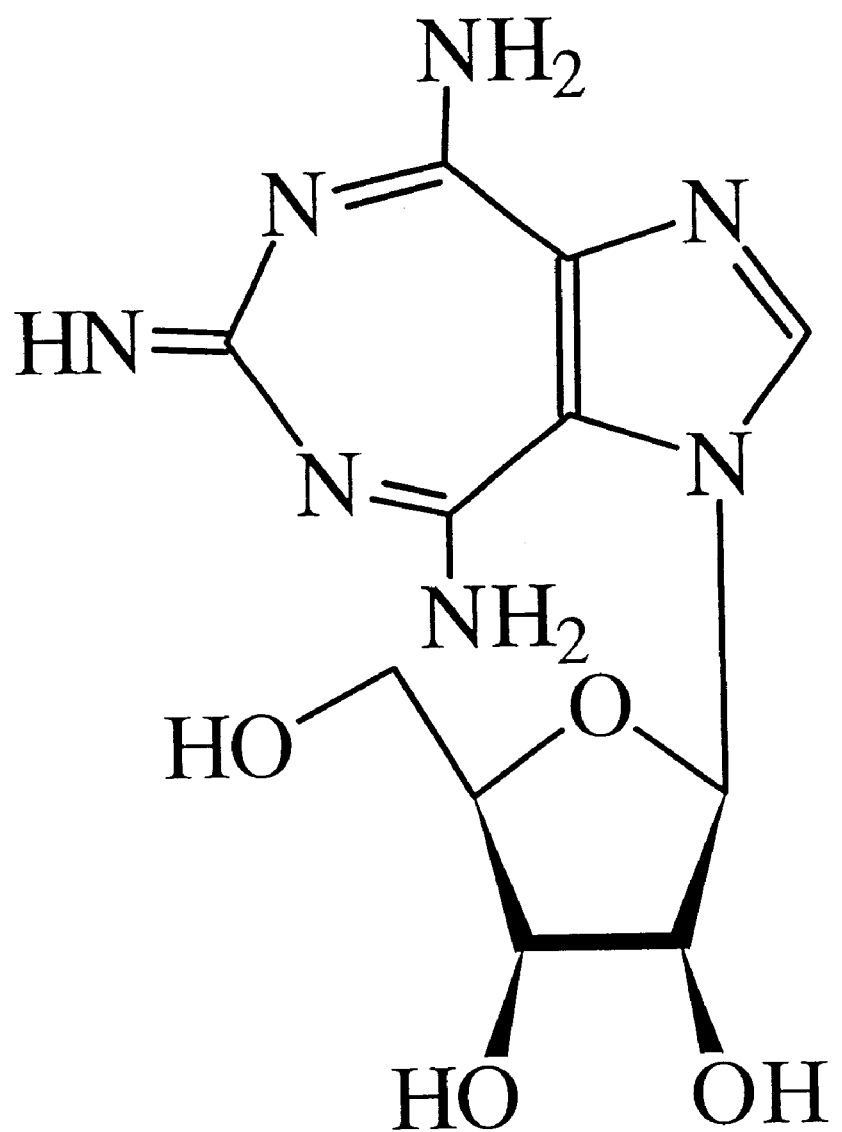

Antiviral activity was found for the riboside nucleoside analogs of these ring-expanded heterocycles. The two ring-expanded nucleosides (RENs), Compounds 14-1 and 14-2 (See FIG. 5 and FIG. 6, respectively), are selective inhibitors of intracellular HBV replication intermediate and extracellular HBV virion synthesis in chronically HBV-producing hepatoblastoma cells 2.2.15. These compounds are shown in this experiment to exhibit very low cellular toxicity in several stationary and rapidly growing cell systems.

The two RENs analogs, namely, 6-imino-6H-1-β-D-ribofuranosyl-4,5,7,8-tetrahydroimidazo[4,5-e][1,3]diazepine-4,8-dione (Compound 14-1) and 4,8-Diamino-6H-6-imino-1-β-D-ribofuranosylimidazo[4,5-e] [1,3] diazepine (Compound 14-2), were synthesized according to the procedures published previously; (Chen, H., et al., *Nucleosides Nucleotides*, 18: In Press, 1999; Wang, L., et al., *Nucleosides Nucleotides*, 13:2307–2320, 1994). Compounds 14-1 and 14-2 are structurally identical with the exception of substitution of the two exocyclic oxygen atoms on the seven membered ring of Compound 14-1 with two amino groups in Compound 14-2.

Anti-HBV activity and the toxicity against confluent 2.2.15 cells were determined by the previously described procedure (Korba, B. E., et al. *Antivir. Res.*, 19:55–70, 1992; Korba, B. E., et al. *Antivir. Res.*, 15:217–228, 1991). Briefly, confluent cultures of HBV transfected 2.2.15 cells were maintained on either 96-well or 24-well flat-bottomed tissue culture plates in RPMI 1640 medium with 2% fetal bovine serum (FBS). The cells were treated with test compounds daily for nine consecutive days. The culture media were harvested on day 9 to quantify the amount of virion DNA. On day 10, the cells were lysed to quantify the amount of intracellular HBV replicative intermediates (RI). The quantification of virion DNA and the HBV RI were done by blot hybridization methods (Korba, B. E., et al. *Antivir. Res.*, 19:55–70, 1992; Korba, B. E., et al. *Antivir. Res.*, 15:217–228, 1991). Cellular toxicity against separate cultures of confluent 2.2.15 cells was measured after treatment with the compounds for nine days under identical culture conditions as those used for the antiviral assay (Korba, B. E., et al. *Antivir. Res.*, 19:55–70, 1992). Uptake of neutral red dye by treated cells was compared with dye uptake by untreated control cells (Korba, B. E., et al. *Antivir. Res.*, 19:55–70, 1992).

The toxicity of Compounds 14-1 and 14-2 was also measured in rapidly growing human foreskin fibroblast (HFF) cells and Daudi cells by cell proliferation assay (National Institute of Allergy and Infectious Diseases (NIAID), NIH, Bethesda, Md.). According to the assay method, the appropriate cells were seeded in six-well plates in MEM containing 10% FBS. Twenty four hours later, the cells were treated with several dilutions of the test compounds covering a range of 0.03–100 μg/ml. The plates were incubated in a $CO_2$ incubator at 37° C. for 72h. The cells were washed after removing the media and subsequently released from the plate wells by the addition of 1 ml of 0.25% trypsin. The contents in the wells were mixed, diluted with Isotone III and counted using a Coulter counter. The $CC_{50}$ values (concentration of compound giving 50% inhibition of cell proliferation) were calculated by linear regression analysis. Toxicity of Compound 14-1 was also evaluated in bone marrow precursor cells by previously published procedure (Sommadossi, J.-P., et al., *Biochem. Pharmacol.*, 44:1921–1925, 1992).

Both compounds exhibited potent in vitro activity against HBV as shown by the results in Table 14-1. Compounds 14-1 and 14-2 inhibited the synthesis of extracellular HBV virions and intracellular HBV DNA RI in 2.2.15 cells following 9 days treatment with these compounds. Compound 14-1 was the most active compound against HBV. The $EC_{50}$ value of Compound 14-1 for virion DNA inhibition was approximately two-to-three fold higher than 3TC, which has been recently approved in the United States and several other countries for use in humans as a therapeutic agent against chronic HBV infections. This assay was repeated three times and the average $EC_{50}$ and $EC_{90}$ values for HBV virion inhibition obtained were 0.172 M and 1.29 μM, respectively. The toxicity of Compound 14-1 and 3TC in this assay system was equivalent.

Compound 14-2, although less active than Compound 14-1, was also able to inhibit the extracellular HBV virion synthesis in 2.2.15 cells. Comparison of the antiviral activity of Compound 14-1 and Compound 14-2 shows that replacement of the amino groups on the seven membered heterocycle with oxygen increased the in vitro anti-HBV activity by 3 fold. More importantly, this change in the structure resulted in a decrease in the in vitro cellular toxicity of Compound 14-1 by 5 fold compared to toxicity of Compound 14-2 in confluent 2.2.15 cells.

These compounds were evaluated for their ability to inhibit viral RNA synthesis in 2.2.15 cells. Since HBV uses host cellular RNA polymerase II during the transcription of viral RNA from the covalently closed circular HBV DNA during its replication, any effect on the synthesis of viral RNA by these compounds would mean interference with the cellular RNA polymerase which could lead to unacceptable cellular toxicity. As shown below in Table 14-2, like 3TC, both Compounds 14-1 and 14-2 failed to inhibit the synthesis of viral 3.6 kb and 2.1 kb RNA by HBV in 2.2.15 cells. In spite of no suppression of viral RNA synthesis in the presence of these compounds, treatment of 2.2.15 cells with these compounds, unlike 3TC, resulted in the reduction of viral protein synthesis, especially that of the core antigen.

63TC, however, did not appear to affect a reduction in synthesis of any of the viral proteins.

In vitro cellular toxicity of Compounds 14-1 and 14-2 was evaluated in several stationary and rapidly growing cell systems. Toxicity of Compound 14-1 was also studied in bone marrow precursor cells (by erythroid burst forming units and granulocyte macrophage CFU) (Sommadossi, J.-P., et al., *Biochem. Pharmacol.*, 44:1921–1925, 1992). The toxicity results are given below in Table 14-3. In bone marrow precursor cells, Compound 14-1 had $CC_{50}$ values which are comparable to those exhibited by 3TC. In rapidly growing human HFF cells and Daudi cells, both compounds were found to be non-toxic in the 50–100 uM concentration range (National Institute of Allergy and Infectious Diseases (NIAID), NIH, Bethesda, Md.).

The antiviral activity exhibited by Compounds 14-1 and 14-2 was found to be specific against HBV. These compounds were also tested for their effects on HIV (Weislow, O., et al., *J. Natl. Cancer Inst.*, 81:577–586, 1989), herpes simplex virus (HSV)-1, HSV-2, cytomegalovirus (CMV), Varicella Zoster virus (VZV) and Epstein-Barr virus (EBV) replication (National Institute of Allergy and Infectious Diseases (NIAID), NIH, Bethesda, Md.). These compounds showed no antiviral activity against these viruses.

Thus, the ribosyl analogs of two novel ring-expanded purine ring systems were found to selectively inhibit HBV replication in 2.2.15 cells. Both compounds were also found to have low cellular toxicity in various stationary and rapidly growing cell systems. Both compounds are particularly effective in inhibiting human HBV replication with low toxicity. These nucleoside analogs are structurally unique compared with other nucleosides with anti-HBV activity. They all have an expanded ring system as their heterocycle moiety. Compound 14-1, which was most potent in inhibiting HBV replication showed inhibition of the synthesis of intracellular HBV replication intermediates and extracellular virion release in 2.2.15 cells with 50% effective concentration ($EC_{50}$) of 0.604 and 0.131 $\mu M$, respectively. Yet Compound 14-1 shows very low cellular toxicity.

TABLE 14-1

Antiviral activities of test compounds against HBV replication in 2.2.15 cells

| Compound | $CC_{50}$ $(\mu M)^a$ | $EC_{90}$ $(\mu M)^b$ Virion[c] | $EC_{90}$ $(\mu M)^b$ HBV $RI^d$ | $EC_{50}$ $(\mu M)^b$ Virion[c] | $EC_{50}$ $(\mu M)^b$ HBV $RI^d$ | Selectivity Index[e] Virion | Selectivity Index[e] HBV RI |
|---|---|---|---|---|---|---|---|
| 14-1 | 2427 | .989 ± .11 | 7.3 ± .7 | .131 ± .02 | .604 ± .07 | 18526 | 4018 |
| 14-2 | 501 | 4.7 ± .5 | — | .397 ± .03 | — | 1262 | — |
| 3TC | 2039 | .198 ± .02 | .922 ± .085 | .065 ± .01 | .172 ± .019 | 31863 | 11854 |

Appropriate concentrations of the test compounds were added daily for 9 days to the HBV producing 2.2.15 cells. Culture media were harvested and cells were lysed 24 hr. after day 9 for the analysis of extracellular virion and intracellular HBV RI. HBV Virion DNA and intracellular HBV DNA RI levels in the cells were measured by blot hybridization methods (southern and dot blot) using $^{32}[P]$ labeled HBV-specific probes (Korba 1991, 1992).
[a]$CC_{50}$, is the drug concentration at which a two-fold reduction of neutral red dye uptake from the average value in the untreated cultures was observed.
[b]$EC_{90}$ and $EC_{50}$ are concentrations which give 10 fold and 2 fold inhibition of viral DNA levels, respectively. Values presented (± standard deviation) were calculated by linear regression analysis using data combined from all treated cultures; standard deviations were calculated by using the standard error of regression generated from the linear regression analysis.
[c]Extracellular HBV virion DNA
[d]Intracellular HBV DNA replicative intermediates
[e]Selectivity index was calculated as $CC_{50}/EC_{50}$ ratio.

TABLE 14-2

Effect of RENs on the relative levels of HBV ribonucleic acids (RNA) and proteins in 2.2.15 cells.

| Compound (Conc.)[a] | Virion $DNA^d$ | HBV $RI^d$ | 3.6 Kb $RNA^{b,d}$ | 2.1 Kb $RNA^{b,d}$ | $HBsAg^{c,d}$ | $HBcAg^{c,d}$ | $HBeAg^{c,d}$ |
|---|---|---|---|---|---|---|---|
| Untreated | 100 ± 14 | 100 ± 8 | 100 ± 10 | 100 ± 12 | 100 ± 15 | 100 ± 10 | 100 ± 9 |
| Compound 14-1 | 4 ± 1* | 15 ± 2* | 89 ± 9 | 96 ± 7 | 67 ± 6 | 75 ± 4 | 50 ± 5* |
| (10 $\mu M$) | (3 ± 1) | (9 ± 1) | (94 ± 11) | (102 ± 10) | (92 ± 14) | (94 ± 6) | (90 ± 8) |
| Compound 14-2 | 1 ± 1* | 6 ± 1* | 103 ± 9 | 96 ± 8 | 108 ± 18 | 109 ± 6 | 8 ± 3* |
| (10 $\mu M$) | (0) | (5 ± 1) | (97 ± 7) | (119 ± 11) | (88 ± 6) | (100 ± 8) | (95 ± 8) |

Cultures were treated for nine days as explained in Table 14-1. For each treatment, a total of 4 separate cultures were used for the analysis of each marker. The values reported are the levels of the indicated HBV markers at the end of the treatment period (day 9) expressed as a percentage (± standard deviation) of the average levels in the control cultures.
A "*" indicates that the value presented is significantly different from control values (P < 0.05), using a one-tailed T test with corrections for small numbers to assign Fisher's probability value.
[a]Concentrations of antiviral agents used in each case approximate $EC_{90}$ to $EC_{95}$ values of the individual agents against HBV DNA RI.
[b]HBV nucleic acid levels were measured by standard blot hybridization.
[c]HBV protein levels were measured by standard semi-quantitative EIA methods.
[d]The values given in the parentheses are for 3TC which was used as a control.

TABLE 14-3

In vitro cellular toxicity of compound 1 in various rapidly growing cell systems.

| Cell System | $CC_{50}$ for Compound 14-1 | $CC_{50}$ for Compound 14-2 | $CC_{50}$ for Reference Compound. |
|---|---|---|---|
| 2.2.15 Cells | 2427 mM | 501 mM | 2039 mM (3TC) |
| Bone Marrow toxicity | | | |
| BFU-E | 57.5 mM | ND | 68.5 mM (3TC) |
| CFU-GM | 52.1 mM | ND | 59.9 mM (3TC) |
| Rapidly growing HFF cells | >100 mM | >100 mM | >100 mM (Aciclovir) / >40 mM (Ganciclovir) |
| Rapidly growing Daudi cells | >50 mM | >50 mM | >50 mM (Aciclovir) |

Toxicity in bone marrow progenitor cells was measured according to the procedure published previously (Sommadossi)
Toxicity in HFF and Daudi cells was measured by cell proliferation assay. The cells were treated with several dilutions of test compounds for 72 h. The cells were released from the plate by trypsin treatment and counted using coulter counter. $CC_{50}$ values were calculated by linear regression analysis.

Example 15

Inhibition of Bacteriophage T7 RNA Polymerase, and Potent Anti-Hepatitis B Viral Activity, by the (Compound 15-1), 4,8-Diamino-6H-6-imino-1-β-D-ribofuranosylimidazo[4,5-e][1,3]diazepine and its 5'-Triphosphate Derivative (Compound 15-2).

[Compound 15-1=Formula IB, Wherein J, L, X, Z=N; K, U, Y, W=C; $R_1=R_5=NH_2$; $R_3=NH$; $R_7=H$; $R_2=R_4=R_8=$None; and $R_6$=1-β-D-Ribofuranosyl]

Figure 7:
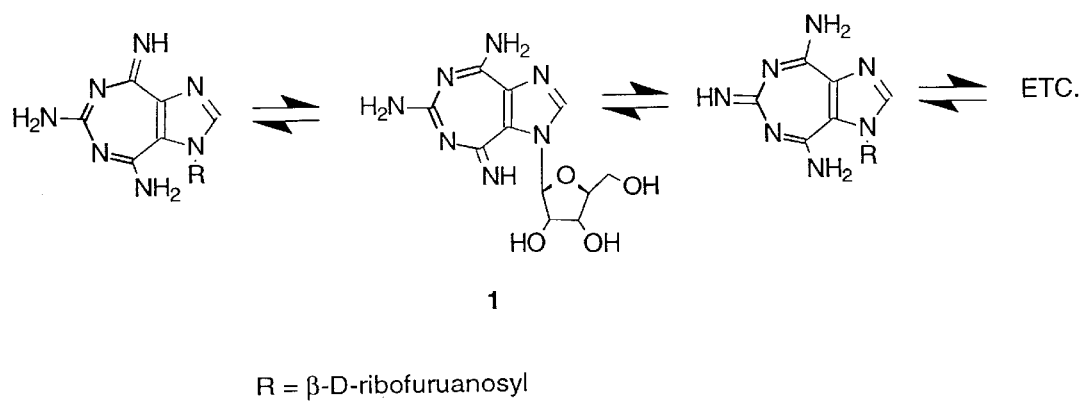

The diamino-imino-substituted "fat" nucleoside, Compound 15-1, shown in FIG. 7 (in tautomeric form) is substantially the same as the Compound 14-2 employed in EXAMPLE 4, i.e. 4,8-Diamino-6H-6-imino-1-β-D-ribofuranosylimidazo[4,5-e][1,3]diazepine. Compound 15-1 can be named as 4,6-diamino-8-imino-8H-1-β-D-ribofuranosylimidazo[4,5-e][1,3]diazepine. As described earlier, it has potent in vitro anti-hepatitis B viral activity with minimum toxicity. Compound 15-1. The synthesis of Compound 15-1 was previously stated in Example 4 of the present application. The substitution pattern written in Example 4 is that of the tautomeric form. Triphosphate of Compound 15-1 was also contemplated.

As earlier described, the nucleoside Compound 15-1 was not the most potent of the "fat" nucleosides that exhibited anti-hepatitis B viral activity, but it served as a basic prototype for studying inhibition of enzymatic activity of polymerases by ring expanded nucleosides.

This choice was based upon several considerations:

(a) the synthesis of Compound 15-1 is simple, short (only three steps), and efficient, (b) the compound is reasonably stable to normal physiological and biochemical experimental conditions, (c) nucleoside, Compound 15-1, is planar as suggested by molecular modeling (Molecular modeling of Compound 15-1 was carried out using InsightII (Biosym) from Molecular Simulations, Inc. (MSI), San Diego, Calif.) and is potentially aromatic, (The seven-membered ring of Compound 15-1 could be considered as a substituted diazatropone or diazatropolone, while the heterocyclic ring of Compound 15-1 as a whole can be compared with a substituted polyazaazulene). The bicyclic ring has a total of ten π electrons to obey the Hückel rule as well)

(d) a planar, larger surface area of Compound 15-1 as compared to that of purines may, in addition, result in enhanced hydrophobic interactions with nucleic acid bases if Compound 15-1 gets incorporated into nucleic acid double-helices, and (e) the compound is theoretically capable of existing in several tautomeric forms in solution as shown above, and depending upon what particular tautomeric form it assumes, Compound 15-1 can mimic adenine, guanine, and/or isoguanine, in addition to 2,6-diaminopurine to which it has the best structural resemblance.

The last three features mentioned under items c, d, and e offer several routes for investigating the inhibition of enzymatic activity of polymerases by ring expanded nucleosides, including:

(a) that Compound 15-1 could be phosphorylated in vivo by kinases to its 5'-triphosphate derivative, and subsequently incorporated into viral nucleic acids during transcription of viral DNA by an RNA polymerase, and cause DNA distortion, ultimately leading to chain termination, (b) that Compound 15-1 could bind to an active or allosteric site of the polymerase, either as a nucleoside or nucleotide, and cause competitive or non-competitive inhibition, or (c) that Compound 15-1 could be a substrate or inhibitor of any or several of the enzymes of purine metabolism, mimicking one of the natural purines, and thus act as an effective antimetabolite or inhibitor.

The most commonly employed template-dependent RNA-polymerase for biochemical investigations and preparations of RNA transcripts is T7 RNA polymerase from bacteriophage T7. (Kochetkov, et al., *FEBS Lett.* 440, 264–267, 1998) Studies with modified nucleosides with this enzyme have been limited. It has been shown to accept base-modified nucleotides as substrates, provided adequate base-pairing is maintained, even though not of the Watson-Crick type. (Switzer, C., et al. *J. Am. Chem. Soc.*, 111, 8322–8323, 1989) Thus, base pairs between isoguanosine and isocytidine, and also between xanthosine and diaminopyrimidine nucleosides can be formed using the appropriate template. (Switzer, C., et al. *J. Am. Chem. Soc.*, 111, 8322–8323, 1989; Piccirilli, J. A., et al., *Nature*, 343, 33–37, 1990) With templates containing the 2'-deoxy-1-methylpseudouridine ($d^m\Psi$), T7 RNA polymerase catalyzes the incorporation of either adenosine triphosphate or formycin triphosphate into a growing chain of RNA with the same efficiency as with templates containing thymidine. (Piccirilli, J. A., et al., *Biochemistry*, 30, 10350–10356, 1991) In each case, the overall rate of synthesis of full-length products containing formycin is about one-tenth the rate of synthesis of analogous products containing adenosine. (Piccirilli, J. A., et al., *Biochemistry*, 30, 10350–10356, 1991) The sugar-modified nucleotide analogues, 2'-fluoro-2'-deoxynucleoside-5'-triphosphate and 2'-amino-2'-deoxyuridine-5-triphosphate, are substrates for T7 RNA polymerase. Transcription of two tRNA genes showed that such templates can be transcribed to full-length products essentially without premature termination with any of the analogues. (Aurup, H., et al., *Biochemistry*, 31, 9636–9641, 1992) On the other hand, there are also known analogues of nucleotides which can inhibit the synthesis of RNA without being incorporated into RNA. For example, 5-formyl-1-(α-D-ribofuranosyl)uracil-5′-triphosphate is a noncompetitive inhibitor of *Escherichia coli* DNA dependent RNA polymerase. (Armstrong, V., et al., *Biochemistry*, 15, 2086–2091, 1976) The inhibition is presumably due to Schiff base formation between an amino group on the enzyme and the formyl group, and is reversible. The effect of the regulatory nucleotide ppGpp on transcription by *Escherichia coli* RNA polymerase has been studied by Kingston, et al. (Kingston, R. E., et al., *J. Biol. Chem.*, 256, 2787–2797, 1981) They concluded that ppGpp appears to slow down the transcriptional elongation by binding to RNA polymerase and altering its structure in a manner that impedes the passage of the enzyme through certain DNA sequences.

Effects on the Synthesis of RNA Transcripts by Bacteriophage T7 RNA Polymerase

The following describes the effects of 4,6-diamino-8-imino-8H-1-β-D-ribofuranosylimidazo[4,5-e][1,3]diazepine (Compound 15-1) and its 5′-triphosphate derivative, Compound 15-2, on the synthesis of RNA transcripts by bacteriophage T7 RNA polymerase.

Chemistry

Nucleoside Compound 15-1 was synthesized using the above described procedure (see Example 4; Wang, L., et al., *Nucleosides Nucleotides*, 13:2307–2320, 1994), except that four equivalents of guanidine instead of equimolar amounts of guanidine and 4,5-dicyanoimidazole were employed for condensation to prepare the required heterocyclic base 4,6,8-triaminoimidazo[4,5-e][1,3]diazepine in a consistently high yield of 80% or more.

Figure 8:
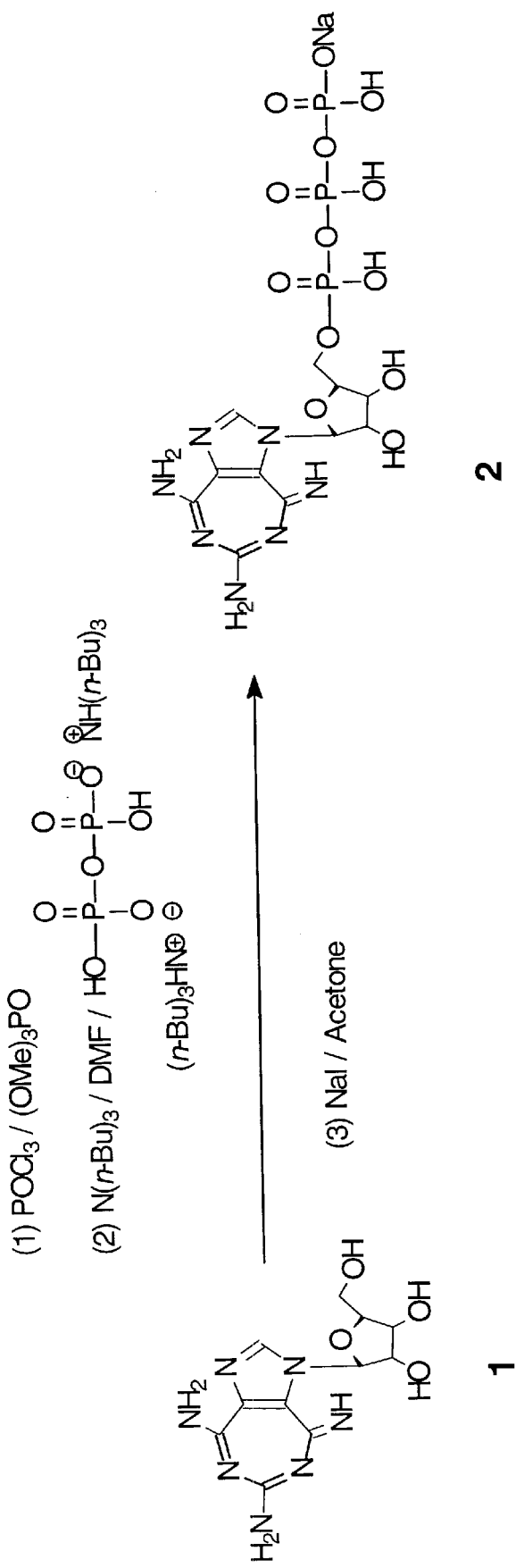

The Vorbrüggen ribosylation, (Vorbrüggen, H., et al., *Chem. Ber.*, 114, 1279–1286, 1981; Vorbrüggen, H. et al., *Chem. Ber.*, 114, 1234–1255, 1981) followed by deprotection of the sugar hydroxyls, as reported in the published procedure, afforded Compound 15-1 in ≧77% overall yield for the two steps. The method of Vrang, et al. (Vrang, L., et al., *Antiviral Research*, 7, 139–149, 1987) was employed for phosphorylation of Compound 15-1 (see FIG. 8), which included (a) treatment with phosphorous oxychloride to phosphorylate the 5′-hydroxyl function, and (b) condensation with bis(tributylammonium) pyrophosphate at 0° C. to form the triphosphate. The yield was ~50%, but during purification on DEAE -Sephadex A-25 column using TEAB buffer, partial decomposition of the 5′-triphosphate was observed. The compound was isolated in a pure form by preparative TLC on cellulose plates, using methanol-water (7:3) as the developing solvent. The compound was precipitated as a sodium salt with NaI in acetone, giving the target 5′-triphosphate derivative Compound 15-2. The latter was characterized by $^1$H and $^{31}$P NMR, as well as by high resolution mass spectral data.

RESULTS

Assessment of Incorporation of "Fat" Nucleoside-5′-triphosphate (FNTP, Compound 15-2) During Transcription Catalyzed by T7 RNA Polymerase.

To show whether the "fat" nucleotide Compound 15-2 (FNTP) is incorporated into RNA during transcription, experiments were performed using bacteriophage T7 RNA polymerase (RNAP) and a synthetic 42-mer DNA template shown below that is annealed to a 17-nucleotide promoter specific for T7 RNAP. This promoter-template enables the synthesis of 25-mer RNA, and the purine analogue may be incorporated in positions +1, +11, +13, +15, +21, +22, and +23.

5′T AATACG ACTCAC TAT A
3′A TTA TGC TGA GTG ATA TCG GAA GGA AGC ACG TGG GAG CTT AA 3′

Figure 9:
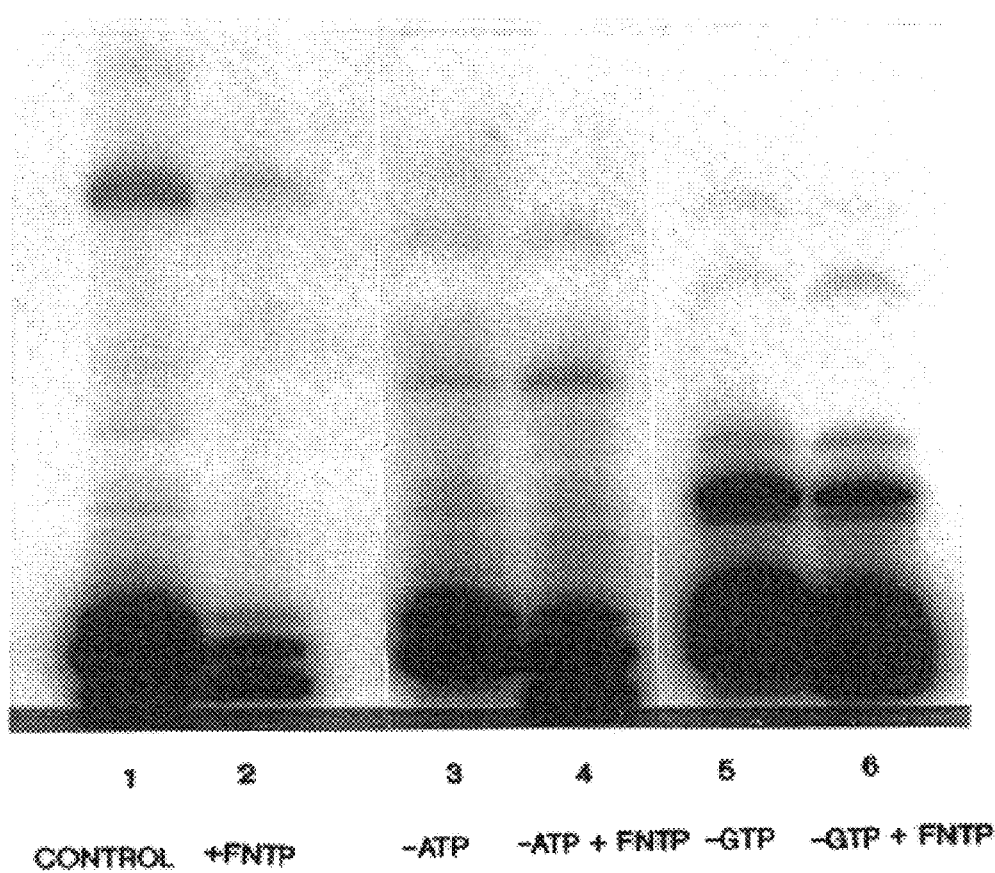

Transcription reaction conditions were optimized with the use of $^{32}$P CTP for labeling RNA transcripts. Polyacrylimide gel electrophoresis of the transcription products obtained from the 42-mer template, using 1 mM each of four natural NTPs, reveled a 25-mer RNA as the major product, together with shorter and longer labeled transcripts (FIG. 9, lane 1). The additional bands observed are consistent with the known ability of T7 RNA polymerase to add non-coded residues at the 3′-end of transcripts. (Milligan, J. F., et al., *Nuc. Acids Res.*, 15, 8783–8798, 1987) With the use of 1 mM nucleotide Compound 15-2 (FNTP), the yield of transcription was reduced (lane 2).

The relative ability of nucleotide Compound 15-2 to act as an incoming ATP or GTP was assessed by comparison of reactions without ATP or GTP. In the absence of ATP (lane 3), when only CTP, GTP and UTP were used, a 14-mer RNA was synthesized as the major product, as expected. When nucleotide Compound 15-2 was used, (lane 4), the 14-mer RNA was once again seen as the major product, and none of the longer transcripts were observed to indicate that nucleotide Compound 15-2 is being incorporated.

In the absence of GTP (1 mM GMP was used to initiate the synthesis of RNA) (Figure, lane 5), a 10-mer was seen as the major product. When nucleotide Compound 15-2 was used (lane 6), a 10-mer RNA was again seen as the major product, and the extent of synthesis was reduced as well. These results show that nucleotide Compound 15-2 is not a substrate for T7 polymerase.

Assessment of Inhibition of the T7 RNA Polymerase-Catalyzed Transcription by "Fat" Nucleoside-5′-triphosphate (FNTP, Compound 15-2).

With the use of a synthetic 37-mer DNA template, annealed to a 17-nucleotide promoter for T7 RNAP as shown below, a 20 nucleotide-long transcript RNA was obtained when the reaction mixture contained all four NTPs in appropriate concentrations, along with many shorter "abortive" fragments. (Milligan, J. F., et al., *Nuc. Acids Res.*, 15, 8783–8798, 1987). For the reaction with modified nucleotide, typically

5′TAATACGACTCACTATA
3′ATTA TGC TGA GTG ATA TCC TGA TCG CCT CCG ATC AGG 5′ the concentration of the appropriate natural nucleotide was reduced. (Aurup, H., et al., *Biochemistry*, 31, 9636–9641, 1992) This strategy is however less effective if the analogue is one of the first nucleotides in the transcript because of the large number of "abortive" initiation products. (Milligan, J. F., et al., *Methods in Enzymol.*, 180, 51–63, 1989.) In the present experiments, the synthesis of RNA was compared under standard conditions (using 4 NTPs in 0.2 mM concentration each) with the synthesis of RNA by using an additional "fat" nucleoside triphosphate Compound 15-2 (FNTP) in varying (0.05–10 mM) concentrations. The reaction mixtures were incubated at 37° C. for 2 hours, and the products were denatured in a buffer containing urea. The products were separated by 20% polyacrylamide-urea gel electrophoresis and visualized by autoradiography.

Figure 10:
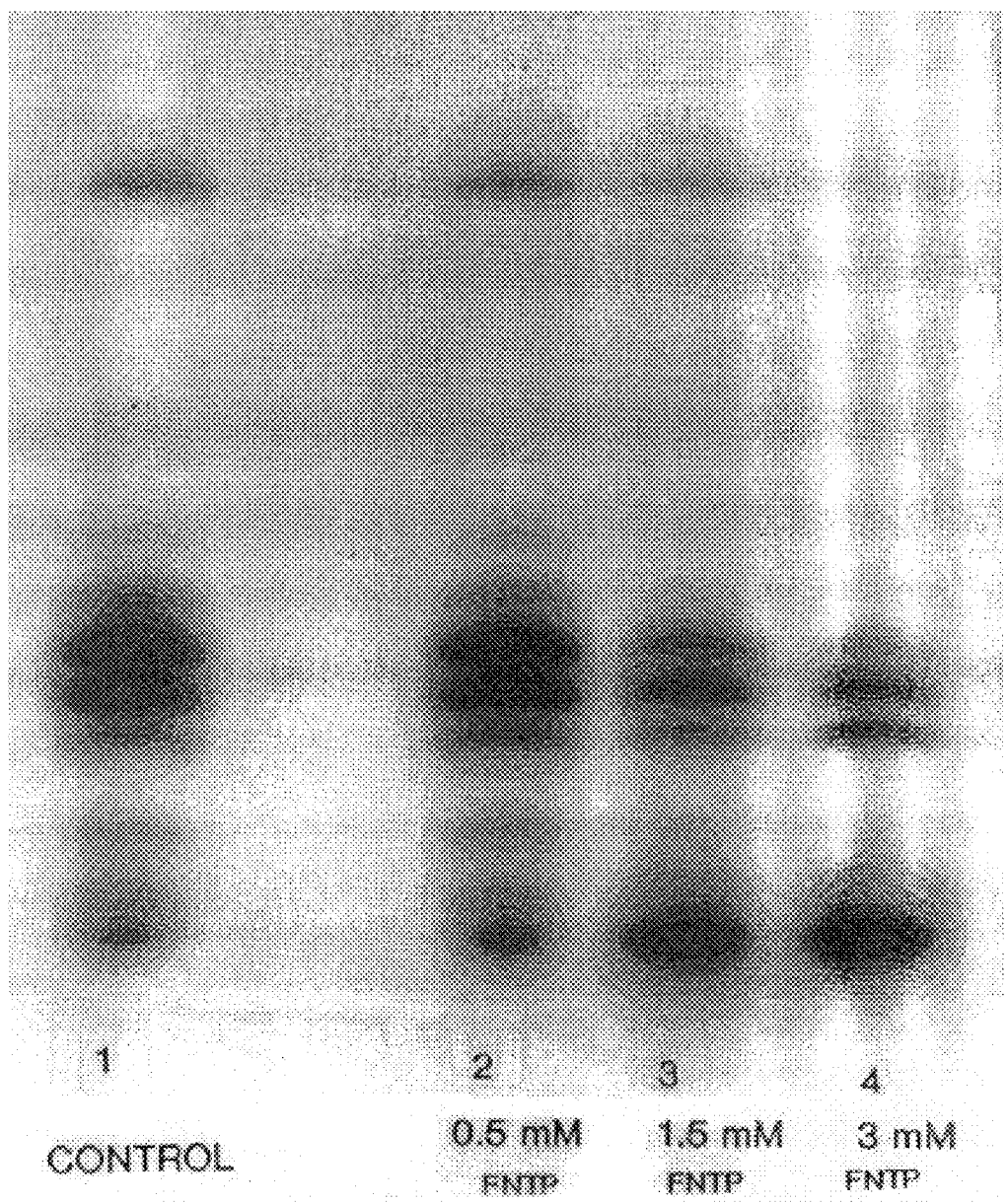

FIG. 10 is an autoradiogram of a typical gel in which the products of the four reactions were analyzed. With autoradiography, the bands of the long 20-mer RNA along with those of abortive shorter fragments could be seen (FIG. 10, lane 1). In the reactions with "fat" nucleotide Compound 15-2, the bands of long RNA were increasingly less intensive with increasing concentrations of nucleotide Compound 15-2 (lanes 2–4).

Figure 11:
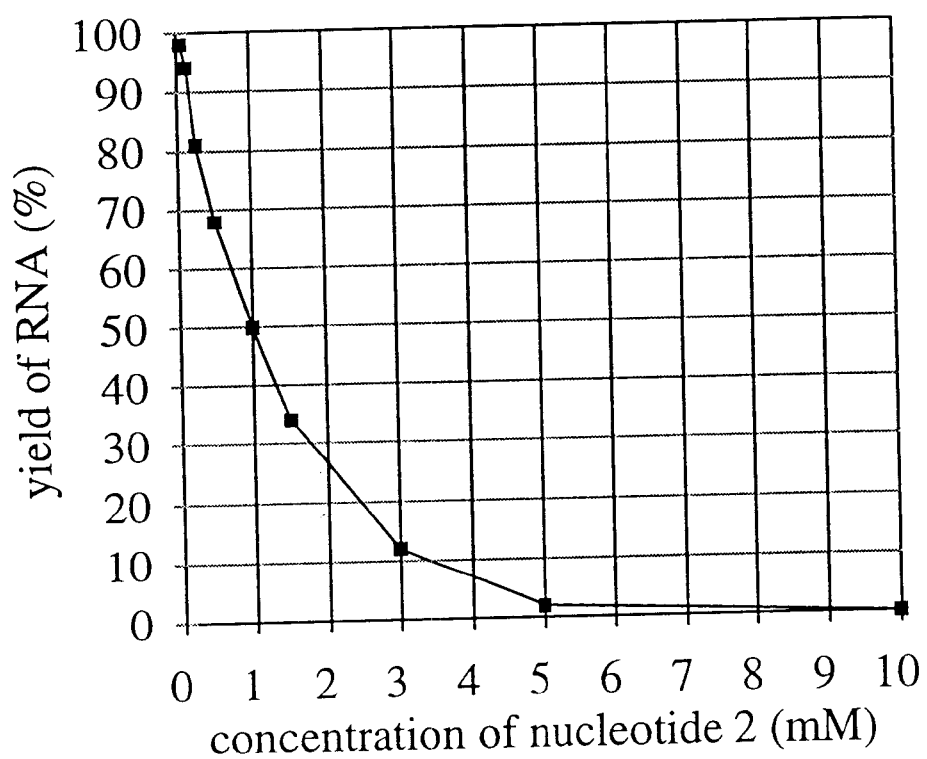

The quantitation of the products formed was carried out either by (laser) scanning densitometry of autoradiograms of the [$\alpha^{32}$P]GTP-labeled transcripts that were analyzed by gel electrophoresis, or with the use of the PhosphorImager screen. The assayed yields of transcription at varying concentrations of nucleotide Compound 15-2 are presented as percentages of the values obtained with the absence of nucleotide Compound 15-2 (FIG. 11).

Effect of Nucleoside Compound 15-1 on Transcription Catalyzed by T7 RNA Polymerase.

As there was no evidence that the nucleotide Compound 15-2 gets incorporated into RNA during the transcription of a DNA template by T7 RNA polymerase, as delineated above, a test was performed to determine if the 5'-triphosphate derivative would at all be necessary for the inhibition. Accordingly, the above transcription experiments were repeated using nucleoside Compound 15-1 in place of nucleotide Compound 15-2. The autoradiograms of the polyacrylamide gels clearly indicated that there was neither incorporation nor inhibition by Compound 15-1 upon transcription.

Conclusion

The ring-expanded nucleoside Compound 15-1, exhibited a potent in vitro anti-HBV activity with low toxicity. T7 RNA polymerase inhibitory activity of the triphosphate Compound 15-2 was demonstrated in an in vitro assay. The transcriptions of two DNA templates (a 42-mer and a 37-mer template) were tested in the presence and absence of nucleotide Compound 15-2, using the bacteriophage T7 RNA polymerase. The results show that nucleotide Compound 15-2 is an inhibitor of T7 polymerase, but there is no indication that Compound 15-2 is being incorporated into RNA during transcription.

However, since nucleoside Compound 15-1 itself failed to cause inhibition of the transcription, the in vivo phosphorylation of nucleoside Compound 15-1 to its 5'-triphosphate derivative by kinases is critical for the observed inhibition of T7 RNA polymerase activity. Thus, the nucleotide Compound 15-2 may simply be binding to the polymerase at an active or allosteric site to cause inhibition without actually being incorporated into the developing nucleic acid during the transcription process. Compounds 15-1 and 15-2 are particularly effective in inhibiting human T7 RNA polymerase.

Methodology for the Above Experiments Chemistry $^1$H NMR spectra were recorded on a General Electric QE-300 (300 MHz) instrument. $^{31}$P NMR spectra were run on a Bruker Avance 600 MHz instrument operating at 242.93 MHz for phosphorus nucleus. The chemical shift data are reported with reference to Me$_4$Si for H NMR and to H$_3$PO$_4$ for $^{31}$P NMR, used as internal and external standards, respectively, and are shown in the following format: chemical shift, multiplicity (s=singlet, d=doublet, and m=multiplet), integration, coupling constants, and assignment of resonance. The mass spectral data were obtained from the Mass Spectral Facility, Department of Biochemistry, Michigan State University, East Lansing, Mich. Thin layer chromatography was performed on Merck Kieselgel 60 GF$_{254}$ plates (0.2 mm thickness). Melting points were determined on a Thomas-Hoover capillary melting point apparatus, and are uncorrected.

Synthesis of 4,6-Diamino-8-imino-8H-1-β-D-ribofuranosylimidazo[4,5-e][1,3]diazepine-5'-phosphate (2).

To an ice-cold suspension of nucleoside Compound 15-1 (77 mg, 0.2 mmol) in 0.7 mL of trimethyl phosphate, 80 μL (0.85 mmol) of phosphorous oxychloride was added. The mixture was stirred at 0° C. for 5 h, until all precipitate had dissolved. Then a solution of bis(tributylammonium) pyrophosphate (782 mg, 1.95 mmol) in 1.5 mL of dry DMF and 0.4 mL (1.95 mmol) of dry tributylamine was added, and the mixture was stirred in an ice-bath for 30 min. The reaction mixture was quenched by addition of triethylammonium hydrogen carbonate (TEAB) buffer (1M, pH 7.5) so as to adjust the pH to about 7. The solution was extracted with EtOAc and the aqueous layer (~20 mL) was loaded onto the DEAE Sephadex A-25 column (40×2.5 cm) which was pre-equilibrated with 0.01 M TEAB buffer. The column was subsequently eluted with a linear gradient of TEAB buffer (0.01–1 M, 1200 mL). The fractions were monitored by TLC (i-propanol-conc. NH$_4$OH-water, 7:1:2). Appropriate UV-absorbing fractions were pooled and evaporated. The residue was purified by preparative TLC on Cellulose F plates, using a mixture of methanol-water (7:3) as the developing solvent. The product 5'-triphosphate obtained from the prep-TLC was dissolved in 3 mL of water and reprecipitated with 100 mg of NaI in 10 mL of acetone. The precipitated sodium salt was collected by centrifugation, washed with acetone, and dried over P$_2$O$_5$ to yield Compound 15-2 (20 mg, 17.5%), and was stored in a –20° C. freezer: R$_f$ (silica gel, i-propanol-conc. NH$_4$OH-water, 7:1:2.) 0.06; $^1$H NMR (D$_2$O) δ 8.5 (s, 1H, H-2); 6.1 (d, 1H, sugar H-1'), 4.48 (m, 1H, sugar H), 4.13 (m, 1H, sugar H), 3.74 (m, 1H, sugar H), 3.53–3.21 (m, 2H, sugar 5'-H); $^{31}$P NMR (D$_2$O) δ −6.41 (γ-P), −7.89 (α-P), −20.16 (β-P); UV (pH 7) $\lambda_{max}$ 246 nm (ζ-32,000); Mass Spectrum (FAB) m/z 572 (MH$^+$), HRMS Calcd. for C$_{11}$H$_{18}$O$_{13}$N$_7$P$_3$Na: 572.0073. Found: 572.0079.

Transcription Reactions: General

Nucleoside triphosphates were purchased from Sigma, dissolved in water to concentration of 50 mM adjusted to pH 8 with 1M NaOH, and then stored at −20° C. [($\alpha^{32}$P]-ATP and [$\alpha^{32}$P]-GTP (specific activity 10 μCi/μL) were purchased from Amersham. Synthetic DNAs were from GIBCO BRL, Life Technologies; Inc, Gaithersburg Md. DNAs were PAGE purified, and their concentrations were determined spectrophotometrically.

The template promoters were annealed by heating to 80° C. in 10 mM Tris-HCl pH 8, 1 mM EDTA, and slow cooling to room temperature at a final concentration of 2.5 uM. The bacteriophage T7 polymerase (20 units/μL) was purchased from Promega-P2075. Kodak XAR-5 films were employed for autoradiography.

Transcription Reaction Conditions and Procedures

Transcription samples (total volume 10 μL contained: 40 mM Tris-HCl pH 8.1 with 6 mM MgCl$_2$, 5 mM dithiothreitol (DTT), 1 mM spermidine, 0.01% Triton-X 100, 50 μg/mL bovine serum albumin, 250 nM synthetic DNA template with a promotor for T7 RNAP, 4 units of T7 RNA polymerase, and 0.2 mM ribonucleoside triphosphates. A single $\alpha^{32}$P-labeled NTP was added for labeling (typicallly 1 μL of 10 mCi/mL). Inhibition assays were monitored with varying concentrations (0.05–10 mM) of nucleotide Compound 15-2. Polyacrylamide gel (20%) electrophoresis was performed on slab gels (18 cm×16 cm, or 35 cm×44 cm) containing 8M urea. (Sambrook, J., et al, *Molecular Cloning: A Laboratory Manual*, Second Ed., 1989) Gels were pre-run (400 V for 2 h) and then run at 400 V for 2–3 h or at 1000 V overnight after application of samples. Bands were visualized by autoradiography or by the use of phosphoriimiger screen.

Example 16

Anti-Cancer Effects of the following compounds of the present invention:

Compound 16-1: 6-Imino-6H-1-β-D-ribofuranosyl-4,5,7,8-tetrahydroimidazo[4,5-e][1,3]diazepine-4,8-dione

[Formula IA, Where J, L, X, Z=N; K, U, Y, W=C; $R_1=R_5=O$; $R_3=NH$; $R_2=R_4=R_7=H$; $R_8=NONE$; and $R_6=1$-β-D-ribofuranosyl]

Compound 16-2: 4,8-Diamino-6H-6-imino-1-β-D-ribofuranosylimidazo[4,5-e][1,3]diazepine

[Formula I(B), Where J, L, X, Z=N; K, U, Y, W=C; $R_1=R_5=NH_2$; $R_3=NH$; $R_7=H$; $R_2=R_4=R_8=None$; and $R_6=1$-β-D-ribofuranosyl]

Compound 16-2b: 4,8-Diamino-6H-6-imino-1(2',3',5'-tri-O-benzoyl-β-D-ribofuranosyl)imidazo[4,5-e][1,3]diazepine (Compound 16-2b is a Tribenzoylated Derivative of Compound 16-2)

[Formula I(B), Where J, L, X, Z=N; K, U, Y, W=C; $R_1=R_5=NH_2$; $R_3=NH$; $R_7=H$; $R_2=R_4=R_8=None$; and $R_6=2',3',5'$-tri-o-Benzoyl-1-β-D-ribofuranosyl]

Compounds 16-1, 16-2 and 16-2b were tested against a panel of cancer cell lines for their anti-cancer activity in an in vitro assay.

Procedure

The assay is conducted according to the procedure published previously (Monks, A. et al., J. Natl. Cancer Inst. 83,:757–766, 1991). Briefly, cell suspensions that were diluted according to the particular cell type and the expected target cell density (5000–40,000 cells per well based on cell growth characteristics) were added by pipette (100 μl) into 96-well microtiter plates. Inoculates were allowed a preincubation period of 24h at 37° C. for stabilization. Dilutions at twice the intended test concentrations of the test compounds were added at time zero in 100 μl aliquots to the microtiter plate wells. The plates were incubated for 48 h in 5% $CO_2$ atmosphere and 100% humidity. The cells were assayed by using the sulforhodamine B assay (Rubinstein, L. V. et al. J. Natl. Cancer Inst. 82:1113–118, 1990; Skehan, P. et al., J. Natl. Cancer Inst. 82:1107–1112, 1990). The plates were read by a plate reader. The following parameters were calculated from the optical densities:

$GI_{50}$, concentration of drug that causes 50% growth inhibition; where $(T-T_0)/(C-T_0) \times 100 = 50$ TGI, concentration of the drug that causes 100% growth inhibition; where $(T-T_0)/(C-T_0) \times 100 = 0$ $LC_{50}$, where $(T-T_0)/T_0 = -50$ where T=optical density after 48 h exposure to the test drug $T_0$=optical density at time zero C=control optical density after 48 h derived from wells without the addition of test compound.

Results

Figure 12:
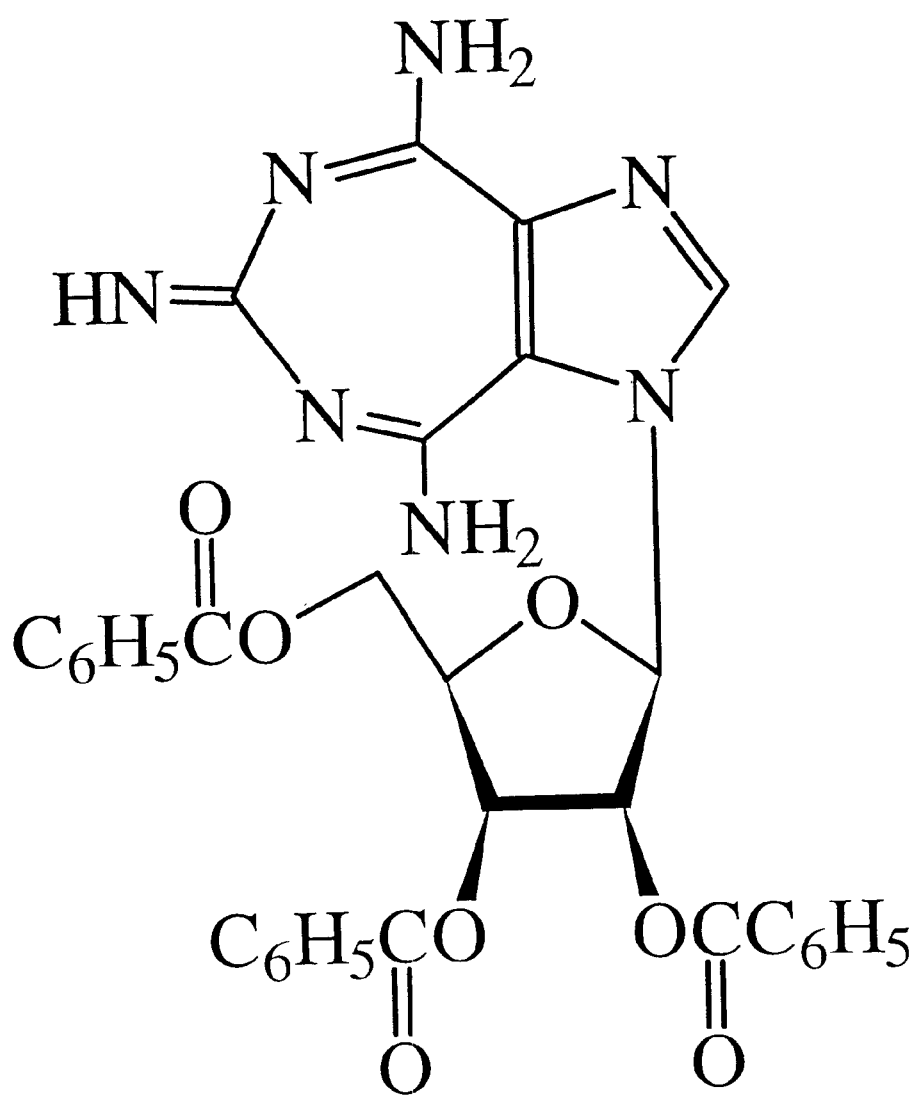

Compound 16-2b (structure shown in FIG. 12) and Compound 16-2 (structure shown in FIG. 6) demonstrated in vitro activity against several cancer cell lines, as shown by the test results in below Table 16-1 and Table 16-2, respectively). Compounds 16-1, 16-2 and 16-2b are particularly active in inhibiting human cancer. The test results showed anti tumor activity against leukemia, non-small cell lung cancer, colon cancer, CNS cancer, melanoma, ovarian cancer, renal cancer, prostate cancer and breast cancer cell lines with $GI_{50}$ values ranging between $10^{-5}$–$10^{-7}$ M and $10^{-5}$–$10^{-6}$ M, Compound 2b-1 and Compound 16-2 respectively. Compound 16-1, structure shown in FIG. 5 (see results in Table 16-3) showed selective activity against CNS cancer cell line SNB-75 ($GI_{50}=5\times10^{-7}$ M), breast cancer cell line MDA-MB-231 ($GI_{50}=5.6\times10^{-6}$ M) and renal cancer cell line RXF-393 ($GI_{50}=2.5\times10^{-5}$ M).

TABLE 16-1

Test Results for Compound 16-2b

| Panel/Cell Line | Log10 Concentration | | |
|---|---|---|---|
| | GI50 | TGI | LC50 |
| Leukemia | | | |
| CCRF-CEM | 1.25E-07 | 1.84E-06 | 6.40E-06 |
| HL-60(TB) | 4.01E-06 | 1.83E-05 | 8.37E-05 |
| K-562 | 2.74E-06 | >1.00E-04 | >1.00E-04 |
| MOLT-4 | 2.31E-06 | 7.08E-06 | >1.00E-04 |
| RPMI-8226 | 2.53E-06 | 7.42E-06 | >1.00E-04 |
| SR | 4.27E-06 | >1.00E-04 | >1.00E-04 |
| Non-Small Cell Lung Cancer | | | |
| A549/ATCC | 6.44E-06 | 3.00E-05 | >1.00E-04 |
| EKVX | 1.09E-05 | 2.96E-05 | 8.04E-05 |
| HOP-62 | 7.64E-06 | 2.27E-05 | 5.56E-05 |
| NCI-H226 | 6.89E-06 | 2.51E-05 | 7.24E-05 |
| NCI-H23 | 1.23E-05 | 2.77E-05 | 6.23E-05 |
| NCI-H322M | 8.38E-06 | 2.40E-05 | 6.24E-05 |
| NCI-H460 | 2.52E-06 | 8.42E-06 | 3.47E-05 |
| Colon Cancer | | | |
| COLO-205 | 1.49E-06 | 2.87E-06 | 5.55E-06 |
| HCC-2998 | 3.18E-06 | 6.41E-06 | 1.92E-05 |
| HCT-116 | 3.76E-06 | 2.12E-05 | 8.75E-05 |
| HCT-15 | 5.77E-06 | 1.95E-05 | 5.08E-05 |
| HT29 | 2.58E-06 | 1.03E-05 | 4.23E-05 |
| KM12 | 5.50E-06 | 1.94E-05 | 5.36E-05 |
| SW-620 | 5.14E-06 | 2.95E-05 | >1.00E-04 |
| CNS Cancer | | | |
| SF-268 | 1.32E-05 | 3.13E-05 | 7.42E-05 |
| SF-295 | 6.03E-06 | 1.96E-05 | 4.92E-05 |
| SNB-19 | 1.47E-05 | 3.16E-05 | 6.82E-05 |
| SNB-75 | 1.23E-05 | 2.49E-05 | 5.04E-05 |
| Melanoma | | | |
| LOX IMVI | 3.01E-06 | >1.00E-04 | >1.00E-04 |
| MALME-3M | 3.04E-06 | 8.07E-06 | 3.38E-05 |
| M14 | 1.91E-06 | 3.54E-06 | 6.54E-06 |
| SK-MEL-2 | 2.60E-06 | 6.87E-06 | 2.62E-05 |
| SK-MEL-28 | 1.04E-05 | 2.62E-05 | 6.58E-05 |
| SK-MEL-5 | 1.36E-06 | 2.64E-06 | 5.16E-06 |
| UACC-257 | 4.51E-06 | 1.83E-05 | 7.35E-05 |
| UACC-62 | 1.56E-05 | 3.34E-05 | 7.15E-05 |
| Ovarian Cancer | | | |
| IGROV1 | 5.13E-06 | 2.03E-05 | 6.67E-05 |
| OVCAR-3 | 1.09E-05 | 2.30E-05 | 4.87E-05 |
| OVCAR-4 | 1.38E-05 | 2.80E-05 | 5.70E-05 |
| OVCAR-5 | 1.57E-05 | 3.01E-05 | 5.77E-05 |
| OVCAR-8 | 4.34E-06 | 2.25E-05 | >1.00E-04 |
| SK-OV-3 | 1.63E-05 | 3.05E-05 | 5.70E-05 |
| Renal Cancer | | | |
| 786-0 | 1.55E-05 | 3.56E-05 | 8.15E-05 |
| A498 | 2.00E-05 | 3.78E-05 | 7.18E-05 |
| ACHN | 1.09E-05 | 2.35E-05 | 5.07E-05 |
| CAKI-1 | 1.21E-05 | 2.68E-05 | 5.94E-05 |
| SN12C | 6.44E-06 | 3.94E-05 | >1.00E-04 |
| TK-10 | 2.13E-05 | 8.22E-05 | >1.00E-04 |

TABLE 16-1-continued

Test Results for Compound 16-2b

| Panel/Cell Line | Log10 Concentration | | |
|---|---|---|---|
| | GI50 | TGI | LC50 |
| UO-31 | 6.40E-06 | 2.06E-05 | 5.11E-05 |
| Prostate Cancer | | | |
| PC-3 | 4.46E-06 | 1.66E-05 | 4.275-05 |
| DU-145 | 8.79E-06 | 2.18E-05 | 4.91E-05 |
| Breast Cancer | | | |
| MCF7 | 1.47E-06 | 3.12E-06 | 6.61E-06 |
| NCI/ADR-RES | 1.39E-05 | 3.15E-05 | 7.14E-05 |
| MDA-MB-231/ATCC | 5.00E-06 | 2.20E-05 | 6.16E-05 |
| HS 578T | 1.58E-05 | 4.01E-05 | >1.00E-04 |
| MDA-MB-435 | 1.49E-05 | 2.98E-05 | 5.98E-05 |
| MDA-N | 5.88E-06 | 2.17E-05 | 5.86E-05 |
| T-47D | 5.14E-06 | 1.89E-05 | 4.88E-05 |

TABLE 16-2

Test Results for Compound 16-2

| Panel/Cell Line | Log10 Concentration | | |
|---|---|---|---|
| | GI50 | TGI | LC50 |
| Leukemia | | | |
| CCRF-CEM | 5.90E-05 | >1.00E-04 | >1.00E-04 |
| RPMI-8226 | 3.28E-05 | >1.00E-04 | >1.00E-04 |
| SR | >1.00E-04 | >1.00E-04 | >1.00E-04 |
| Non-Small Cell Lung Cancer | | | |
| A549/ATCC | 2.23E-05 | 5.84E-05 | >1.00E-04 |
| EKVX | 1.43E-05 | 2.73E-05 | 5.23E-05 |
| HOP-62 | 2.85E-05 | >1.00E-04 | >1.00E-04 |
| HOP-92 | 1.92E-05 | 4.00E-05 | 8.37E-05 |
| NCI-H226 | 3.32E-05 | >1.00E-04 | >1.00E-04 |
| NCI-H23 | 1.68E-05 | 3.34E-05 | 6.62E-05 |
| NCI-H322M | 2.53E-05 | 8.90E-05 | >1.00E-04 |
| NCI-H460 | 1.54E-05 | 3.14E-05 | 6.41E-05 |
| Colon Cancer | | | |
| COLO 205 | 2.10E-05 | 3.65E-05 | 6.34E-05 |
| HCC-2998 | 1.64E-05 | 3.08E-05 | 5.80E-05 |
| HCT-116 | 1.33E-05 | 2.68E-05 | 5.42E-05 |
| HCT-15 | 1.18E-05 | 2.74E-05 | 6.35E-05 |
| HT29 | 1.04E-05 | 3.57E-05 | >1.00E-04 |
| KM12 | 1.86E-05 | 5.93E-05 | >1.00E-04 |
| SW-620 | 1.72E-05 | >1.00E-04 | >1.00E-04 |
| CNS Cancer | | | |
| SF-268 | 1.57E-05 | 3.48E-05 | 7.72E-05 |
| SF-295 | 2.47E-05 | 6.37E-05 | >1.00E-04 |
| SNB-19 | 1.71E-05 | 5.15E-05 | >1.00E-04 |
| SNB-75 | 2.79E-05 | 9.91E-05 | >1.00E-04 |
| U251 | 2.01E-05 | 4.50E-05 | >1.00E-04 |
| Melanoma | | | |
| LOX IMVI | 7.16E-06 | 2.13E-05 | 5.12E-05 |
| MALME-3M | 2.20E-06 | 6.79E-06 | 2.53E-05 |
| M14 | 1.15E-05 | 2.43E-05 | 5.11E-05 |
| SK-MEL-2 | 1.54E-05 | 3.45E-05 | 7.69E-05 |
| SK-MEL-28 | 2.54E-05 | 8.11E-05 | >1.00E-04 |
| SK-MEL-5 | 1.08E-05 | 2.35E-05 | 5.09E-05 |
| UACC-257 | 1.27E-05 | 2.58E-05 | 5.23E-05 |
| UACC-62 | 2.88E-06 | 1.62E-05 | 5.63E-05 |
| Ovarian Cancer | | | |
| IGROV1 | 1.40E-05 | 3.05E-05 | 6.63E-05 |
| OVCAR-3 | 3.53E-06 | 1.32E-05 | 4.23E-05 |
| OVCAR-4 | 1.67E-05 | 3.56E-05 | 7.61E-05 |

TABLE 16-2-continued

Test Results for Compound 16-2

| Panel/Cell Line | Log10 Concentration | | |
|---|---|---|---|
| | GI50 | TGI | LC50 |
| OVCAR-5 | 1.68E-05 | 3.27E-05 | 6.40E-05 |
| OVCAR-8 | 1.32E-05 | 3.15E-05 | 7.53E-05 |
| SK-OV-3 | 5.18E-05 | >1.00E-04 | >1.00E-04 |
| Renal Cancer | | | |
| 786-0 | 1.57E-05 | 4.70E-05 | >1.00-04 |
| A498 | 2.31E-05 | 7.47E-05 | >1.00E-04 |
| ACHN | 1.23E-05 | 2.72E-05 | 5.99E-05 |
| CAKI-1 | 2.03E-05 | 7.10E-05 | >1.00E-04 |
| RXF 393 | 7.51E-06 | 2.56E-05 | 7.42E-05 |
| SN12C | 1.45E-05 | 2.98E-05 | 6.12E-05 |
| TK-10 | 1.51E-05 | 3.12E-05 | 6.46E-05 |
| UO-31 | 1.37E-05 | 2.89E-05 | 6.12E-05 |
| Prostate Cancer | | | |
| PC-3 | 1.66E-05 | 4.45E-05 | >1.00E-04 |
| DU-145 | 1.50E-05 | 3.02E-05 | 6.07E-05 |
| Breast Cancer | | | |
| MCF7 | 5.81E-06 | 2.23E-05 | 6.34E-05 |
| NCI/ADR-RES | 2.34E-05 | 6.76E-05 | >1.00E-04 |
| MDA-MB-231/ATCC | 2.38E-05 | 5.28E-05 | >1.00E-04 |
| HS 578T | 7.58E-06 | 3.16E-05 | >1.00E-04 |
| MDA-MB-435 | 1.28E-05 | 2.91E-05 | 6.59E-05 |
| MDA-N | 1.25E-05 | 2.61E-05 | 5.45E-05 |
| BT-549 | 1.56E-05 | 3.22E-05 | 6.64E-05 |
| T-47D | 1.33E-05 | 3.96E-05 | >1.00E-04 |

TABLE 16-3

Test Results for Compound 16-1

| Panel/Cell Line | Log10 Concentration | | |
|---|---|---|---|
| | GI50 | TGI | LC50 |
| Leukemia | | | |
| CCRF-CEM | >1.00E-04 | >1.00E-04 | >1.00E-04 |
| K-562 | >1.00E-04 | >1.00E-04 | >1.00E-04 |
| MOLT-4 | >1.00E-04 | >1.00E-04 | >1.00E-04 |
| RPMI-8226 | >1.00E-04 | >1.00E-04 | >1.00E-04 |
| SR | >1.00E-04 | >1.00E-04 | >1.00E-04 |
| Non Small Cell Lung Cancer | | | |
| A549/ATCC | >1.00E-04 | >1.00E-04 | >1.00E-04 |
| EKVX | >1.00E-04 | >1.00E-04 | >1.00E-04 |
| HOP-62 | >1.00E-04 | >1.00E-04 | >1.00E-04 |
| HOP-92 | >1.00E-04 | >1.00E-04 | >1.00E-04 |
| NCI-H226 | >1.00E-04 | >1.00E-04 | >1.00E-04 |
| NCI-H23 | >1.00E-04 | >1.00E-04 | >1.00E-04 |
| NCI-H322M | >1.00E-04 | >1.00E-04 | >1.00E-04 |
| NCI-H460 | >1.00E-04 | >1.00E-04 | >1.00E-04 |
| NCI-H522 | >1.00E-04 | >1.00E-04 | >1.00E-04 |
| Colon Cancer | | | |
| COLO 205 | >1.00E-04 | >1.00E-04 | >1.00E-04 |
| HCC-2998 | >1.00E-04 | >1.00E-04 | >1.00E-04 |
| HCT-116 | >1.00E-04 | >1.00E-04 | >1.00E-04 |
| HCT-15 | >1.00E-04 | >1.00E-04 | >1.00E-04 |
| KM12 | >1.00E-04 | >1.00E-04 | >1.00E-04 |
| SW-620 | >1.00E-04 | >1.00E-04 | >1.00E-04 |
| CNS Cancer | | | |
| SF-268 | >1.00E-04 | >1.00E-04 | >1.00E-04 |
| SF-295 | >1.00E-04 | >1.00E-04 | >1.00E-04 |
| SF-539 | >1.00E-04 | >1.00E-04 | >1.00E-04 |
| SNB-19 | >1.00E-04 | >1.00E-04 | >1.00E-04 |
| SNB-75 | 5.02E-07 | >1.00E-04 | >1.00E-04 |

TABLE 16-3-continued

Test Results for Compound 16-1

| | Log10 Concentration | | |
|---|---|---|---|
| Panel/Cell Line | GI50 | TGI | LC50 |
| U251 | >1.00E-04 | >1.00E-04 | >1.00E-04 |
| Melanoma | | | |
| MALME-3M | >1.00E-04 | >1.00E-04 | >1.00E-04 |
| M14 | >1.00E-04 | >1.00E-04 | >1.00E-04 |
| SK-MEL-28 | >1.00E-04 | >1.00E-04 | >1.00E-04 |
| UACC-257 | >1.00E-04 | >1.00E-04 | >1.00E-04 |
| UACC-62 | >1.00E-04 | >1.00E-04 | >1.00E-04 |
| Ovarian Cancer | | | |
| OVCAR-3 | >1.00E-04 | >1.00E-04 | >1.00E-04 |
| OVCAR-4 | >1.00E-04 | >1.00E-04 | >1.00E-04 |
| OVCAR-5 | >1.00E-04 | >1.00E-04 | >1.00E-04 |
| OVCAR-8 | >1.00E-04 | >1.00E-04 | >1.00E-04 |
| SK-OV-3 | >1.00E-04 | >1.00E-04 | >1.00E-04 |
| Renal Cancer | | | |
| 786-0 | >1.00E-04 | >1.00E-04 | >1.00E-04 |
| A498 | >1.00E-04 | >1.00E-04 | >1.00E-04 |
| ACHN | >1.00E-04 | >1.00E-04 | >1.00E-04 |
| CAKI-1 | >1.00E-04 | >1.00E-04 | >1.00E-04 |
| RXF 393 | >1.00E-04 | >1.00E-04 | >1.00E-04 |
| SN12C | >1.00E-04 | >1.00E-04 | >1.00E-04 |
| UO-31 | >1.00E-04 | >1.00E-04 | >1.00E-04 |
| Prostate Cancer | | | |
| DU-145 | >1.00E-04 | >1.00E-04 | >1.00E-04 |
| Breast Cancer | | | |
| NCI/ADR-RES | >1.00E-04 | >1.00E-04 | >1.00E-04 |
| MDA-MB-231/ATCC | 5.62E-06 | >1.00E-04 | >1.00E-04 |
| MDA-MB-435 | >1.00E-04 | >1.00E-04 | >1.00E-04 |
| MDA-N | >1.00E-04 | >1.00E-04 | >1.00E-04 |
| BT-549 | >1.00E-04 | >1.00E-04 | >1.00E-04 |
| T-47D | >1.00E-04 | >1.00E-04 | >1.00E-04 |

Example 17

Inhibition of Adenosine Deaminase and Guanine Deaminase (Guanase) Activities of the Following Compounds:

Compound 17-1: 4,8-Diamino-6H-6-imino-1-β-D-ribofuranosylimidazo[4,5-e][1,3]diazepine

[Formula IB, wherein J, L, X, Z=N; K, U, Y, W=C; $R_1=R_5=NH_2$; $R_3=NH$; $R_7=H$; $R_2=R_4=R_8$=None; and $R_6$=1-β-D-ribofuranosyl]

Compound 17-2: 4,8-Diamino-6H-6-imino-1-β-D-ribofuranosylimidazo[4,5-e][1,3]diazepine

[Formula IB, Wherein J, L, X, Z=N; K, U, Y, W=C; $R_1=R_5=NH_2$; $R_3=NH$; $R_7=H$; $R_2=R_4=R_8$=None; and $R_6$=hydroxyethoxymethyl]

Figure 13:
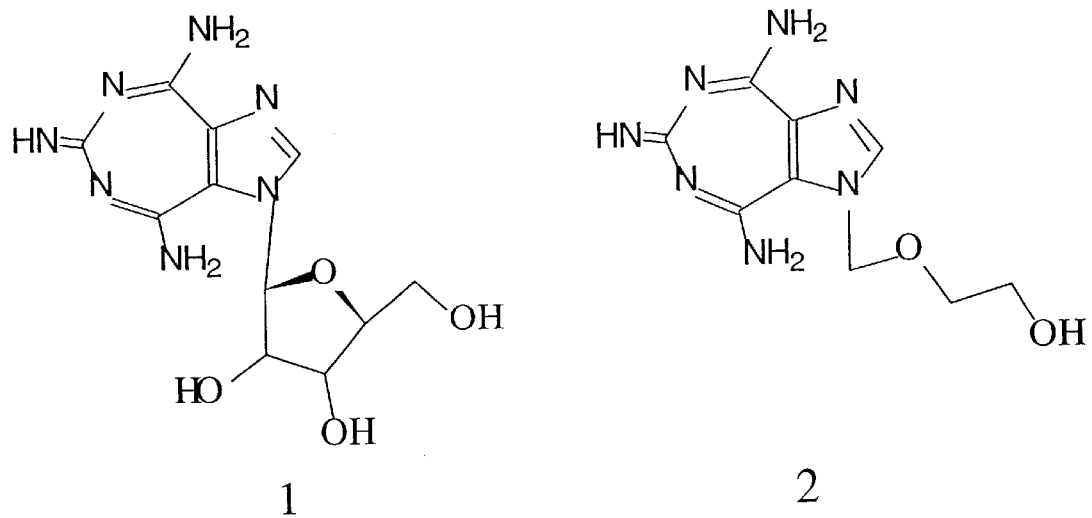

Adenosine Deaminase Assay:

Inhibition of adenosine deaminase (ADA) by Compound 17-1 and Compound 17-2 (see FIG. 13 for chemical structures; note that structure 1 FIG. 13 is the same as that in figure except that it is written in an anti-conformation in the former) was investigated in vitro against adenosine deaminase from calf intestinal mucosa in a 50 mM phosphate buffer (pH=7.4) at 25° C., by spectro-photometrically monitoring the rate of hydrolysis of substrate adenosine at 265 nm. Stock solutions of the substrate, enzyme, and inhibitors were prepared using a 50 mM phosphate buffer (pH 7.4). The enzyme kinetics was followed by measuring the change in optical density (decrease in absorbance) per minute of the substrate adenosine. By keeping the concentration of the inhibitor constant, and by varying the substrate concentration, a set of kinetic data was obtained. Additional sets of data were generated using different concentrations of the inhibitor. The substrate concentration in each assay ranged 20–40 $\mu$M; a total of six different concentrations were employed. The inhibitor concentration used in each assay was 46 or 92 $\mu$M. The amount of enzyme used in each assay was 0.0216 unit. The $K_i$ for inhibition assays was computed from Lineweaver-Burk plots. The Lineweaver-Burk plot (1/V vs 1/[S]), as well as the linear regression analysis of kinetic data, were performed using the program Quattro Pro (version 6.01) for Windows.™.

As computed from the Lineweaver-Burk plots:

1. Compound 17-1 was found to be an inhibitor of adenosine deaminase with a $K_i$=3.85–4.44×10$^{-4}$ M, and
2. Compound 17-2 was a competitive inhibitor of adenosine deaminase with a $K_i$=1.18–1.84×10$^{-4}$ M.

In order to study the enzyme-inhibitor binding mechanism as well to assess the ADA inhibition, the following experiments were conducted using Compound 17-2. Two experiments were conducted using the procedure of Agarwal et al. (R. P. Agarwal et al., In Chemistry and Biology of Nucleosides and Nucleotides; Harmon, R. E.; Robins, R. K.; Townsend, L. B., Eds; Academic Press: New York, pp159–197 (1978)).

(a) pre-incubation of the enzyme with the inhibitor; here the enzyme (ADA 10 $\mu$L) and inhibitor were preincubated for 10 min in a calculated amount of phosphate buffer (50 mM, pH 7.5 ) at 25° C. and the reaction was initiated by the addition of substrate, adenosine, and (b) without preincubation; here the reaction was started by addition of ADA (10 $\mu$L) to a mixture of adenosine and inhibitor in the phosphate buffer at 25° C. When the inhibitor Compound 17-2 was examined with and without preincubation with ADA, identical reaction velocities were observed over a 3 min incubation period. This indicated that Compound 17-2 is a reversible inhibitor with a rapid establishment of equilibrium between E, ES, and EI. Therefore, it was possible to employ the initial velocities to determine both the inhibition mechanism and the $K_i$ value, using the Lineweaver-Burk analyses.

Guanine Deaminase Assay

Compound 17-1 and Compound 17-2 were also assayed in vitro for inhibition of guanine deaminase (guanase) from rabbit liver in a 50 mM Tris-HCl buffer (pH=7.4) at 27° C., by spectro-photometrically monitoring the rate of hydrolysis of substrate guanine at 243 nm, using the procedure of Lewis and Glantz (Lewis, A. S.; Glantz, M. D., J. Biol. Chem., 249, 3862–3866 (1974)).

Stock solutions of the substrate, enzyme, and inhibitors were prepared using a 50 mM Tris-HCl buffer (pH 7.4). The enzyme kinetics was followed by measuring the change in optical density (decrease in absorbance) per minute of the substrate guanine. By keeping the concentration of the inhibitor constant, and by varying the substrate concentration, a set of kinetic data was obtained. Additional sets of data were generated using different concentrations of the inhibitor. The substrate concentration in each assay ranged 6–20 $\mu$M; a total of six different concentrations were employed. The inhibitor concentration used in each assay was 30 or 40 $\mu$M. The amount of enzyme used in each assay was 0.0076 unit. The $K_i$ for inhibition assays was computed from Lineweaver-Burk plots. The Lineweaver-Burk plot (1/V vs 1/[S]), as well as the linear regression analysis of kinetic data, were performed using the program Quattro Pro (version 6.01) for Windows.™.

As computed from the Lineweaver-Burk plots, Compound 17-2 was found to be a competitive inhibitor of guanine deaminase (guanase) with a $K_i$=2.7–3.2×10$^{-5}$ M but Compound 17-1 was found to be inactive against guanase.

CONCLUSION

While the ribonucleoside Compound 17-1 is a competitive inhibitor of adenosine deaminase, the acyclic nucleoside Compound 17-2 is a competitive inhibitor of both adenosine deaminase and guanase. They are particularly effective in respectively inhibiting adenosine deaminase and guanase in humans. The heterocyclic ring of Compound 17-1 and 17-2 can be regarded as a ring-expanded analogue of the natural purine. It should be noted that Compound 17-2 is able to inhibit two different enzymes of purine metabolism that have different specificities for substrates. The result may be rationalized by the fact that several different tautomeric structures can be drawn for the triamino heterocycle so as to resemble both adenine and guanine. Since guanine deaminase acts only on the heterocyclic base, but not the nucleoside, it is not surprising that Compound 17-1 is inactive against guanase.

Example 18

Figure 15:
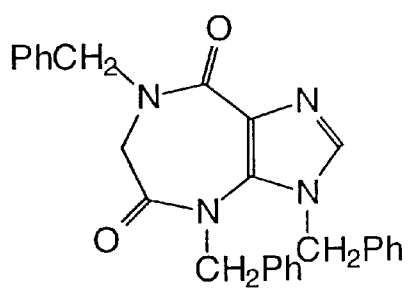
Figure 15:
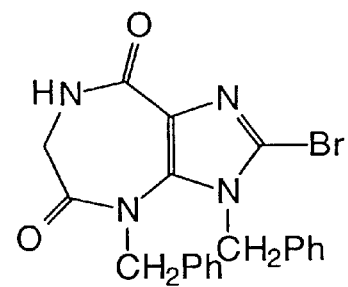

Synthesis and Anti-Epstein-Barr Virus (EBV) Effects of:

Compound 18-1: 3,4,7-Tribenzyl-4,5,7,8-tetrahydro-6H-imidazo[4,5-e][1,4]diazepine-5,8-dione (see FIG. 15 for Structure)

[Formula IV, Where U, Y, Z, K=C; X, W, J, L=N; $R_1$, $R_5$=O; $R_2$, $R_6$, $R_7$=CH$_2$Ph; $R_3$, $R_4$, $R_8$=H; $R_9$=None], and Compound 18-2: 3,4-Dibenzyl-2-bromo-4,5,7,8-tetrahydro-6H-imidazo[4,5-e][1,4]diazepine-5,8-dione (see FIG. 15 for Structure)

[Formula IV, Where U, Y, Z, K=C; X, W, J, L=N; $R_1$, $R_5$=O; $R_2$, $R_3$, $R_4$=H; $R_6$, $R_7$=CH$_2$Ph; $R_8$=Br; $R_9$=None]

This example includes the two title 5:7-fused, non-planar, non-aromatic ring-expanded heterocycles, which possess potent anti-Epstein-Barr Virus (anti-EBV) activity in vitro. (see FIG. 15 for structures).

The physicochemical data of the two Compounds, 18-1 and 18-2, are as follows (see Bhan, A.; Hosmane, R. S., *J. Heterocyclic Chem.*, 30:1453–1462, 1993 for experimental details):

Compound 18-1: White crystals, mp 170–172° C.; $^1$H NMR (DMSO-d$_6$): Δ7.79 (s, 1H, imidazole CH), 7.05 (m, 15H, Ph-H), 5.35 (two d, 2H, benzyl CH$_2$), 5.20 (d, J=15.5 Hz, 1H, CH of benzyl CH$_2$), 4.62 (two d, 2H, benzyl CH$_2$), 4.39 (d, J=15.5 Hz, 1H, CH of benzyl CH$_2$), 4.10 (d, J=14.5 Hz, 1H, CH of ring CH$_2$), 3.70 (d, J=14.5 Hz, 1H, CH of ring CH$_2$); ms (CI, isobutane): m/z 437 (M$^+$+1, 100%), 376, 347, 303, 257, 226, 195, 154, 107.

Anal. Calcd. for C$_{27}$H$_{24}$N$_4$O$_2$: C, 74.29; H, 5.53; N, 12.83. Found: C, 74.02; H, 5.59; N, 12.67.

Compound 18-2: Pale yellow crystals, mp 239–241° C.; $^1$H NMR (DMSO-d$_6$): Δ8.24 (br s, 1H, NH), 7.11 (m, 10H, Ph-H), 5.30 (s, 2H, benzyl CH$_2$), 5.16 (d, J=15.5 Hz, 1H, CH of benzyl CH$_2$), 4.35 (d, J=15.5 Hz, 1H, CH of benzyl CH$_2$), 4.11 (m, 1H, CH of ring CH$_2$), 3.50 (m, 1H, CH of ring CH$_2$); Ms (CI, isobutane): m/z 427, 425 (M$^+$+1), 347, 298, 257, 239, 213.

Anal. Calcd. for C$_{20}$H$_{17}$N$_4$O$_2$Br: C, 56.48; H, 4.02; N, 13.17; Br, 18.79. Found: C, 56.48; H, 4.05; N, 13.15; Br, 18.84.

Antiviral Screening for Epstein-Barr Virus (EBV) Activity

Compounds 18-1 and 18-2 (FIG. 15) were screened for anti-EBV activity in tissue culture systems, and were both found to possess good anti-EBV activity. The following assays were performed to assess their antiviral activity as well as toxicity.

Viral Capsid Antigen (VCA) or EBV Immunofluorescence Assay: A concentration of 1×10$^6$ Daudi cells were infected with 0.1–0.2 mol of P3HR-1 strain of EBV in RPMI-1640 medium for 45 min at 37° C. in a CO$_2$ incubator. After virus adsorption, the cells were washed and pelleted, and the supernatant was discarded. The drugs to be tested were serially diluted in RPMI-1640 and added to the appropriate tubes. The cultures were incubated for 2 days in complete medium to allow viral gene expression. Following the 48 h incubation period, a number of cells of each sample were counted and washed in phosphate-buffered saline (PBS), and slides were prepared. The slides were dried overnight. The dried cells were fixed with acetone. A monoclonal antibody to viral capsid antigen (VCA) was then added to the cells, incubated for 30 min at 37° C., and washed in PBS. This was followed by a fluorescein-conjugated goat anti-mouse IgG antibody. The cells were counterstained with. Evans Blue. A total of 500 negative and fluorescence positive cells were counted. The total number of VCA positive cells in the cultures was calculated and EC$_{50}$ values determined using Microsoft Excel Software.

The following assays were performed to determine the cytotoxicity of compounds 18-1 and 18-2:

(A) Cell Proliferation Assay: Twenty-four hours prior to assay, cells (HFF or Daudi) were seeded in six-well plates at a concentration of 2.5×10$^4$ cells per well in MEM containing 10% FBS. On the day of the assay, drugs were diluted serially in MEM containing 10% FBS at increments of 1:5 covering a range from 100 to 0.03 mg/mL. For drugs that had to be solubilized in DMSO, control wells receive MEM containing 10% DMSO. The media from the wells was then aspirated, and 2 mL of each drug concentration was added to each well. The cells were incubated in a CO$_2$ incubator at 37° C. for 72 h. At the end of this time, the media-drug solution was removed, and the cells were washed. Trypsin-EDTA (0.25%, 1 mL) was added to each well and incubated until the cells started to come off the plate. The cell-media mixture was then pipeted up and down vigorously to break up the cell suspension and 0.2 mL of the mixture added to 9.8 mL of Isoton III and the cells were counted using a Coulter Counter. Each sample was counted three times with two replicate wells per sample. The IC$_{50}$ values were calculated using a computer program.

(B) Neutral Red Uptake Assay: Twenty-four hours prior to assay, HFF cells were plated into 96-well plates at a concentration of 2.5×10$^4$ cells/well. After 24 h, the media was aspirated, and 125 mL of media containing drug was added to the first row of wells and then diluted serially 1:5 using the automated Cetus Liquid Handling System. The plates were then incubated in a Co$_2$ incubator at 37° C. for 7 days. At this time the media/drug was removed, cells were washed, 200 μL/well of 0.01% neutral red in PBS was added, and the mixture was incubated for 1 h. The dye was removed, and the cells were washed using a Nunc Plate Washer. After the wash was removed, 200 mL/well of 50% ethanol/1% aqueous acetic acid was added. The plates were placed on a rotating shaker for 15 min, and the optical densities were then read at 540 nm using a plate reader.

Data Analysis: Dose-response relationships were constructed by linearly regressing the percent inhibition of parameters derived in the preceding sections against log drug concentrations. Fifty-percent inhibitory ($IC_{50}$) concentrations were calculated from the regression lines. Samples containing positive controls as shown in the table were used in all assays.

The observed anti-EBV activity and cytotoxicity data of Compounds 18-1 and 18-2, along with those of aciclovir which was used as a reference standard, are summarized in Table 18. The compounds are particularly useful in treating human EBV.

TABLE 18

Anti-EBV activity and cytotoxicity of compounds 18-1 and 18-2 in tissue cultures

| Antiviral Activity | Cytotoxicity ($IC_{50}$)[b] ($\mu$g/mL) | | | | | |
|---|---|---|---|---|---|---|
| ($EC_{50}$)[a] ($\mu$g/mL) (Daudi cells) | Neutral Red Uptake[e] | | Daudi Cells | | HFF Cells[f] | |
| Compound | $EC_{50}$[a] | $IC_{50}$[b] | $SI$[c] | $IC_{50}$[b] | $SI$[c] | $IC_{50}$[b] | $SI$[c] |
| 18-1 | 4.1 | >100 | >24 | >50 | >12 | >100 | >24 |
| 18-2 | 8.3 | >100 | >12 | >50 | >6 | >100 | >12 |
| Aciclovir[d] | 0.8 | >100 | >125 | >50 | >62 | >100 | >125 |

[a]$EC_{50}$ is defined as 50% effective virus-inhibitory concentration.
[b]$IC_{50}$ is defined as 50% cell-inhibitory concentration
[c]SI (Selectivity Index) is obtained by dividing $IC_{50}$ by $EC_{50}$. An SI value 10 or greater is indicative of positive antiviral activity.
[d]Aciclovir was used as a reference standard in all assays.
[e]The assay was conducted using stationary HFF cells.
[f]The assay was performed using rapidly growing HFF cells.

Example 19

Figure 16:
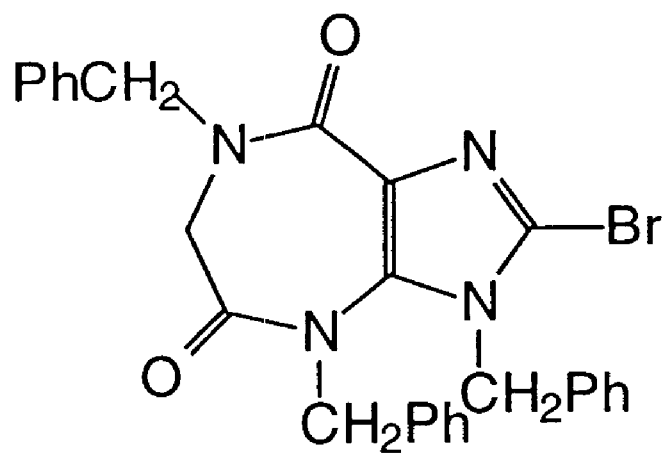

Synthesis and Anti-Cytomegalovirus (CMV) Effects of:

Compound 19: 3,4,7-Tribenzyl-2-bromo-4,5,7,8-tetrahydro-6H-imidazo [4,5-e][1,4]diazepine-5,8-dione (see FIG. 16 for Structure)

[Formula IV, Where U, Y, Z, K=C; X, W, J, L=N; $R_1$, $R_5$=O; $R_2$, $R_6$, $R_7$=$CH_2Ph$; $R_3$, $R_4$; $R_8$=Br; $R_9$= None]

This example includes the title 5:7-fused, non-planar, non-aromatic ring-expanded heterocycle, which has anti-cytomegalovirus (anti-CMV) activity in vitro. (see FIG. 16 for structure)

The physicochemical data of Compound 19 are given below (see Bhan, A.; Hosmane, R. S., *J. Heterocyclic Chem.*, 30:1453–1462, 1993 for experimental details):

Compound 19: Off-white crystals, mp 174–176° C.; $^1$H NMR (DMSO-$d_6$): $\Delta$7.0 (m, 15H, Ph-H), 5.30 (s, 2H, benzyl $CH_2$), 5.12 (d, J=5.0 Hz, 1H, CH of $CH_2$), 4.62 (two d, 2H, $CH_2$), 4.28 (m, 2H, $CH_2$), 3.74 (d, J=5.0 Hz, 1H, CH of $CH_2$); ms (CI, isobutane): m/z 517, 515 ($M^+$+1), 437, 363, 347, 273, 241, 170.

Anal. Calcd. for $C_{27}H_{23}N_4O_2Br$: C, 62.92; H, 4.49; N, 10.87; Br, 15.50. Found: C, 62.82; H, 4.48; N, 10.77; Br, 15.44.

Assessment of Anti-Cytomegalovirus (Anti-CMV) Activity of Compound 19 (FIG. 16)

The following in vitro assays were performed to assess the anti-CMV activity as well as cytotoxicity of Compound 19.

Cytopathic Effect (CPE) Inhibition Assay: Low passage HFF cells were seeded into 96-well tissue culture plates 24 h prior to use at a cell concentration of 2.5×$10^5$ cells/mL in 0.1 mL of MEM supplemented with 10% FBS. The cells were incubated for 24 h at 37° C. in a $CO_2$ incubator. After incubation, the medium was removed, and 100 $\mu$L of MEM containing 2% FBS was added to all but the first row. In the first row, 125 $\mu$L of experimental drug was added in triplicate wells. Medium alone was added to both cell and virus control wells. The drug in the first row of wells was then diluted serially 1:5 throughout the remaining wells by transferring 25 $\mu$L using the Cetus Liquid Handling Machine. After a 1 h incubation, 100 $\mu$L of the appropriate virus concentration was added to each well, excluding cell control wells which received 100 $\mu$L of MEM. The virus concentration added was 2500 pfu per well. The plates were then incubated at 37° C. in a $CO_2$ incubator for 14 days. An additional 50 $\mu$L of MEM was added on day 7. After the incubation period, media was aspirated, and the cells were stained with a 5% crystal violet/ethanol/formaldehyde solution for 4 h. The stain was then removed, and the plates were rinsed with tap water until all excess stain was removed. The plates were allowed to dry for 24 h and then read on a Bio-Tek Instruments Microplate reader at 630 nm.

For assessment of cytotoxicity, two assays were employed: (a) Neutral Red Uptake Assay, and (b) Cell Proliferation Assay. Both assays were conducted using HFF cells. The procedures employed for these assays are essentially the same as the ones described for compounds 18-1 and 18-2 under Example 18 above.

The observed anti-CMV, and in particular, anti-human CMV, activity and cytotoxicity data of Compound 19, along with those of ganciclovir which was used as the reference standard, are summarized in Table 19 below.

TABLE 19

Anti-HCMV activity and cytotoxicity of compound 19 in tissue cultures

| Antiviral Activity | Cytotoxicity ($IC_{50}$)[b] ($\mu$g/mL) | | | |
|---|---|---|---|---|
| ($EC_{50}$)[a] ($\mu$g/mL) (HFF Cells) | Neutral Red Uptake[e] | | HFF Cells[f] | |
| Compound | $EC_{50}$[a] | $IC_{50}$[b] | $SI$[c] | $IC_{50}$[b] | $SI$[c] |
| 19 | 8.1 | 88.1 | 10.9 | 56.5 | 6.98 |
| Ganciclovir[d] | 0.05 | >100 | >2000 | 40.0 | 800 |

[a]$EC_{50}$ is defined as 50% effective virus-inhibitory concentration.
[b]$IC_{50}$ is defined as 50% cell-inhibitory concentration.
[c]SI (Selectivity Index) is obtained by dividing $IC_{50}$ by $EC_{50}$. An SI value 10 or greater is indicative of positive antiviral activity.
[d]Ganciclovir was used as a reference standard in all assays.
[e]The assay was conducted using stationary HFF cells.
[f]The assay was performed using rapidly growing HFF cells.

What is claimed is:

1. A method of treating a viral infection in a patient or vertebrate animal in need thereof comprising administering to said patient or vertebrate animal in an amount sufficient to effect said treatment, at least one of potentially planar, aromatic, ring-expanded heterocyclic bases, nucleosides and nucleotide compounds having the structure

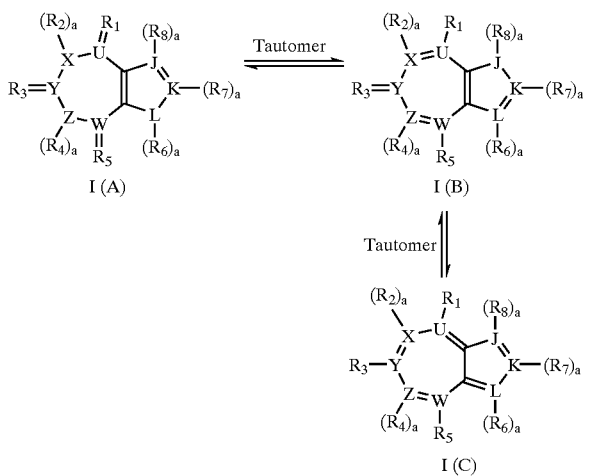

wherein:

$R_1$, $R_3$ and $R_5$ are each independently selected from the group consisting of:

NH, $NH_2$, O, OH, S, and SH;

NH-alkyl, N-alkyl, O-alkyl and S-alkyl wherein the alkyl group is $C_1$–$C_{20}$;

NH-aryl, O-aryl and S-aryl wherein the aryl group is a substituted or unsubstituted phenyl or a heterocyclic group;

$R_2$, $R_4$, $R_7$, and $R_8$ are independently selected from the group consisting of hydrogen, $C_1$–$C_{20}$ alkyl, substituted phenyl, unsubstituted phenyl, unsubstituted heterocycle, substituted heterocycle, aralkyl wherein the alkyl containing 1 to 6 carbon atoms and the aryl is substituted or unsubstituted;

$R_6$ is selected from the group consisting of
hydrogen,
$C_1$–$C_{20}$ alkyl,
substituted phenyl,
unsubstituted phenyl,
unsubstituted heterocycle,
substituted heterocycle, and
aralkyl wherein the alkyl containing 1 to 6 carbon atoms and the aryl is substituted or unsubstituted;
a glycosyl group selected from the group consisting of ribosyl, 2'-deoxyribosyl, 2',3'-dideoxyribosyl, 2',3'-dideoxy-2'-fluororibosyl, 2',3'-dideoxy-3'-fluororibosyl, 2',3'-dideoxy-2',3'-fluororibosyl, 2',3'-dideoxy-3'-azidoribosyl and mono-, di-, and triphosphate derivatives thereof;
—$(CH_2)_{m+n+1}$—R';
—$(CH_2)_m$—O—$(CH_2)_n$—O—R';
—$(CH_2)_{m+1}$—O—R';
—$(CH_2)_m$—O—$(CH_2)_n$—R';
wherein R' is selected from the group consisting of: hydrogen, $H_2PO_3$, $H_3P_2O_6$, $H_4P_3O_9$, and alkali metal or alkaline earth metal salts thereof;
m is zero to 20, n is zero to 20, and a is zero or one;
U, X, Y, Z, W, J, K, and L are selected from the group consisting of C and N;
and all chiral forms and stereoisomers of said compounds.

2. The method of claim 1 wherein said infection is a virus infection.

3. The method of claim 1 wherein said viral infection is caused by a virus selected from the group consisting of human immunodeficiency virus, Human B lymphotropic virus, Herpes simplex virus, Varicella-zoster virus, Epstein-Barr virus, necrotic rhinitis, Malignant catarrh, Allerton virus, Equine herpesviruses, Neurolymphomatosis, Influenza viruses, Parainfluenza viruses, Adenoviruses, Rheovirus, Respiratory syncytial virus, Rhinoviruses, Coxsackie virus, Echo viruses, Epidemic gastroenteritis virus, Rubeola virus, Hepatitis viruses, cytomegalovirus virus and Papovavirus.

4. The method of claim 1 wherein said viral infection is caused by Hepatitis viruses.

5. The method of claim 1 wherein said viral infection is caused by Hepatitis B virus.

6. The method of claim 1 wherein said viral infection is caused by Epstein-Barr virus.

7. The method of claim 1 wherein said viral infection is caused by cytomegalovirus virus.

8. The method of claim 1 wherein said compound is administered subcutaneously, intravenously, intramuscularly, intraperitoneally, orally, topically, or by a combination thereof.

9. The method of claim 1 wherein said at least one compound is administered in combination with at least one known therapeutic agent.

10. The method of claim 1 wherein said compound is in a therapeutic form of a pharmaceutically acceptable salt, phosphonate, ester or salt of said ester, which provides said compound or its therapeutically effective metabolite during said treatment.

11. A method of inhibiting the growth of cancer in a patient or vertebrate animal comprising administering to said patient or vertebrate animal in an amount sufficient to effect said inhibition, at least one of potentially planar, aromatic, ring-expanded heterocyclic bases, nucleosides and nucleotide compounds having the structure

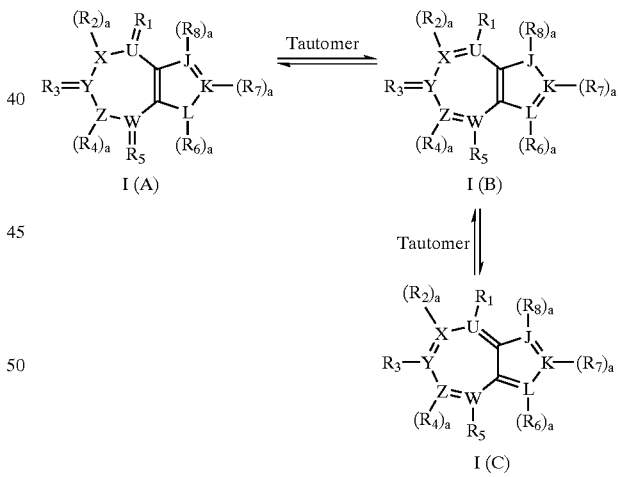

wherein:

$R_1$, $R_3$ and $R_5$ are each independently selected from the group consisting of:

NH, $NH_2$, O, OH, S, and SH;

NH-alkyl, N-alkyl, O-alkyl and S-alkyl wherein the alkyl group is $C_1$–$C_{20}$;

NH-aryl, O-aryl and S-aryl wherein the aryl group is a substituted or unsubstituted phenyl or a heterocyclic group;

$R_2$, $R_4$, $R_7$, and $R_8$ are independently selected from the group consisting of hydrogen, $C_1$–$C_{20}$ alkyl, substituted phenyl, unsubstituted phenyl, unsubstituted heterocycle, substituted heterocycle, aralkyl wherein the alkyl containing 1 to 6 carbon atoms and the aryl is substituted or unsubstituted;

$R_6$ is selected from the group consisting of hydrogen, $C_1$–$C_{20}$ alkyl, substituted phenyl, unsubstituted phenyl, unsubstituted heterocycle, substituted heterocycle, and aralkyl wherein the alkyl containing 1 to 6 carbon atoms and the aryl is substituted or unsubstituted;

a glycosyl group selected from the group consisting of ribosyl, 2'-deoxyribosyl, 2',3'-dideoxyribosyl, 2',3'-dideoxy-2'-fluororibosyl, 2',3'-dideoxy-3'-fluororibosyl, 2',3'-dideoxy-2',3'-fluororibosyl, 2',3'-dideoxy-3'-azidoribosyl and mono-, di-, and triphosphate derivatives thereof;

—$(CH_2)_{m+n+1}$—R'

—$(CH_2)_m$—O—$(CH_2)_n$—O—R';

—$(CH_2)_{m+1}$—O—R';

—$(CH_2)_m$—O—$(CH_2)_n$—R';

wherein R' is selected from the group consisting of: hydrogen, $H_2PO_3$, $H_3P_2O_6$, $H_4P_3O_9$, and alkali metal or alkaline earth metal salts thereof;

m is zero to 20, n is zero to 20, and a is zero or one;

U, X, Y, Z, W, J, K, and L are selected from the group consisting of C and N;

and all chiral forms and stereoisomers of said compounds.

12. The method of claim 11 wherein said cancer is selected from the group consisting of leukemia, non-small cell lung cancer, colon cancer, CNS cancer, melanoma, ovarian cancer, renal cancer, prostate cancer and breast cancer.

13. The method of claim 11 wherein said compound is administered subcutaneously, intravenously, intramuscularly, intraperitoneally, orally, topically, or by a combination thereof.

14. The method of claim 11 wherein said at least one compound is administered in combination with at least one known therapeutic agent.

15. The method of claim 11 wherein said compound is in a therapeutic form of a pharmaceutically acceptable salt, phosphonate, ester or salt of said ester, which provides said compound or its therapeutically effective metabolite during said treatment.

16. A method of inhibiting enzymatic activity of RNA polymerases in a patient or vertebrate animal comprising administering to said patient or vertebrate animal in an amount sufficient to effect said inhibition, at least one of potentially planar, aromatic, ring-expanded heterocyclic bases, nucleosides and nucleotide compounds having the structure

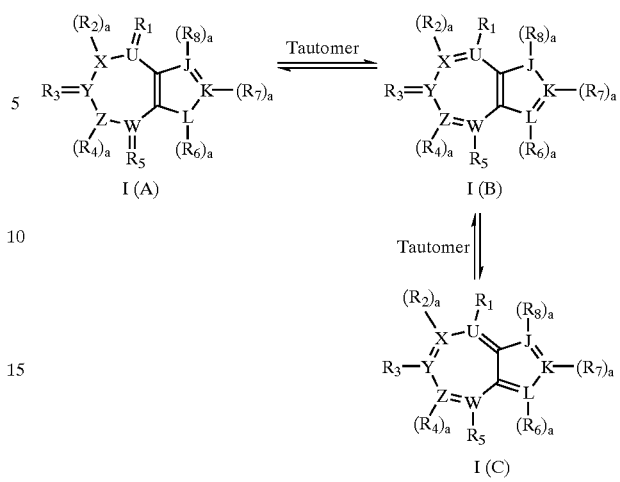

I (A)   I (B)

I (C)

wherein:

$R_1$, $R_3$ and $R_5$ are each independently selected from the group consisting of:

NH, $NH_2$, O, OH, S, and SH;

NH-alkyl, N-alkyl, O-alkyl and S-alkyl wherein the alkyl group is $C_1$–$C_{20}$;

NH-aryl, O-aryl and S-aryl wherein the aryl group is a substituted or unsubstituted phenyl or a heterocyclic group;

$R_2$, $R_4$, $R_7$, and $R_8$ are independently selected from the group consisting of hydrogen, $C_1$–$C_{20}$ alkyl, substituted phenyl, unsubstituted phenyl, unsubstituted heterocycle, substituted heterocycle, aralkyl wherein the alkyl containing 1 to 6 carbon atoms and the aryl is substituted or unsubstituted;

$R_6$ is selected from the group consisting of hydrogen, $C_1$–$C_{20}$ alkyl, substituted phenyl, unsubstituted phenyl, unsubstituted heterocycle, substituted heterocycle, and aralkyl wherein the alkyl containing 1 to 6 carbon atoms and the aryl is substituted or unsubstituted;

a glycosyl group selected from the group consisting of ribosyl, 2'-deoxyribosyl, 2',3'-dideoxyribosyl, 2',3'-dideoxy-2'-fluororibosyl, 2',3'-dideoxy-3'-fluororibosyl, 2',3'-dideoxy-2',3'-fluororibosyl, 2',3'-dideoxy-3'-azidoribosyl and mono-, di-, and triphosphate derivatives thereof;

—$(CH_2)_{m+n+1}$—R'

—$(CH_2)_m$—O—$(CH_2)_n$—O—R';

—$(CH_2)_{m+1}$—O—R';

—$(CH_2)_m$—O—$(CH_2)_n$—R';

wherein R' is selected from the group consisting of: hydrogen, $H_2PO_3$, $H_3P_2O_6$, $H_4P_3O_9$, and alkali metal or alkaline earth metal salts thereof;

m is zero to 20, n is zero to 20, and a is zero or one;

U, X, Y, Z, W, J, K, and L are selected from the group consisting of C and N;

and all chiral forms and stereoisomers of said compounds.

17. The method of claim 16 wherein said compound is administered subcutaneously, intravenously, intramuscularly, intraperitoneally, orally, topically, or by a combination thereof.

18. The method of claim 16 wherein said at least one compound is administered in combination with at least one known therapeutic agent.

19. The method of claim 16 wherein said compound is in a therapeutic form of a pharmaceutically acceptable salt, phosphonate, ester or salt of said ester, which provides said compound or its therapeutically effective metabolite during said treatment.

20. A method of inhibiting enzymatic activity of adenosine deaminase and/or guanine deaminase in a patient or vertebrate animal comprising administering to said patient or vertebrate animal in an amount sufficient to effect said inhibition, at least one of potentially planar, aromatic, ring-expanded heterocyclic bases, nucleosides and nucleotide compounds having the structure

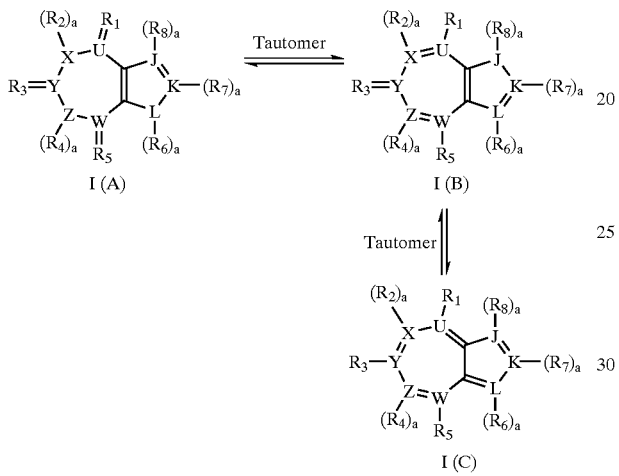

wherein:
$R_1$, $R_3$ and $R_5$ are each independently selected from the group consisting of:
NH, $NH_2$, O, OH, S, and SH;
NH-alkyl, N-alkyl, O-alkyl and S-alkyl wherein the alkyl group is $C_1$–$C_{20}$;
NH-aryl, O-aryl and S-aryl wherein the aryl group is a substituted or unsubstituted phenyl or a heterocyclic group;
$R_2$, $R_4$, $R_7$, and $R_8$ are independently selected from the group consisting of hydrogen, $C_1$–$C_{20}$ alkyl, substituted phenyl, unsubstituted phenyl, unsubstituted heterocycle, substituted heterocycle, aralkyl wherein the alkyl containing 1 to 6 carbon atoms and the aryl is substituted or unsubstituted;
$R_6$ is selected from the group consisting of
hydrogen,
$C_1$–$C_{20}$ alkyl,
substituted phenyl,
unsubstituted phenyl,
unsubstituted heterocycle,
substituted heterocycle, and
aralkyl wherein the alkyl containing 1 to 6 carbon atoms and the aryl is substituted or unsubstituted;
a glycosyl group selected from the group consisting of ribosyl, 2'-deoxyribosyl, 2',3'-dideoxyribosyl, 2',3'-dideoxy-2'-fluororibosyl, 2',3'-dideoxy-3'-fluororibosyl, 2',3'-dideoxy-2',3'-fluororibosyl, 2',3'-dideoxy-3'-azidoribosyl and mono-, di-, and triphosphate derivatives thereof;
—$(CH_2)_{m+n+1}$—R';
—$(CH_2)_m$—O—$(CH_2)_n$—O—R';
—$(CH_2)_{m+1}$—O—R';
—$(CH_2)_m$—O—$(CH_2)_n$—R';
wherein R' is selected from the group consisting of: hydrogen, $H_2PO_3$, $H_3P_2O_6$, $H_4P_3O_9$, and alkali metal or alkaline earth metal salts thereof;
m is zero to 20, n is zero to 20, and a is zero or one;
U, X, Y, Z, W, J, K, and L are selected from the group consisting of C and N;
and all chiral forms and stereoisomers of said compounds.

21. The method of claim 20 wherein said compound is administered subcutaneously, intravenously, intramuscularly, intraperitoneally, orally, topically, or by a combination thereof.

22. The method of claim 20 wherein said at least one compound is administered in combination with at least one known therapeutic agent.

23. The method of claim 20 wherein said compound is in a therapeutic form of a pharmaceutically acceptable salt, phosphonate, ester or salt of said ester, which provides said compound or its therapeutically effective metabolite during said treatment.

24. A method of treating Hepatitis B in a patient or vertebrate animal comprising administering the following compound to said patient or vertebrate animal in an amount sufficient to effect said treatment, 6-imino-6H-1-β-D-ribofuranosyl-4,5,7,8-tetrahydroimidazo[4,5-e][1,3]diazepine-4,8-dione.

25. The method of claim 24 wherein said compound is administered subcutaneously, intravenously, intramuscularly, intraperitoneally, orally, topically, or by a combination thereof.

26. The method of claim 24 wherein said compound is administered in combination with at least one known therapeutic agent.

27. The method of claim 24 wherein said compound is in a therapeutic form of a pharmaceutically acceptable salt, phosphonate, ester or salt of said ester, which provides said compound or its therapeutically effective metabolite during said treatment.

28. A method of treating Hepatitis B in a patient or vertebrate animal comprising administering the following compound to said patient or vertebrate animal in an amount sufficient to effect said treatment, 4,8-Diamino-6H-6-imino-1-β-D-ribofuranosylimidazo[4,5-e][1,3]diazepine.

29. The method of claim 28 wherein said compound is administered subcutaneously, intravenously, intramuscularly, intraperitoneally, orally, topically, or by a combination thereof.

30. The method of claim 28 wherein said compound is administered in combination with at least one known therapeutic agent.

31. The method of claim 28 wherein said compound is in a therapeutic form of a pharmaceutically acceptable salt, phosphonate, ester or salt of said ester, which provides said compound or its therapeutically effective metabolite during said treatment.

* * * * *